(12) United States Patent
Saifer et al.

(10) Patent No.: US 9,125,880 B2
(45) Date of Patent: Sep. 8, 2015

(54) POLYMER CONJUGATES OF INTERFERON-BETA WITH ENHANCED BIOLOGICAL POTENCY

(75) Inventors: Mark G. P. Saifer, San Carlos, CA (US); Alexa L. Martinez, San Jose, CA (US); L. David Williams, Fremont, CA (US); Merry R. Sherman, San Carlos, CA (US)

(73) Assignee: Mountain View Pharmaceuticals, Inc., Menlo Park, CA (US)

( * ) Notice: Subject to any disclaimer, the term of this patent is extended or adjusted under 35 U.S.C. 154(b) by 995 days.

(21) Appl. No.: 10/743,068

(22) Filed: Dec. 23, 2003

(65) Prior Publication Data

US 2004/0126361 A1    Jul. 1, 2004

Related U.S. Application Data

(60) Provisional application No. 60/479,913, filed on Jun. 20, 2003, provisional application No. 60/479,914, filed on Jun. 20, 2003, provisional application No. 60/436,020, filed on Dec. 26, 2002.

(51) Int. Cl.
*A61K 38/21* (2006.01)
*C07K 14/565* (2006.01)
*A61K 38/00* (2006.01)
*A61K 47/48* (2006.01)

(52) U.S. Cl.
CPC ......... *A61K 38/215* (2013.01); *A61K 47/48215* (2013.01); *C07K 14/565* (2013.01); *G01N 2333/565* (2013.01)

(58) Field of Classification Search
CPC ........... A61K 38/215; A61K 47/38215; C07K 14/565
See application file for complete search history.

(56) References Cited

U.S. PATENT DOCUMENTS

| | | |
|---|---|---|
| 4,002,531 A | 1/1977 | Royer |
| 4,179,337 A | 12/1979 | Davis et al. |
| 4,261,973 A | 4/1981 | Lee et al. |
| 4,301,144 A | 11/1981 | Iwashita et al. |
| 4,462,940 A | 7/1984 | Hanisch et al. |
| 4,588,585 A | 5/1986 | Mark et al. ............ 424/85 |
| 4,609,546 A | 9/1986 | Hiratani |
| 4,732,863 A | 3/1988 | Tomasi et al. |
| 4,766,106 A | 8/1988 | Katre et al. |
| 4,816,440 A | 3/1989 | Thomson |
| 4,847,325 A | 7/1989 | Shadle et al. |
| 4,894,330 A | 1/1990 | Hershenson et al. |
| 4,902,502 A | 2/1990 | Nitecki et al. |
| 4,904,584 A | 2/1990 | Shaw |
| 4,917,888 A | 4/1990 | Katre et al. |
| 4,961,969 A | 10/1990 | Hershenson et al. |
| 5,004,605 A | 4/1991 | Hershenson et al. |
| 5,006,333 A | 4/1991 | Saifer et al. |
| 5,037,969 A | 8/1991 | Minami et al. |
| 5,080,891 A | 1/1992 | Saifer et al. |
| 5,091,176 A | 2/1992 | Braatz et al. |
| 5,122,614 A | 6/1992 | Zalipsky |
| 5,166,322 A | 11/1992 | Shaw et al. |
| 5,183,660 A | 2/1993 | Ikeda et al. |
| 5,206,344 A | 4/1993 | Katre et al. |
| 5,219,564 A | 6/1993 | Zalipsky et al. |
| 5,252,714 A | 10/1993 | Harris et al. |

(Continued)

FOREIGN PATENT DOCUMENTS

| | | |
|---|---|---|
| EP | 0 229 108 B1 | 6/1986 |
| EP | 0 098 110 B1 | 10/1989 |
| EP | 0 539 167 A2 | 4/1993 |
| EP | 0 458 064 B1 | 2/1998 |
| EP | 0 822 199 A2 A3 | 2/1998 |
| EP | 0 439 508 B1 | 4/1998 |
| EP | 0 733 067 B1 | 5/1999 |
| EP | 1 037 657 B1 | 9/2000 |
| EP | 0 788 515 B1 | 4/2001 |
| EP | 1 039 922 B1 | 6/2002 |
| EP | 0 822 199 61 | 9/2004 |
| EP | 1 075 281 B1 | 9/2004 |

(Continued)

OTHER PUBLICATIONS

Schein C.H. The shape of the messenger: Using protein structure information to design novel cytokine-based therapeutics. Curr. Pharm. Design. Nov. 2002. vol. 8, p. 2113-2129.*

(Continued)

*Primary Examiner* — Robert Landsman
*Assistant Examiner* — Bruce D Hissong
(74) *Attorney, Agent, or Firm* — Sterne, Kessler, Goldstein & Fox P.L.L.C.

(57) ABSTRACT

Methods are provided for the synthesis of polymer conjugates of cytokines and receptor-binding antagonists thereof, especially a non-glycosylated interferon-beta, which conjugates retain unusually high biological potency. Preparation of polymer conjugates according to the methods of the present invention diminishes or avoids steric inhibition of receptor-ligand interactions that commonly results from the attachment of polymers to receptor-binding regions of cytokines, as well as to agonistic and antagonistic analogs thereof. The invention also provides conjugates and compositions produced by such methods. The conjugates of the present invention retain a high level of biological potency compared to those produced by traditional polymer coupling methods that are not targeted to avoid receptor-binding domains of cytokines. In assays in vitro, the biological potency of the conjugates of non-glycosylated interferon-beta of the present invention is substantially higher than that of unconjugated interferon-beta and is similar to that of interferon-beta-1a that is glycosylated. The conjugates of the present invention also exhibit an extended half-life in vivo compared to the corresponding unconjugated cytokine. The present invention also provides kits comprising such conjugates and/or compositions, and methods of use of such conjugates and compositions in a variety of diagnostic, prophylactic and therapeutic applications, including treatment of multiple sclerosis.

38 Claims, 25 Drawing Sheets

(56) References Cited

U.S. PATENT DOCUMENTS

| | | | |
|---|---|---|---|
| 5,281,698 A | 1/1994 | Nitecki | |
| 5,283,317 A | 2/1994 | Saifer et al. | |
| 5,324,844 A | 6/1994 | Zalipsky | |
| 5,349,052 A | 9/1994 | Delgado et al. | |
| 5,362,852 A | 11/1994 | Geoghegan et al. | |
| 5,382,657 A | 1/1995 | Karasiewicz et al. | |
| 5,395,619 A | 3/1995 | Zalipsky et al. | |
| 5,446,090 A | 8/1995 | Harris | |
| 5,460,811 A | 10/1995 | Goeddel et al. | 424/85.6 |
| 5,468,478 A | 11/1995 | Saifer et al. | |
| 5,476,653 A | 12/1995 | Pitt et al. | |
| 5,532,150 A | 7/1996 | Snow et al. | |
| 5,539,063 A | 7/1996 | Hakimi et al. | |
| 5,605,976 A | 2/1997 | Martinez et al. | |
| 5,612,460 A | 3/1997 | Zalipsky | |
| H001662 H | 7/1997 | Nishimura et al. | |
| 5,643,575 A | 7/1997 | Martinez et al. | |
| 5,661,020 A | 8/1997 | Snow et al. | |
| 5,672,662 A | 9/1997 | Harris et al. | |
| 5,681,567 A | 10/1997 | Martinez et al. | |
| 5,711,944 A | 1/1998 | Gilbert et al. | |
| 5,730,990 A | 3/1998 | Greenwald et al. | |
| 5,738,846 A | 4/1998 | Greenwald et al. | |
| 5,739,208 A | 4/1998 | Harris | |
| 5,747,646 A | 5/1998 | Hakimi et al. | |
| 5,756,593 A | 5/1998 | Martinez et al. | |
| 5,766,581 A | 6/1998 | Bartley et al. | |
| 5,770,577 A | 6/1998 | Kinstler et al. | |
| 5,792,834 A | 8/1998 | Hakimi et al. | |
| 5,808,096 A | 9/1998 | Zalipsky | |
| 5,824,784 A | 10/1998 | Kinstler et al. | |
| 5,834,594 A | 11/1998 | Hakimi et al. | |
| 5,849,860 A | 12/1998 | Hakimi et al. | |
| 5,880,255 A | 3/1999 | Delgado et al. | |
| 5,889,153 A | 3/1999 | Suzuki et al. | |
| 5,900,461 A | 5/1999 | Harris | |
| 5,902,588 A | 5/1999 | Greenwald et al. | |
| 5,919,455 A | 7/1999 | Greenwald et al. | |
| 5,932,462 A | 8/1999 | Harris et al. | |
| 5,935,564 A | 8/1999 | Seely | |
| 5,981,709 A | 11/1999 | Greenwald et al. | |
| 5,985,263 A | 11/1999 | Lee et al. | |
| 5,985,265 A | 11/1999 | Kinstler et al. | |
| 5,990,237 A | 11/1999 | Bentley et al. | |
| 6,042,822 A | 3/2000 | Gilbert et al. | |
| 6,077,939 A | 6/2000 | Wei et al. | |
| 6,113,906 A | 9/2000 | Greenwald et al. | |
| 6,132,763 A | 10/2000 | Fisher | |
| 6,340,742 B1 | 1/2002 | Burg et al. | |
| 6,384,195 B1 | 5/2002 | Delgado et al. | |
| 6,423,685 B1 | 7/2002 | Drummond et al. | |
| 6,455,639 B1 | 9/2002 | Yasukohchi et al. | |
| 6,482,613 B1 | 11/2002 | Goeddel et al. | 435/69.51 |
| 6,531,122 B1 | 3/2003 | Pedersen et al. | |
| 6,576,235 B1 | 6/2003 | Williams et al. | |
| 6,638,500 B1 | 10/2003 | El-Tayar et al. | |
| 6,770,746 B2 | 8/2004 | Gregg et al. | |
| 6,783,965 B1 | 8/2004 | Sherman et al. | |
| 6,887,462 B2 * | 5/2005 | Shirley et al. | 424/85.6 |
| 6,956,027 B2 | 10/2005 | Kinstler | |
| 7,090,835 B2 | 8/2006 | Gabriel et al. | |
| 2001/0016191 A1 | 8/2001 | Osslund | |
| 2002/0127244 A1 | 9/2002 | Delgado et al. | |
| 2002/0172661 A1 | 11/2002 | Shirley et al. | 424/85.6 |
| 2003/0021765 A1 | 1/2003 | Pepinsky et al. | |
| 2003/0053982 A1 | 3/2003 | Kinstler | |
| 2003/0096400 A1 | 5/2003 | Kinstler | |
| 2003/0105224 A1 | 6/2003 | Roberts et al. | |
| 2003/0170206 A1 | 9/2003 | Rasmussen et al. | |
| 2003/0175240 A1 | 9/2003 | Pedersen et al. | |
| 2003/0175241 A1 | 9/2003 | Pedersen et al. | |
| 2003/0219404 A1 | 11/2003 | Yamasaki et al. | 424/85.4 |
| 2004/0013644 A1 | 1/2004 | Rasmussen et al. | |
| 2004/0043002 A1 | 3/2004 | El-Tayar et al. | |
| 2004/0062746 A1 | 4/2004 | Martinez et al. | |
| 2004/0062748 A1 * | 4/2004 | Martinez et al. | 424/85.1 |
| 2004/0082765 A1 | 4/2004 | Nakamura et al. | |
| 2004/0116649 A1 * | 6/2004 | Kozlowski | 528/230 |
| 2004/0127417 A1 | 7/2004 | Finn | |
| 2004/0136952 A1 | 7/2004 | Bhaskaran et al. | |
| 2004/0142870 A1 | 7/2004 | Finn | |
| 2004/0181035 A1 | 9/2004 | Kinstler et al. | 530/350 |
| 2004/0191219 A1 | 9/2004 | Shirley et al. | 424/85.6 |
| 2004/0230040 A1 | 11/2004 | Cox, III | |
| 2004/0249576 A1 | 12/2004 | Desjarlais et al. | 702/19 |
| 2005/0107277 A1 * | 5/2005 | Lin et al. | 510/320 |
| 2006/0115450 A1 | 6/2006 | Nakamoto et al. | |
| 2007/0185135 A1 | 8/2007 | Wu et al. | |
| 2008/0058246 A1 | 3/2008 | Bhaskaran et al. | |

FOREIGN PATENT DOCUMENTS

| | | |
|---|---|---|
| EP | 1 564 236 A1 | 8/2005 |
| IL | 142282 | 8/2007 |
| JP | 5-214092 A | 8/1993 |
| RU | 2 298 560 C2 | 10/2005 |
| RU | 2004 113 379 A | 10/2005 |
| WO | WO 87/00056 | 6/1986 |
| WO | WO 89/01033 A1 | 2/1989 |
| WO | WO 89/05824 A1 | 6/1989 |
| WO | WO 89/06546 A1 | 7/1989 |
| WO | WO 92/16555 A1 | 10/1992 |
| WO | WO 93/00109 | 1/1993 |
| WO | WO 95/32003 | 11/1995 |
| WO | WO 96/11953 A1 | 4/1996 |
| WO | WO 96/40731 A1 | 12/1996 |
| WO | WO 99/03887 A1 | 1/1999 |
| WO | WO 99/32134 A1 | 7/1999 |
| WO | WO 99/32140 A1 | 7/1999 |
| WO | WO 99/45026 A1 | 9/1999 |
| WO | WO 99/55377 A2 | 11/1999 |
| WO | WO 99/58142 A1 | 11/1999 |
| WO | WO 00/07629 A2 A3 | 2/2000 |
| WO | WO 00/23114 A2 | 4/2000 |
| WO | WO 00/23114 A2 A3 | 4/2000 |
| WO | WO 00/42175 A1 | 7/2000 |
| WO | WO 01/02017 A2 A3 | 1/2001 |
| WO | WO 01/15736 A2 | 3/2001 |
| WO | WO 01/59078 A2 A3 | 8/2001 |
| WO | WO 01/87925 A2 | 11/2001 |
| WO | WO 02/02132 A1 | 1/2002 |
| WO | WO 02/049673 A2 | 6/2002 |
| WO | WO 02/074806 A2 | 9/2002 |
| WO | WO 03/002152 A2 | 1/2003 |
| WO | WO 03/031581 A2 | 4/2003 |
| WO | WO 03/049699 A2 | 6/2003 |
| WO | WO 03/049760 A1 | 6/2003 |
| WO | WO 03/061577 A2 | 7/2003 |
| WO | WO 03/075944 A2 A3 | 9/2003 |
| WO | WO 2004/046222 A1 | 11/2003 |
| WO | WO 2004/009774 A2 | 1/2004 |
| WO | WO 2004/020468 A2 | 3/2004 |
| WO | WO 2004/046365 A2 | 6/2004 |
| WO | WO 2004/060300 A2 | 7/2004 |
| WO | WO 2005/007197 A2 | 1/2005 |
| WO | WO 2005/084303 A2 | 9/2005 |

OTHER PUBLICATIONS

Youngster S, et al. Structure, biology, and therapeutic implications of pegylated interferon alpha-2b. Curr. Pharm. Design. Nov. 2002. vol. 8, p. 2139-2157.*

Mickle Je. et al. Genotype-phenotype relationships in cystic fibrosis. Med. Clin. N. Am. 2000. vol. 84, No. 3, pp. 597-607.*

Russell-Harde D., et al. The use of Zwittergent 3-14 in the purification of recombinant humant interferon-b Ser17 (Betaseron). J. Interferon and Cytokine Res., 1995, vol. 15, p. 31-37.*

Banga, A.K., et al. "Formulation of Therapeutic Peptides and Proteins", Therapeutic Peptides and Proteins: Formulation, Processing, and Delivery Systems, p. 81-163 (1995), Technomic Publishing Company, Inc. USA.*

(56) References Cited

OTHER PUBLICATIONS

Molineux G. Pegylation: engineering improved pharmaceuticals for enhanced therapy. Cancer Treatment Reviews, 2002, vol. 28 (Suppl. A), p. 13-16.*
Unverified partial translation of Doc. No. AM5 (WO04/046222 A1), published Mar. 6, 2004), pp. 12-13 (Tables 1 and 2); and 79-92 (Example 35, and claims 1-29).*
Unverified partial translation of Doc. No. AM5 (WO 04/046222 A1), pp. 12-13 (Tables 1 and 2); and 79-92 (Example 35, and claims 1-29).
Acharya, A.S., et. al., "Selectivity in the Modification of the α-Amino Groups of Hemoglobin on Reductive Alkylation with Aliphatic Carbonyl Compounds," J. Biol. Chem. 260:6039-6046, The American Society of Biological Chemististe, Inc. (1985).
Bayer, E., et. al., "Functionalization of Soluble Polymers: 4. Synthesis of Dichloro- and Di(4-Formylphenyloxyethyl) Poly(Oxyethylene)," Polymer Bulletin 8:585-592, Springer-Verlag (1982).
Bayer, E., et. al., "Functionalization of Soluble Polymers: 6. Preparation and Kinetic Aspects of Linear, Hydrophilic Aldehydes Based on Poly(Oxyethylene)," Polymer Bulletin 13:431-434, Springer-Verlag (1985).
Chamow, S.M., et. al., "Modification of CD4 Immunoadhesin with Monoethoxypoly(ethylene glycol) Aldehyde via Reductive Alkylation," Bioconjugate Chem. 5:133-140, American Chemical Society (1994).
Friedman, M., et. al., "Reductive Alkylation of Proteins with Aromatic Aldehydes and Sodium Cyanoborohydride," Int. J. Peptide Protein Res. 6:183-185, Munksgaard Internation Publishers (1974).
Harris, J.M., et. al., "New Polyethylene Glycols for Biomedical Applications," in Water-Soluble Polymers: Synthesis, Solution Properties, and Applications, Shalaby, S.W., et al., eds., 198th National Meeting of the American Chemical Society, Miami, Florida, pp. 418-429 (1989).
Harris, J.M., et. al., "Synthesis and Characterization of Poly(ethylene Glycol) Derivatives," Journal of Polymer Science 22:341-352, Polymer Chemistry Edition (1984).
Means, G.E., and Feeney, R.E., "Review: Reductive Alkylation of Proteins," Anal. Biochem. 224:1-16, Academic Press, Inc. (1995).
Means, G.E., and Feeney, R.E., "Alkylating and similar reagents," in Chemical Modification of Proteins, Holden-Day, Inc., San Francisco, CA, pp. 105-138 (1971).
Royer, G.P., "Immobilization of Enzymes on Aldehydic Matrices by Reductive Alyklylation," Biochemical and Biophysical Research Communications 64:478-484, Academic Press, Inc. (1975).
Zalipsky, S., "Functionalized Polymers and Their Biologically-Relevant Conjugates," in Biomedical Functions and Biotechnology of Natural and Artificial Polymers, Yalpani, M., ed., Atl Press, Shrewsbury, MA, pp. 63-76 (1996).
Abuchowski, A., et al., "Effect of covalent attachment of polyethylene gycol on immunogenicity and circulating life of bovine liver catalase," J Biol Chem 252:3582-3586, The American Society for Biochemistry and Molecular Biology 1977).
Abuchowski, A., et al., "Immunosuppressive properties and circulating life of Achromobecter glutaminase-asparaginase covalently attached to polyethylene glycol in man," Cancer Treat Rep 65:1077-1081, Kluwer Academic (1981).
Abuchowski, A., et al., "Cancer therapy with chemically modified enzymes. I. Antitumor properties of polyethylene glycol-asparaginase conjugates," Cancer Biochem Biophya 7:175-186, Gordon and Breach Science Publishers, Inc. (1984).
Sasser, R.L., et al., "Development of pancytopenia with neutralizing antibodies to thrombopoietin after multicycle chemotherapy supported by megakaryocyte growth and development factor," Blood 99:2599-2602, The American Society of Hematology (Apr. 2002).
Bertolotto, A., et. al., "Differential effects of three interferon betas on neutralising antibodies in patients with multiple sclerosis: a follow up study in an independent laboratory," J. Neurol. Neurosurg. Psychiatry. 73:148-153, BMJ Publishing Group (Apr. 2002).

Bowen, S., et al., "Relationship between molecular mass and duration of activity of polyethylene glycol conjugated granulocyte colony-stimulating factor mutein," Exp Hematol 27:425-432, Elsevier Science Inc. (1999).
Brenner, B.M., et al., "Glomerular permselectivity: Barrier function based on discrimination of molecular size and charge," Am J Physiol 234:F455-F460, American Physiological Society (1978).
Bruchelt, G, et al., "Determination of 2'-5'-oligoadenylate synthetase in serum and peripheral blood mononuclear cells before and after subcutaneous application of recombinant interferon beta and gamma," Eur J Clin Chem Clin Biochem 30:521-528, Walter de Gruyter & Co. (1992).
Brzozowaki, A.M., et al., "Structural origins of the functional divergence of human insulin-like growth factor-I and insulin," Biochemistry 41:9389-9397, American Chemical Society (Jul. 2002).
Bunn, P.A., et al., "Epidermal growth factor receptor expression, signal pathway, and inhibitors in non-small cell lung cancer," Semin Oncol 29:38-44, W.B. Saunders Company (Oct. 2002).
Cabacungan, J.C., et al., "Amine boranes as alternative reducing agents for reductive alkylation of proteins," Anal Biochem 124:272-278, Academic Press, Inc.
Carpenter, G., et al., "Epidermal growth factor," J Biol Chem 265:7709-7712, The American Society for Biochemistry and Molecular Biology (1990).
Chander, G., et al., "Treatment of chronic hepatitis C: A systematic review," Hepatology 36:S135-S144, Wiley (Nov. 2002).
Chapman, A.P., "PEGylated antibodies and antibody fragments for improved therapy: A review," Adv Drug Deliv Rev 54:531-545, Elsevier Science B.V. (Jun. 2002).
Chen, S.A., et al., "Plasma and lymph pharmacokinetics of recombinant human interleukin-2 and polyethylene glycol-modified interleukin-2 in pigs," J Pharmacol Exp Ther 293:248-259, The American Society for Pharmacology and Experimental Therapeutics (2000).
Chen, W.Y., et al., "A human prolactin antagonist, hPRL-G129R, inhibits breast cancer cell proliferation through induction of apoptosis," Clin Cancer Rea 5:3583-3593, The American Association for Cancer Research (1999).
Childs, C.E., "The determination of polyethylene glycol in gamma globulin solutions," Microchem J 20:190-192, Academic Press, Inc. (1975).
Clark, R., et al., "Long-acting growth hormones produced by conjugation with polyethylene glycol," J Biol Chem 271:21969-21977, The American Society for Biochemistry and Molecular Biology (1996).
Davis, S., et al., "Alteration of the circulating life and antigenic properties of bovine adenosine deaminase in mice by attachment of polyethylene glycol," Clin Exp Immunol 46:649-652, Blackwell Scientific Publications (1981).
Dixon, H.B.F., et al., "N-Terminal modification of proteins—A review," J Protein Chem 3:99-108, Plenum Publishing Corporation (1984).
Durelli, L., et. al., "Every-other-day interferon beta-1b versus once-weekly interferon beta-1a for multiple sclerosis: results of a 2-year prospective randomised mulitcentre study (INCOMIN)," The Lancet 359:1453-1460, Lancet Publishing Group (Apr. 2002).
Edsall, J.T., "Dipolar ions and acid-base equilibria," In: Proteins, Amino Acids and Peptides as Ions and Dipolar Ions, Cohn, E.J. et al., eds., Reinhold Publishing Corporation, N.Y., pp. 75-115 (1943).
Edsall, J.T. "Some relations between acidity and chemical structure," In: Proteins, Amino Acids and Peptides as Ions and Dipolar Ions, Cohn, E.J. et al., eds., Reinhold-Publishing Corporation, N.Y., pp. 116-139 (1943).
Fuke, I., et al., "Synthesis of poly(ethylene glycol) derivatives with different branchings and their use for protein modification," J Control Release 30:27-34, Elsevier Science B.V. (1994).
Gaertner, H.F., et al., "Site-specific attachment of functionalized poly(ethylene glycol) to the amino terminus of proteins," Bioconjug Chem 7:38-44, American Chemical Society (1996).
Geoghegan, K.F., et al., "Site-directed conjugation of nonpeptide groups to peptides and proteins via periodate oxidation of a 2-amino alcohol. Application to modification at N-terminal serine," Bioconjug Chem 3:138-146, American Chemical Society (1992).

(56) References Cited

OTHER PUBLICATIONS

Goffin, V., et al., "The prolactin/growth hormone receptor family: Structure/function relationships," *J Mammary Gland Biol Neoplasia* 2:7-17, Kluwer Academic/Plenum Publishers (1997).

Goodson, R. J., et al., "Site-directed PEGylation of recombinant interleukin-2 at its glycosylation site," *BioTechnology* 8:343-346, Nature Publishing Co. (1990).

Grace, M., et al., "Structural and biologic characterization of pegylated recombinant IFN-alpha2b," *J Interferon Cytokine Res* 21:1103-1115, Mary Ann Liebert, Inc. (Dec. 2001).

Guerra, P.I., et al., "PEGylation prevents the N-terminal degradation of megakaryocyte growth and development factor," *Pharm Res* 15:1822-1827, Plenum Publishing Corporation (1998).

Hershfield, M.S., et al., "Treatment of adenosine deaminase deficiency with polyethylene glycol-modified adenosine deaminase," *N Engl J Med* 316:589-596, Massachusetts Medical Society (1987).

Hinds, K., et al., "Synthesis and characterization of poly(ethylene glycol)-insulin conjugates," *Bioconjug Chem* 11:195-201, American Chemical Society (2000).

Hjelm Skog, A.-L., et al., "Alteration of interleukin 2 (IL-2) pharmacokinetics and function by IL-2 antibodies induced after treatment of colorectal carcinoma patients with a combination of monoclonal antibody 17-1A, granulocyte macrophage colony-stimulating factor, and IL-2," *Clin Cancer Res* 7.1163-1170, The American Association for Cancer Research (May 2001).

The IFNB Multiple Sclerosis Study Group. "Neutralizing antibodies during treatment of multiple sclerosis with interferon beta-1b: Experience during the first three years," *Neurology* 47:889-894, The American Academy of Neurology (1996).

Josephson, K, et al., "Design and analysis of an engineered human interleukin-10 monomer," *J Biol Chem* 275:13552-13557, The American Society for Biochemistry and Molecular Biology (2000).

Karpusas, M., et al., "The crystal structure of human interferon beta at 2.2-A resolution," *Proc Natl Acad Sci U S A* 94:11813-11818, National Academy of Sciences (1997).

Karpusas, M., et al., "The structure of human interferon-beta: Implications for activity," *Cell Mol Life Sci* 54:1203-1216, Birkhäuser Verlag, Basel, (1998).

Katre, N. V., "Immunogenicity of recombinant IL-2 modified by covalent attachment of polyethylene glycol," *J Immunol* 144:209-213, American Association of Immunologists (1990).

Kelly, S.J., et al., "Diabetes insipidus in uricase-deficient mice: A model for evaluating therapy with poly(ethylene glycol)-modified uricase," *J Am Soc Nephrol* 12:1001-1009, Lippincott Williams & Wilkins (May 2001).

Kinstler, O.B., et al., "Characterization and stability of N-terminally PEGylated rhG-CSF," *Pharm Res*, 13:996-1002, Plenum Publishing Corporation (1996).

Kinstler, O., et al., "Mono-N-terminal poly(ethylene glycol)-protein conjugates," *Adv Drug Deliv Rev* 54:477-485, Elsevier Science B.V. (Jun. 2002).

Kita, Y., et al., "Characterization of a polyethylene glycol conjugate of recombinant human interferon-gamma," *Drug Des Deliv* 6:157-167, Harwood Academic (1990).

Knauf, M. J., et al., "Relationship of effective molecular size to systemic clearance in rate of recombinant interleukin-2 chemically modified with watersoluble polymers," *J Biol Chem* 263:15064-15070, American Society for Biochemistry and Molecular Biology (1988).

Kochendorfer, G.G., et. al., "Design and Chemical Synthesis of a Homogeneous Polymer-Modified Erythropoiesis Protein," *Science* 299:884-887, American Association for the Advancement of Science (Feb. 2003).

Kuwabara, T., et al., "Renal clearance of a recombinant granulocyte colony-stimulating factor, nartograstim, in rats," *Pharm Res* 12:1466-1469, Plenum Publishing Corporation (1995).

Larson, R.S., et al., "Physicochemical characterization of poly(ethylene glycol)- modified anti-GAD antibodies," *Bioconjug Chem* 12:861-869, American Chemical Society (Nov.-Dec. 2001).

Laskowski, R.A., "PDSsum: Summaries and analyses of PDB structures," *Nucleic Acids Res* 29:221-222, Oxford University Press (Jan. 2001).

Lee, L.S., et al., "Prolonged circulating lives of single-chain Fv proteins conjugated with polyethylene glycol: a comparison of conjugation chemistries and compounds," *Bioconjug Chem* 10:973-981, American Chemical Society (1999).

Leong, S.R., et al., "Adapting pharmacokinetic properties of a humanized anti- interleukin-8 antibody for therapeutic applications using site-specific PEGylation," *Cytokine* 26:106-119, Academic Press, Inc. (Nov. 2001).

Li, J., et al., "Thrombocytopenia caused by the development of antibodies to thrombopoietin," *Blood* 98:3241-3248, American Society of Hematology (Dec. 2001).

Lin, L., "Betaseron," *Dev Biol Stand* 96:97-104, Karger (1998).

Lin, L.S., et al., "Interferon-beta-1b (Betaseron™): A model for hydrophobic therapeutic proteins," *Pharm Biotechnol* 9:275-301, Plenum Press (1996).

Lu, H.-S., et al., "Crystal structure of human epidermal growth factor and its dimerization," *J Biol Chem* 276:34913-34017, American Society for Biochemistry and Molecular Biology (Sep. 2001).

Manns, M.P., et al., "PEGinterferon alfa-2b plus ribavirin compared with interferon alfa-2b plus ribavirin for initial treatment of chronic hepatitis C: A randomised trial," *Lancet* 358:958-965, Lancet Publishing Group (Sep. 2001).

McNiece, I.K., et al., "Stem cell factor," *J Leukoc Biol* 58:14-22, Wiley-Liss, Inc. (1995).

Merrill, E.W., "Poly(ethylene oxide) star molecules: Synthesis, characterization, and applications in medicine and biology," *J Biomater Sci Polymer Edn* 5:1-11, VSP, The Netherlands (1993).

Monkarsh, S.P., et al., "Positional isomers of monopegylated interferon alpha-2a: Isolation, characterization, and biological activity," *Anal Biochem* 247:434-440, Academic Press, Inc. (1997).

Monkarsh, S.P., et al., "Isolation of positional isomers of mono-poly(ethylene glycol)ylate interferon/alpha-2a and the determination of their biochemical and biological characteristics," in Harris, J.M., et al., eds., *Poly(ethylene glycol): Chemistry and Biological Applications*, Ambrican Chemical Society, Washington, D.C., pp. 207-216 (1997).

Mordenti, J., et al., "Interspecies scaling of clearance and volume of distribution data for five therapeutic proteins," *Pharm Res* 8:1351-1359, Plenum Publishing Corporation (1991).

Morris, J.C., et al., "Advances in interleukin 2 receptor targeted treatment," *Ann Rheum Dis* 59 (Suppl I):i109-i114, BMJ Publishing Group Ltd. (2000).

Morrissey, P.J., et al., "Steel factor (c-kit ligand) stimulates the in vitro growth of immature CD3-/CD4-/CD8- thymocytes: Synergy with IL-7," *Cell Immunol* 157:118-131, Academic Press, Inc. (1994).

Nicola, N.A., "An introduction to the cytokines." in: *Guidebook to Cytokines and Their Receptors*, Nicola, N.A., ed., pp. 1-7, Oxford University Press, N.Y. (1994).

Peitsch, M.C., "About the use of protein models," *Bioinformatics* 28:934-938, Oxford University Press (Jul. 2002).

Pepinsky, R.B., et al., "Improved pharmacokinetic properties of a polyethylene glycol-modified form of interferon-beta-la with preserved in vitro bioactivity," *J Pharmacol Exp Ther* 297:1059-1066, American Society for Pharmacology and Experimental Therapeutics (Jun. 2001).

Peterson, F.C., "Identification of motifs associated with the lactogenic and somatotropic actions of human growth hormone," *Ph.D. Dissertation, Ohio State University*, (UMI # 9822357), UMI, Ann Arbor, MI (1998).

Pettit, D.K., et al., "Structure-function studies of interleukin 15 using site-specific mutagenesis, polyethylene glycol conjugation, and homology modeling," *J Biot Chem* 272:2312-2318, American Society for Biochemistry and Molecular Biology (1997).

Pungor, E., et al., "A novel bioassay for the determination of neutralizing antibodies to IFN-beta 1b." *J Interferon Cytokine Res* 18:1025-1030, Mary Ann Liebert, Inc. (1998).

Ragnhammar, P., et al., "Induction of anti-recombinant human granulocyte-macrophage colony-stimulating factor (*Escherichia coli*-de-

(56) References Cited

OTHER PUBLICATIONS rived) antibodies and clinical effects in nonimmunocompromised patients," *Blood* 84:4078-4087, American Society of Hematology (1994).

Roberts, M.J., et al., "Chemistry for peptide and protein PEGylation." *Adv Drug Deliv Rev* 54:459-476, Elsevier Science B.V. (Jun. 2002).

Ross, R.J.M., et al., "Binding and functional studies with the growth hormone receptor antagonist, B2036-PEG (pegvisomant), reveal effects of pegylation and evidence that it binds to a receptor dimer," *J Clin Endocrinol Metab* 86:1716-1723, The Endocrine Society (Apr. 2001).

Rostaing, L., et al., "Pharmacokinetics of alphaIFN-2b in chronic hepatitis C virus patients undergoing chronic hemodialysis or with normal renal function: Clinical implications," *J Am Soc Nephrol* 9:2344-2348, Lippincott Williams & Wilkins (1998).

Rozwarski, D.A., et al., "Refined crystal structure and mutagenesis of human granulocyte-macrophage colony-stimulating factor," *Proteins* 26:304-313, Wiley-Lies Inc. (1996).

Runkel, L., et al., "Systematic mutational mapping of sites on human interferon-beta-1a that are important for receptor binding and functional activity," *Biochemistry* 39:2538-2551, American Chemical Society (2000).

Rusconi, F., et al. "Quantification of sodium dodecyl sulfate in microliter-volume biochemical samples by visible light spectroscopy," *Anal Biochem* 295:31-37, Academic Press, Inc. (Aug. 2001).

Sato, H., "Enzymatic procedure for site-specific pegylation of proteins," *Adv Drug Deliv Rev* 54:487-504, Elsevier Science B.V. (Jun. 2002).

Sato, H., et al., "Transglutaminase-mediated dual and site-specific incorporation of poly(ethylene glycol) derivatives into a chimeric interleukin-2," *Bioconjug Chem* 11:502-509, American Chemical Society (2000).

Sayle, R.A., et al., "RASMOL: Biomolecular graphics for all," *Trends Biochem Sci* 20:374-376, Elsevier Trends Journals (1995).

Schellekens, H., "Immunogenicity of therapeutic proteins: Clinical implications and future prospects," *Clin Ther* 24:1720-1740, Excerpta Medico. (Nov. 2002).

Schlessinger, J., et al., "Crystal structure of a ternary FGF-FGFR-heparin complex reveals a dual role for heparin in FGFR binding and dimerization," *Mol Cell* 6:743-750, Cell Press (2000).

Sherman, M.R., et al., "Conjugation of high molecular weight poly-(ethylene glycol) to cytokines: Granulocyte-macrophage colony-stimulating factors as model substrates," *in: Poly(ethylene glycol): Chemistry and Biological Applications*, Harris, J.M., et al., eds., pp. 155-169, American Chemical Society, Washington, D.C. (1997).

Skoog, B., "Determination of polyethylene glycols 4000 and 6000 in plasma protein preparations," *Vox Sang* 37:345-349, Blackwell Science (1979).

Sundström, M., et al., "Crystal structure of an antagonist mutant of human growth hormone, G120R, in complex with its receptor at 2.9 a resolution," *J Biol Chem* 271:32197-32203, American Society for Biochemistry and Molecular Biology (1996).

Tchelet, A., et al., "Selective modification at the N-terminal region of human growth hormone that shows antagonistic activity," *Mol Cell Endocrinol* 130:141-152, North Holland Publishing (1997).

Thiel, D.J., et al., "Observation of an unexpected third receptor molecule in the crystal structure of human interferon-gamma receptor complex," *Structure* 8:927-936, Elsevier Science Ltd. (2000).

Utsumi, T., et al., "The role of amino functions in recombinant human tumor necrosis factor in expression of biological activity," *Mol Immunol* 29:77-81, Pergamon Press (1992).

Venkatachalam, M.A., et al., "The structural and molecular basis of glomerular filtration," *Circ Res* 43:337-347, Grune & Stratton (1978).

Wadhwa, M., et al., "Immunogenicity of granulocyte-macrophage colony-stimulating factor (GM-CSF) products in patients undergoing combination therapy with GM-CSF," *Clin Cancer Res* 5:1353-1361, The American Association for Cancer Research (1999).

Walter, M.R., et al., "Crystal structure of a complex between interferon-gamma and its soluble high-affinity receptor," *Nature* 376:230-235, Macmillan Magazines Ltd. (1995).

Wang, Y.-S., et al., "Structural and biological characterization of pegylated recombinant interferon alpha-2b and its therapeutic implications," *Adv Drug Deliv Rev* 54:547-570, Elsevier Science B.V. (Jun. 2002).

Weinreich, D.M., et al., "Response rates of patients with metastatic melanoma to high-dose intravenous interleukin-2 after prior exposure to alpha-interferon or low-dose interleukin-2," *J Immunother* 25:185-187, Lippincott Williams & Wilkins (Mar.-Apr. 2002).

Wilson, G., "Selective hepatic uptake of synthetic glycoproteins. Mannosaminated ribonuclease a dimer and serum albumin," *J Gen Physiol* 74:495-509, Rockefeller University Press (1979).

Wylie, D.C., et al., "Carboxyalkylated histidine is a pH-dependent product of pegylation with SC-PEG," *Pharm Res* 18:1354-1360, Plenum Publishing Corporation (Sep. 2001).

Zalipsky, S., et al., "Hydrazide derivatives of poly(ethylene glycol) and their bioconjugates," *In: Chemistry and Biological Applications of Poly(ethylene glycol)*, J.M. Harris, & S. Zalipsky, eds., American Chemical Society, Washington, D.C., pp. 318-341 (1997).

zhang, R-E., et al., "Synthesis and application of Fmoc-hydrazine for the quantitative determination of saccharides by reversed-phase high-performance liquid chromatography in the low and subpicomole range," *Anal Biochem* 195:160-167, Academic Press, Inc. (1991).

Runkel, L., et al. "Structural and functional differences between glycosylated and non-glycosylated forms of human interferon-β (IFN-β)," *Pharm. Res.* 15: 641-649 (1998).

Runkel, L., et al. "Differences in activity between alpha and beta type I interferons explored by mutational analysis " *J. Biol. Chem.* 273: 8003-8008 (1998).

Runkel, L., et al. "Systematic mutational mapping of sites on human interferon-β-1a that are important for receptor binding and functional activity " *Biochemistry* 39: 2538-2551 (2000).

Unverified English language translation of RU 2004 113 379 A, Transperfect Translation 3 pages (Mar. 2007).

English language Synopsis for RU 2 298 560, Application No. 2004113379/04, 3 pages (listed on accompanying PTO/SB/08A as document FP4).

Daro, E., et al., "Polyethylene Glycol-Modified GM-CSF Expands $CD11b^{high}CD11c^{high}$ But Not $CD11b^{low}CD11c^{high}$ Murine Dendritic Cells In Vivo: A Comparative Analysis with Flt3 Ligand," *J. Immunol.* 165:49-58 (2000).

Gnanou, Y., and Rempp, P., "Macromonomer synthesis. New functionalization methods," *Makromol. Chem.* 188:2111-2119 (1987).

Gombotz, W.R., and Pettit, D.K., "Pegylation: A Tool to Enhance Protein Delivery," *Polymer Prepr.* 40:275-276 (1999).

Knusli, C., et al., "Polyethylene glycol (PEG) modification of granulocyte-macrophage colony stimulating factor (GM-CSF) enhances neutrophil priming activity but not colony stimulating activity," *Br. J Haematol.* 82:654-663 (1992).

Saifer, M.G.P., et al., "Improved Conjugation of Cytokines Using High Molecular Weight Poly(ethylene glycol): PEG-GM-CSF as a Prototype," *Polymer Prepr.* 38:576-577 (1997).

Caliceti, P., et al., "Immunogenic and tolerogenic properties of monomethoxypoly(ethylene glycol) conjugated proteins," *IL Farmaco* 54:430-437, Elsevier (1999).

Clark, W.A., et al., "Site-specific $^{32}$P-labeling of cytokines, monoclonal antibodies, and other protein substrates for quantitative assays and therapeutic application," *Biotechniques Suppl*:76-87, Informa Healthcare USA, Inc. (Oct. 2002).

Hinds, K.D., and Kim, S.W., "Effects of PEG conjugation on insulin properties," *Adv. Drug Deliv. Rev.* 54:505-530, Elsevier Science Publishers, B.V. (Jun. 2002).

Koths, K., "Structure-function studies on human macrophage colony-stimulating factor (M-CSF)," *Mol. Reprod. Dev.* 46:31-38, Wiley-Liss (1997).

Lee, H., and Park, T.G., "Preparation and characterization of mono-PEGylated epidermal growth factor: evaluation of in vitro biologic activity," *Pharm. Res.* 19:845-851, Kluwer Academic/Plenum Publishers (Jun. 2002).

(56) References Cited

OTHER PUBLICATIONS

Pettit, D.K., et al., "Structure-function studies of interleukin 15 using site-specific mutagenesis, polyethylene glycol conjugation, and homology modeling," *J. Biol. Chem.* 272:2312-2318, American Society for Biochemistry and Molecular Biology (1997).

Tsutsumi, Y., et al., "Molecular design of hybrid tumor necrosis factor alpha with polyethylene glycol increases its anti-tumour potency," *Br. J. Cancer* 71:963-968, Stockton Press (1995).

Eliason, J.F, "Pegylated Cytokines Potential Application in Immunotherapy of Cancer," *BioDrugs* 15:705-711, Adis International Limited (2001).

Francis, G.E., "Protein modification and fusion proteins," *Focus on Growth Factor* 3:4-10, Royal Free Hospital School of Medicine, London, UK (1992).

May, L.T., et al., "Synthesis and Secretion of Multiple Forms of $\beta_2$,-Interferon/B-cell Differentiation Factor 2/Hepatocyte-Stimulating Factor by Human Fibroblasts and Monocytes," *J. Biol. Chem.* 263:7760-7766, The American Society for Biochemistry and Molecular Biology, Inc., U.S.A. (1988).

Cooke, R.M., et al., "Solution Structure of Human Insulin-Like Growth Factor 1: A Nuclear Magnetic Resonance and Restrained Molecular Dynamics Study," *Biochemistry* 30:5484-5491, American Chemical Society (1991).

Office Action mailed Sep. 27, 2006 in U.S. Appl. No. 10/743,295, inventors Bhaskaran et al., filed Dec. 23, 2003.

Office Action mailed Jul. 24, 2008 in U.S. Appl. No. 11/727,641, inventors Bhaskaran et al., filed Mar. 27, 2007.

Office Action mailed May 13, 2009 in U.S. Appl. No. 11/727,641, inventors Bhaskaran et al., filed Mar. 27, 2007.

Office Action mailed Dec. 24, 2009 in U.S. Appl. No. 11/727,641, inventors Bhaskaran et al., filed Mar. 27, 2007.

Office Action mailed Sep. 28, 2010 in U.S. Appl. No. 11/727,641, inventors Bhaskaran et al., filed Mar. 27, 2007.

Basu, A., et al., "Structure-Function Engineering of Interferon-$\beta$-1b for Improving Stability, Solubility, Potency, Immunogenicity, and Pharmacokinetic Properties by Site-Selective Mono-PEGylation," *Bioconjugate Chem.* 17:618-630, American Chemical Society, United States (May 2006).

Inada, Y., et al., "Engineering physicochemical and biological properties of proteins by chemical modification," *TIBTECH* 4(3):68-73, Elsevier Science Publishers B.V., Netherlands (1986).

Marti-Mestres, G. and Nielloud, F., "Main Surfactants Used in the Pharmaceutical Field," in *Pharmaceutical Emulsions and Suspensions*, Nielloud, F. and Marti-Mestres, G., Eds., pp. 1-18, Marcel Dekker, Inc., New York, United States (2000).

Roos, P.H., "Chapter 1: Ion Exchange Chromatography," in *Protein Liquid Chromatography*, Journal of Chromatography Library, vol. 61, Kastner, M., Ed., pp. 61-68, Elsevier Science B.V., Amsterdam, Netherlands (2000).

Office Action mailed Oct. 12, 2012, in Japanese Patent Application No. 2005-508613, including English language translation, Japanese Patent Office, Tokyo, Japan.

Arduini, R. M., et al., "Expression, purification, and characterization of rat interferon-beta, and preparation of an N-terminally pegylated form with improved pharmacokinetic parameters," *Protein Expr Purif* 34; 229-242, Academic Press, Inc. (Apr. 2004).

Bailon, P., et al., "Rational design of a potent, long-lasting form of interferon: A 40 kDa branched polyethylene glycol-conjugated interferon alpha-2a for the treatment of hepatitis C," *Bioconjug Chem* 12:195-202, American Chemical Society (Mar.-Apr. 2001).

Bamborough, P., et al., "The interleukin-2 and interleukin-4 receptors studied by molecular modeling." *Structure* 2:839-851, Elsevier Science Ltd. (1994).

Runkel, L., et al. "Mapping of IFN-$\beta$ epitopes important for receptor binding and biologic activation: Comparison of results achieved using antibody-based methods and alanine substitution mutagenesis," *J. Interferon Cytokine Res.* 21:931-941 (2001).*

* cited by examiner

POLYMER CONJUGATES OF INTERFERON-BETA WITH ENHANCED BIOLOGICAL POTENCY

CROSS REFERENCE TO RELATED APPLICATIONS

The present application claims the benefit of the filing dates of U.S. Provisional Appl. No. 60/479,913, filed Jun. 20, 2003; U.S. Provisional Appl. No. 60/479,914, filed Jun. 20, 2003; and U.S. Provisional Application No. 60/436,020, filed Dec. 26, 2002. The disclosures of the above-referenced applications are incorporated herein by reference in their entireties.

BACKGROUND OF THE INVENTION

1. Field of the Invention

The present invention is in the fields of protein biochemistry and the pharmaceutical and medical sciences. In particular, the invention provides methods for the production of conjugates between water-soluble polymers (e.g., poly(ethylene glycol) and derivatives thereof) and cytokines (e.g., interferon-beta), which conjugates have increased potency compared to polymer conjugates of the same cytokine synthesized by standard methods. The invention also provides conjugates produced by such methods, compositions comprising such conjugates, kits comprising such conjugates and compositions and methods of use of the conjugates and compositions in preventing, diagnosing and treating a variety of medical and veterinary conditions. The invention also provides methods of determining the site(s) of attachment of polymers by reductive alkylation under certain conditions.

2. Related Art

The following description of related art includes interpretations of the present inventors that are not, themselves, in the prior art. Cytokines are secreted regulatory proteins that control the survival, growth, differentiation, and/or effector function of cells in endocrine, paracrine or autocrine fashion (reviewed in Nicola, N. A. (1994) in: *Guidebook to Cytokines and Their Receptors*, Nicola, N. A., ed., pp. 1-7, Oxford University Press, New York). Because of their potency, specificity, small size and relative ease of production in recombinant organisms, cytokines have many potential applications as therapeutic agents. Two key factors have hindered the development of cytokines, in particular, and recombinant proteins, in general, as therapeutic agents—their generally short half-lives in the circulation and their potential antigenicity and immunogenicity. As used herein and generally in the art, the term "antigenicity" refers to the ability of a molecule to bind to preexisting antibodies, while the term "immunogenicity" refers to the ability of the molecule to evoke an immune response in vivo, whether that response involves the formation of antibodies (a "humoral response") or the stimulation of cellular immune responses.

For the administration of recombinant therapeutic proteins, intravenous (i.v.) administration is often desirable in order to achieve the highest circulating activities and to minimize problems of bioavailability and degradation. However, the half-lives of small proteins following i.v. administration are usually extremely short (see examples in Mordenti, J., et al., (1991) *Pharm Res* 8:1351-1359; Kuwabara, T., et al., (1995) *Pharm Res* 12:1466-1469). Proteins with hydrodynamic radii exceeding that of serum albumin, which has a Stokes radius of about 36 Å and a molecular weight of about 66,000 Daltons (66 kDa), are generally retained in the bloodstream by healthy kidneys. However, smaller proteins, including cytokines such as granulocyte colony-stimulating factor ("G-CSF"), interleukin-2 ("IL-2"), interferon-alpha ("IFN-alpha") and interferon-gamma ("IFN-gamma"), are cleared rapidly from the bloodstream by glomerular filtration (Brenner, B. M., et al., (1978) *Am J Physiol* 234:F455-F460; Venkatachalam, M. A. et al., (1978) *Circ Res* 43:337-347; Wilson, G., (1979) *J Gen Physiol* 74:495-509; Knauf, M. J., et al., (1988) *J Biol Chem* 263:15064-15070; Kita, Y., et al., (1990) *Drug Des Deliv* 6:157-167; Rostaing, L., et al., (1998), *J Am Soc Nephrol* 9:2344-2348). As a result, the maintenance of therapeutically useful concentrations of small recombinant proteins in the circulation is problematic following injection. Therefore, higher concentrations of such proteins and more frequent injections typically must be administered. The resulting dose regimens increase the cost of therapy, decrease the likelihood of patient compliance and increase the risk of adverse events, e.g., immune reactions. Both cellular and humoral immune responses can reduce the circulating concentrations of injected recombinant proteins to an extent that may preclude the administration of an effective dose or may lead to treatment-limiting events including accelerated clearance, neutralization of efficacy and anaphylaxis (Ragnhammar, P., et al., (1994) *Blood* 84:4078-4087; Wadhwa, M., et al., (1999) *Clin Cancer Res* 5:1353-1361; Hjelm Skog, A.- L., et al., (2001) *Clin Cancer Res* 7:1163-1170; Li, J., et al., (2001) *Blood* 98:3241-3248; Basser, R. L., et al., (2002) *Blood* 99:2599-2602; Schellekens, H., (2002) *Clin Ther* 24:1720-1740).

Modification of recombinant proteins by the covalent attachment of poly(ethylene glycol) ("PEG") has been investigated extensively as a means of addressing the shortcomings discussed above (reviewed in Sherman, M. R., et al., (1997) in: *Poly(ethylene glycol): Chemistry and Biological Applications*, Harris, J. M., et al., eds., pp. 155-169, American Chemical Society, Washington, D.C.; Roberts, M. J., et al., (2002) *Adv Drug Deliv Rev* 54:459-476). The attachment of PEG to proteins has been shown to stabilize the proteins, improve their bioavailability and/or reduce their immunogenicity in vivo. (The covalent attachment of PEG to a protein or other substrate is referred to herein, and is known in the art, as "PEGylation.") In addition, PEGylation can increase the hydrodynamic radius of proteins significantly. When a small protein such as a cytokine is coupled to a single long strand of PEG (e.g., having a molecular weight of at least about 18 kDa), the resultant conjugate has a hydrodynamic radius exceeding that of serum albumin and its clearance from the circulation via the renal glomeruli is retarded dramatically. The combined effects of PEGylation—reduced proteolysis, reduced immune recognition and reduced rates of renal clearance—confer substantial advantages on PEGylated proteins as therapeutic agents.

Since the 1970s, attempts have been made to use the covalent attachment of polymers to improve the safety and efficacy of various proteins for pharmaceutical use (see, e.g., Davis, F. F., et al., U.S. Pat. No. 4,179,337). Some examples include the coupling of PEG or poly(ethylene oxide) ("PEO") to adenosine deaminase (EC 3.5.4.4) for use in the treatment of severe combined immunodeficiency disease (Davis, S., et al., (1981) *Clin Exp Immunol* 46:649-652; Hershfield, M. S., et al., (1987) *N Engl J Med* 316:589-596), to superoxide dismutase (EC 1.15.1.1) for the treatment of inflammatory conditions (Saifer, M., et al., U.S. Pat. Nos. 5,006,333 and 5,080,891) and to urate oxidase (EC 1.7.3.3) for the elimination of excess uric acid from the blood and urine (Kelly, S. J., et al., (2001) *J Am Soc Nephrol* 12:1001-1009; Williams, L.

D., et al., PCT Publication No. WO 00/07629 A3 and U.S. Pat. No. 6,576,235; Sherman, M. R., et al., PCT Publication No. WO 01/59078 A2).

PEOs and PEGs are polymers composed of covalently linked ethylene oxide units. These polymers have the following general structure:

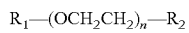

where $R_2$ may be a hydroxyl group (or a reactive derivative thereof) and $R_1$ may be hydrogen, as in dihydroxyPEG ("PEG diol"), a methyl group, as in monomethoxyPEG ("mPEG"), or another lower alkyl group, e.g., as in iso-propoxyPEG or t-butoxyPEG. The parameter n in the general structure of PEG indicates the number of ethylene oxide units in the polymer and is referred to herein and in the art as the "degree of polymerization." Polymers of the same general structure, in which $R_1$ is a $C_{1-7}$ alkyl group, have also been referred to as oxirane derivatives (Yasukohchi, T., et al., U.S. Pat. No. 6,455,639). PEGs and PEOs can be linear, branched (Fuke, I., et al., (1994) *J Control Release* 30:27-34) or star-shaped (Merrill, E. W., (1993) *J Biomater Sci Polym Ed* 5: 1-11). PEGs and PEOs are amphipathic, i.e., they are soluble in water and in certain organic solvents and they can adhere to lipid-containing materials, including enveloped viruses and the membranes of animal and bacterial cells. Certain random or block or alternating copolymers of ethylene oxide ($OCH_2CH_2$) and propylene oxide, which has the following structure:

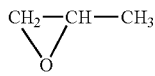

have properties that are sufficiently similar to those of PEG that these copolymers are thought to be suitable replacements for PEG in certain applications (see, e.g., Hiratani, H., U.S. Pat. No. 4,609,546 and Saifer, M., et al., U.S. Pat. No. 5,283, 317). The term "polyalkylene oxides" and the abbreviation "PAOs" are used herein to refer to such copolymers, as well as to PEG or PEO and poly(oxyethylene-oxymethylene) copolymers (Pitt, C. G., et al., U.S. Pat. No. 5,476,653). As used herein, the term "polyalkylene glycols" and the abbreviation "PAGs" are used to refer generically to polymers suitable for use in the conjugates of the invention, particularly PEGs, more particularly PEGs containing a single reactive group ("monofunctionally activated PEGs").

The covalent attachment of PEG or other polyalkylene oxides to a protein requires the conversion of at least one end group of the polymer into a reactive functional group. This process is frequently referred to as "activation" and the product is called "activated PEG" or activated polyalkylene oxide. MonomethoxyPEGs, in which an oxygen at one end is capped with an unreactive, chemically stable methyl group (to produce a "methoxy group") and on the other end with a functional group that is reactive towards amino groups on a protein molecule, are used most commonly for such approaches. So-called "branched" mPEGs, which contain two or more methoxyl groups distal to a single activated functional group, are used less commonly. An example of branched PEG is di-mPEG-lysine, in which PEG is coupled to both amino groups, and the carboxyl group of lysine is most often activated by esterification with N-hydroxysuccinimide (Martinez, A., et al., U.S. Pat. No. 5,643,575; Greenwald, R. B., et al., U.S. Pat. No. 5,919,455; Harris, J. M., et al., U.S. Pat. No. 5,932,462).

Commonly, the activated polymers are reacted with a bioactive compound having nucleophilic functional groups that serve as attachment sites. One nucleophilic functional group that is used commonly as an attachment site is the epsilon amino group of lysine residues. Solvent-accessible alpha-amino groups, carboxylic acid groups, guanidino groups, imidazole groups, suitably activated carbonyl groups, oxidized carbohydrate moieties and thiol groups have also been used as attachment sites.

The hydroxyl group of PEG has been activated with cyanuric chloride prior to its attachment to proteins (Abuchowski, A., et al., (1977) *J Biol Chem* 252:3582-3586; Abuchowski, A., et al., (1981) *Cancer Treat Rep* 65:1077-1081). The use of this method has disadvantages, however, such as the toxicity of cyanuric chloride and its non-specific reactivity for proteins having functional groups other than amines, such as solvent-accessible cysteine or tyrosine residues that may be essential for function. In order to overcome these and other disadvantages, alternative activated PEGs have been introduced, such as succinimidyl succinate derivatives of PEG ("SS-PEG") (Abuchowski, A., et al., (1984) *Cancer Biochem Biophys* 7:175-186), succinimidyl carbonate derivatives of PAG ("SC-PAG") (Saifer, M., et al., U.S. Pat. No. 5,006,333) and aldehyde derivatives of PEG (Royer, G. P., U.S. Pat. No. 4,002,531).

Commonly, several (e.g., 5 to 10) strands of one or more PAGs, e.g., one or more PEGs with a molecular weight of about 5 kDa to about 10 kDa, are coupled to the target protein via primary amino groups (the epsilon amino groups of lysine residues and, possibly, the alpha amino group of the amino-terminal ("N-terminal") amino acid). More recently, conjugates have been synthesized containing a single strand of mPEG of higher molecular weight, e.g., 12 kDa, 20 kDa or 30 kDa. Direct correlations have been demonstrated between the plasma half-lives of the conjugates and an increasing molecular weight and/or increasing number of strands of PEG coupled (Knauf, M. J., et al., supra; Katre, N. V. (1990) *J Immunol* 144:209-213; Clark, R., et al., (1996) *J Biol Chem* 271:21969-21977; Bowen, S., et al., (1999) *Exp Hematol* 27:425-432; Leong, S. R., et al., (2001) *Cytokine* 16:106-119). On the other hand, as the number of strands of PEG coupled to each molecule of protein is increased, so is the probability that an amino group in an essential region of the protein will be modified and hence the biological function of the protein will be impaired, particularly if it is a receptor-binding protein. For larger proteins that contain many amino groups, and for enzymes with substrates of low molecular weight, the tradeoff between increased duration of action and decreased specific activity may be acceptable, since it produces a net increase in the biological activity of the PEG-containing conjugates in vivo. For smaller proteins that function via interactions with cell-surface receptors, such as cytokines, however, a relatively high degree of substitution has been reported to decrease the functional activity to the point of negating the advantage of an extended half-life in the bloodstream (Clark, R., et al., supra).

Thus, polymer conjugation is a well-established technology for prolonging the bioactivity and decreasing the immunoreactivity of therapeutic proteins such as enzymes (see, e.g., U.S. Provisional Appl. No. 60/436,020, filed Dec. 26, 2002, and U.S. Provisional Appl. Nos. 60/479,913 and 60/479,914, both filed on Jun. 20, 2003, the disclosures of which are incorporated herein by reference in their entireties). A class of therapeutic proteins that would benefit especially from such decreased immunoreactivity are the interferon-betas, particularly interferon-beta-1b ("IFN-β-1b;" SEQ ID NO: 1) (The IFNB Multiple Sclerosis Study Group (1996)

*Neurology* 47:889-894). However, the conjugation of polymers to regulatory proteins that function by binding specifically to cell-surface receptors usually: (1) interferes with such binding; (2) markedly diminishes the signal transduction potencies of cytokine agonists; and (3) markedly diminishes the competitive potencies of cytokine antagonists. Published examples of such conjugates with diminished receptor-binding activity include polymer conjugates of granulocyte colony-stimulating factor ("G-CSF") (Kinstler, O., et al., PCT Publication No. WO 96/11953; Bowen, S., et al., supra); human growth hormone ("hGH") (Clark, R., et al., supra); hGH antagonists (Ross, R. J. M., et al., (2001) *J Clin Endocrinol Metab* 86:1716-1723; and IFN-alpha (Bailon, P., et al., (2001) *Bioconjug Chem* 12:195-202; Wylie, D. C., et al., (2001) *Pharm Res* 18:1354-1360; and Wang, Y.- S., et al., (2002) *Adv Drug Deliv Rev* 54:547-570), among others. In an extreme case, the coupling of polymers to interleukin-15 ("IL-15") converted this IL-2-like growth factor into an inhibitor of cellular proliferation (Pettit, D. K., et al., (1997) *J Biol Chem* 272:2312-2318). While not intending to be bound by theory, the mechanism for such undesirable effects of PEGylation may involve steric hindrance of receptor interactions by the bulky PEG groups, charge neutralization, or both.

Thus, there exists a need for methods for producing PAG-containing (e.g., PEG- and/or PEO-containing) conjugates, particularly conjugates between such water-soluble polymers and receptor-binding proteins, with preservation of substantial bioactivity (e.g., at least about 40%), nearly complete bioactivity (e.g., at least about 80%) or essentially complete bioactivity (e.g., at least about 90%). Such conjugates will have the benefits provided by the polymer component of increased solubility, stability and bioavailability in vivo and will exhibit substantially increased potency or utility, compared to conventional polymer conjugates, in an animal into which the conjugates have been introduced for prophylactic, therapeutic or diagnostic purposes.

BRIEF SUMMARY OF THE INVENTION

The present invention addresses the needs identified above, and provides methods for the preparation of conjugates of water-soluble polymers, e.g., poly(ethylene glycol), and derivatives thereof, with bioactive components, especially receptor-binding proteins, particularly therapeutic or diagnostic bioactive components such as cytokines including interferon-beta, and most particularly interferon-beta-1b. The invention also provides conjugates produced by such methods. Compared to the corresponding unconjugated bioactive components, the conjugates of the invention have increased stability (i.e., longer shelf life and longer half-lives in vivo). In addition, compared to conjugates of the same bioactive component prepared with polymer chains that are attached randomly to solvent-accessible sites along the polypeptide chains, the conjugates of the invention have increased receptor-binding activity, which can be measured or employed in vitro, and increased potency, which can be measured either in vitro or in vivo. Furthermore, the invention provides compositions comprising such conjugates, kits containing such conjugates and compositions and methods of use of the conjugates and compositions in a variety of therapeutic and diagnostic regimens.

In one embodiment, the invention provides methods for enhancing the potency of a cytokine. Certain methods according to this aspect of the invention comprise, for example, selectively coupling one or more synthetic water-soluble polymers to the amino-terminal amino acid of the cytokine, wherein the amino-terminal amino acid is located remotely from one or more receptor-binding domains of the cytokine. Related methods provided by the invention for enhancing the potency of a cytokine comprise, for example, selectively coupling one or more synthetic water-soluble polymers at or near one or more glycosylation sites of the cytokine, wherein the one or more glycosylation sites is/are located remotely from one or more receptor-binding domains of the cytokine.

Suitable polymers for use in these methods of the invention include, but are not limited to, one or more polyalkylene glycols (including, but not limited to, one or more poly(ethylene glycols), one or more monomethoxy-poly(ethylene glycols) and one or more monohydroxypoly(ethylene glycols)), one or more polyalkylene oxides, one or more polyoxiranes, one or more polyolefinic alcohols, e.g., polyvinyl alcohol, one or more polycarboxylates, one or more poly(vinylpyrrolidones), one or more poly(oxyethylene-oxymethylenes), one or more poly(amino acids), one or more polyacryloyl-morpholines, one or more copolymers of one or more amides and one or more alkylene oxides, one or more dextrans and one or more hyaluronic acids. Polymers suitable for use in the methods of the invention typically have molecular weights of between about 1 kDa and about 100 kDa, inclusive, or more particularly molecular weights of between about 8 kDa and about 14 kDa, inclusive; between about 10 kDa and about 30 kDa, inclusive; between about 18 kDa and about 22 kDa, inclusive; or of about 20 kDa or about 30 kDa.

A variety of cytokines and analogs that mimic (i.e., agonize) or antagonize the biological effects of the corresponding cytokine that are mediated by their specific cell-surface receptors are suitable for use in preparing the present conjugates. These include cytokines having a four helix bundle structure (including but not limited to granulocyte colony-stimulating factor (G-CSF), macrophage colony-stimulating factor (M-CSF), granulocyte-macrophage colony-stimulating factor (GM-CSF), leukemia inhibitory factor (LIF), erythropoietin (Epo), thrombopoietin (Tpo), stem cell factor (SCF), Flt3 ligand, oncostatin M (OSM), interleukin-2 (IL-2), IL-3, IL-4, IL-5, IL-6, IL-7, IL-9, IL-10, IL-11, IL-12 (p35 subunit), IL-13, IL-15, IL-17, interferon-alpha (IFN-α), interferon beta (IFN-β) (particularly IFN-β-1b), consensus interferon and muteins, variants, analogs and derivatives thereof) and cytokines having a β-sheet or β-barrel structure (including but not limited to tumor necrosis factor alpha (TNF-α), IL-1α, IL-1β, IL-12 (p40 subunit), IL-16, epidermal growth factor (EGF), insulin-like growth factor-1 (IGF-1), basic fibroblast growth factor (bFGF), acidic FGF, FGF-4 and keratinocyte growth factor (KGF; FGF-7), and muteins, variants, analogs and derivatives thereof).

Particularly preferred cytokines suitable for use in accordance with the present invention include IL-2; IFN-α; IFN-β; IGF-1; EGF and bFGF. Also particularly suitable for use are competitive antagonists of the foregoing cytokines as well as muteins, variants and derivatives of these cytokines.

In certain embodiments, the one or more polymers is/are covalently coupled (particularly via a secondary amine linkage) to the alpha amino group of the amino-terminal amino acid on the cytokine. In other embodiments, the one or more polymers is/are covalently coupled to a chemically reactive side chain group (e.g., a hydroxyl group, a sulfhydryl group, a guanidino group, an imidazole group, an amino group, a carboxyl group or an aldehyde derivative) of the amino-terminal amino acid on the cytokine. In additional embodiments, the coupling of the polymer to the cytokine at the amino-terminal amino acid or at or near one or more glycosylation sites mimics the beneficial effects of glycosylation of the cytokine. In related embodiments, the coupling of the polymer to the cytokine at or near one or more glycosylation sites on the cytokine mimics the beneficial effects of hyperglycosylation of the cytokine, wherein "hyperglycosylation" indicates the covalent attachment of simple or complex carbohydrate moieties in addition to those present in the native structure.

The invention also provides conjugates produced by the methods of the invention. Conjugates of the invention comprise a selected cytokine or a selected antagonist thereof (such as those described above) coupled to one or more synthetic water-soluble polymers (such as those described above), wherein the one or more polymers is/are coupled to the amino-terminal amino acid of the cytokine and wherein the amino-terminal amino acid is located remotely from one or more receptor-binding domains of the selected cytokine. Additionally, conjugates of the invention comprise a selected cytokine or a selected antagonist thereof (such as those described above) coupled to one or more synthetic water-soluble polymers (such as those described above), wherein the one or more polymers is coupled to one or more glycosylation sites of the selected cytokine and wherein the one or more glycosylation sites is/are located remotely from one or more receptor-binding domains of the cytokine. For polymer conjugates of agonists of the invention, it is preferable that the site(s) of polymer attachment be remote from all of the receptor-binding domains. For polymer conjugates of certain antagonists of the invention, it may be preferable that the site(s) of polymer attachment be remote from certain receptor-binding domains that are essential for binding to occur, but not necessarily remote from all of the receptor-binding domains that are essential for signal transduction by agonists. The invention also provides compositions, particularly pharmaceutical compositions, comprising one or more of the conjugates of the invention and one or more additional components, such as one or more pharmaceutically acceptable diluents, excipients or carriers. The invention also provides kits comprising one or more of the conjugates, compositions and/or pharmaceutical compositions of the invention.

The invention also provides methods of preventing, diagnosing, or treating a physical disorder in an animal (e.g., a mammal such as a human) suffering from or predisposed to the physical disorder. Such methods may comprise, for example, administering to the animal an effective amount of one or more of the conjugates, compositions or pharmaceutical compositions of the present invention. Physical disorders suitably treated or prevented according to such methods of the invention include, but are not limited to, cancers (e.g., a breast cancer, a uterine cancer, an ovarian cancer, a prostate cancer, a testicular cancer, a lung cancer, a leukemia, a lymphoma, a colon cancer, a gastrointestinal cancer, a pancreatic cancer, a bladder cancer, a kidney cancer, a bone cancer, a neurological cancer, a head and neck cancer, a skin cancer, a sarcoma, a carcinoma, an adenoma and a myeloma); infectious diseases (e.g., bacterial diseases, fungal diseases, parasitic diseases and viral diseases (such as a viral hepatitis, a disease caused by a cardiotropic virus, HIV/AIDS, and the like)); and genetic disorders (e.g., anemia, neutropenia, thrombocytopenia, hemophilia, dwarfism and severe combined immunodeficiency disease ("SCID"); autoimmune disorders (e.g., psoriasis, systemic lupus erythematosus and rheumatoid arthritis) and neurodegenerative disorders (e.g., various forms and stages of multiple sclerosis ("MS") such as relapsing-remitting MS, primary progressive MS and secondary progressive MS; Creutzfeldt-Jakob Disease; Alzheimer's Disease; and the like).

In related embodiments, the invention also provides methods for determining the amount of a polymer that is attached to the amino terminus of a protein having an N-terminal serine residue, in a polymer-protein conjugate synthesized by reductive alkylation. Methods according to this aspect of the invention comprise, for example, (a) reacting the conjugate with a sufficient quantity of an oxidizing agent for a sufficient time to cleave the polymer from the serine residue of the protein; and (b) measuring the increase in the portion of unconjugated protein in the preparation. Proteins suitable for use in accordance with such methods include, but are not limited to, cytokines (including interferon-beta (particularly interferon-beta-1b, which preferably has the amino acid sequence specified in SEQ ID NO:1) and megakaryocyte growth and development factor). The oxidizing agent used in certain such methods of the invention may be a periodate including, but not limited to, sodium metaperiodate, potassium metaperiodate, lithium metaperiodate, calcium periodate, barium periodate and periodic acid. Suitable methods for measuring the increase in the portion of unconjugated protein in the preparation include any variety of art-known methods of protein and peptide analysis, including, for example, size-exclusion chromatography, reversed phase chromatography, gel electrophoresis, capillary electrophoresis, ultracentrifugation, ultrafiltration, light scattering and mass spectroscopy.

In additional related embodiments, the invention provides methods for the selective oxidative cleavage of an N-terminal serine residue of a bioactive protein without oxidizing functionally essential amino acid residues of said bioactive protein. Certain such methods of the invention comprise, for example, (a) adjusting the hydrogen ion concentration of a solution of the bioactive protein to a pH of between about 5 and about 10, more preferably a pH of between about 7 and about 8; (b) mixing the solution of bioactive protein with about 0.1 moles to about 10 moles, or more preferably with about 0.5 moles to about 5 moles, of a periodate per mole of bioactive protein; and (c) incubating said mixture for at least one hour, preferably at a temperature of between about 2° C. and about 40° C. Proteins suitable for use in accordance with such methods include, but are not limited to, cytokines (including interferon-beta (particularly interferon-beta-1b, which preferably has the amino acid sequence specified in SEQ ID NO:1).

In additional embodiments, the invention provides methods for increasing the biological potency of a preparation of interferon-beta, particularly a preparation of interferon-beta-1b, comprising removal of one or more inhibitory components of an interferon-beta (or interferon-beta-1b) preparation. According to this aspect of the invention, the one or more inhibitory components can be removed from the preparations by a variety of art-known methods of protein and peptide processing, purification and/or analysis, including but not limited to one or more chromatographic methods such as size-exclusion chromatography, reversed phase chromatography, hydrophobic interaction chromatography and affinity chromatography. The determination of the biological potency of a given preparation of interferon-beta (i.e., whether the potency is increased, decreased or unaffected, relative to a stock solution of interferon-beta) can be accomplished by any number of in vitro or in vivo assays that will be familiar to the ordinarily skilled artisan. For example, a cell culture assay that responds to interferon-beta can be used to determine the biological potency of interferon-beta preparations. Non-limiting examples of suitable such cell culture assays include antiproliferative assays, antiviral assays, signal transduction assays and gene activation assays, examples of which are well-known to those of ordinary skill in the art.

Other preferred embodiments of the present invention will be apparent to one of ordinary skill in light of the following drawings and description of the invention, and of the claims.

BRIEF DESCRIPTION OF THE DRAWINGS

FIGS. 1 through 8 display molecular models of various cytokines and growth factors created with RasMol software (Sayle, R. A., et al., (1995) *Trends Biochem Sci* 20:374-376) based on crystallographic data. Each of the models is represented in "ribbon" or "cartoon" format, except for certain residues of particular interest, which are shown in "ball-and-stick" format. These formats are options selected using RasMol software. The dark parts of the ribbons represent domains of the cytokines and growth factors that are reported to be involved in binding to their receptors. For each structure, the accession code in the Protein Data Bank ("PDB") is indicated (see Laskowski, R. A., (2001) *Nucleic Acids Res* 29:221-222; Peitsch, M. C., (2002) *Bioinformatics* 18:934-938; Schein, C. H., (2002) *Curr Pharm Des* 8:2113-2129).

FIG. 2 shows a molecular model of human interferon-beta-1a (see SEQ ID NO:2), in which several lysine residues that are within or adjacent to the receptor-binding domains are indicated (Lys 19, Lys 33, Lys 99 and Lys 134). In addition, the glycosylation site (Asn 80) and the N-terminal methionine residue ("Met 1") are shown in "ball-and-stick" format (based on data of Karpusas, M., et al., (1997) *Proc Natl Acad Sci USA* 94:11813-11818; Karpusas, M., et al., (1998) *Cell Mol Life Sci* 54:1203-1216; Runkel, L., et al., (2000) *Biochemistry* 39:2538-2551). Met 1 is remote from Binding Sites 1 and 2, whereas several lysine residues are located within the receptor-binding domains. (PDB code 1AUI) The structure of interferon-beta-1b (see SEQ ID NO:1) differs from that of interferon-beta-1a in lacking the N-terminal methionine residue and carbohydrate moiety, as well as having a serine residue substituted for the unpaired cysteine residue (Cys 17 of SEQ ID NO:2).

FIG. 3 shows a molecular model of human granulocyte-macrophage colony-stimulating factor ("GM-CSF") in which three lysine residues (Lys 72, Lys 107 and Lys 111) that are within the receptor-binding domains, as well as the first amino acid residue near the amino terminus that is visualized in the crystal structure ("Arg 4"), are shown in "ball-and-stick" format (based on data of Rozwarski, D. A., et al., (1996) *Proteins* 26:304-313). The amino-terminal region of GM-CSF is remote from Binding Sites 1 and 2. (PDB code 2GMF)

FIG. 4 shows a molecular model of human interleukin-2, in which the amino acid residues that are reported to be involved with each of three receptors (alpha, beta and gamma) are represented in "ball-and-stick" format, as are several lysine residues that are within or close to the receptor-binding domains. The closest amino acid residue to the amino terminus that is visualized in the crystal structure is serine 6 ("Ser 6"), which is remote from the receptor-binding domains (based on data of Bamborough, P., et al., (1994) *Structure* 2:839-851; Pettit, D. K., et al., supra). (PDB code 3INK)

FIG. 5 shows a molecular model of human epidermal growth factor ("EGF") in "cartoon" format, except for the residues that are implicated in receptor binding and the two lysine residues (Lys 28 and Lys 48) that are adjacent to receptor-binding regions. The intra-chain disulfide bonds are shown as dashed lines. The closest amino acid residue to the amino terminus that is visualized in the crystal structure on which this model is based is cysteine 6 ("Cys 6") (based on data of Carpenter, G., et al., (1990) *J Biol Chem* 265:7709-7712; Lu, H.- S., et al., (2001) *J Biol Chem* 276:34913-34917). The flexible portion of the amino terminus of EGF (residues 1-5) that is not visualized in the crystal structure does not appear to be in a receptor-binding region. (PDB code 1JL9)

FIG. 6 shows a molecular model of basic fibroblast growth factor ("bFGF") in "cartoon" format in which the residues involved in binding to the receptors and to heparin are identified by presentation in "ball-and-stick" format (based on data of Schlessinger, J., et al., (2000) *Mol Cell* 6:743-750). The first 12 amino acid residues from the amino terminus have not been implicated in receptor binding. (PDB code 1FQ9)

FIG. 7 shows a molecular model of insulin-like growth factor-1 ("IGF-1") in "cartoon" format, except for the residues involved in receptor binding (23-25 and 28-37), and glutamic acid residue 3 ("Glu 3"), which is the closest amino acid residue to the amino terminus that is visualized in the crystal structure. Two of the lysine residues are identified, one of which (Lys 27) is adjacent to the receptor-binding domain, and the other of which is remote from the receptor-binding domain (based on data of Brzozowski, A. M., et al., (2002) *Biochemistry* 41:9389-9397). The amino terminus of IGF-1 is remote from the receptor-binding domains. (PDB code 1GZR)

FIG. 8 shows a molecular model of an interferon-gamma ("IFN-gamma"), which is a homodimer. To clarify the interactions between the two polypeptide chains, one of the monomers ("Chain A") is shown in "ribbon" format and the other ("Chain B") is shown in "backbone" format. Lysine residues (shown in light "ball and stick" format) occur along the polypeptide chain, including the regions that are involved in the interface between the monomers or are adjacent to amino acid residues that are involved in receptor binding. The amino-terminal region of IFN-gamma is remote from the dimerization interface, but glutamine 1 (Gln 1) has been implicated in receptor binding. (Thiel, D. J., et al., (2000) *Structure* 8:927-936; PDB code 1FG9)

IFN") by cation-exchange chromatography of a reaction mixture containing IFN, 20-kDa mPEG-aldehyde and a reducing agent.

Figure 9:
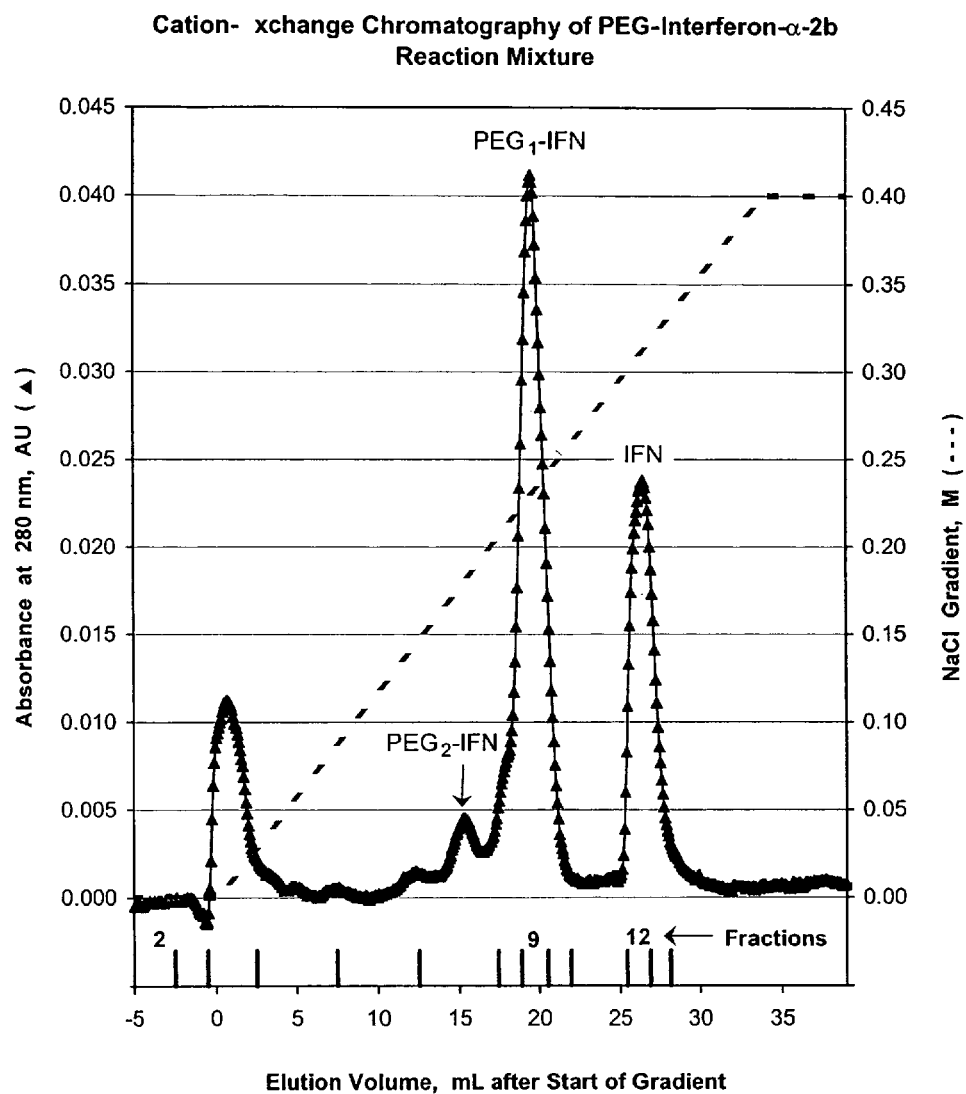
FIG. 9 shows the fractionation of unPEGylated interferon-alpha-2b ("IFN"), monoPEGylated interferon-alpha-2b ("$PEG_1$-IFN") and diPEGylated interferon alpha-2b ("$PEG_2$-
Figure 10:
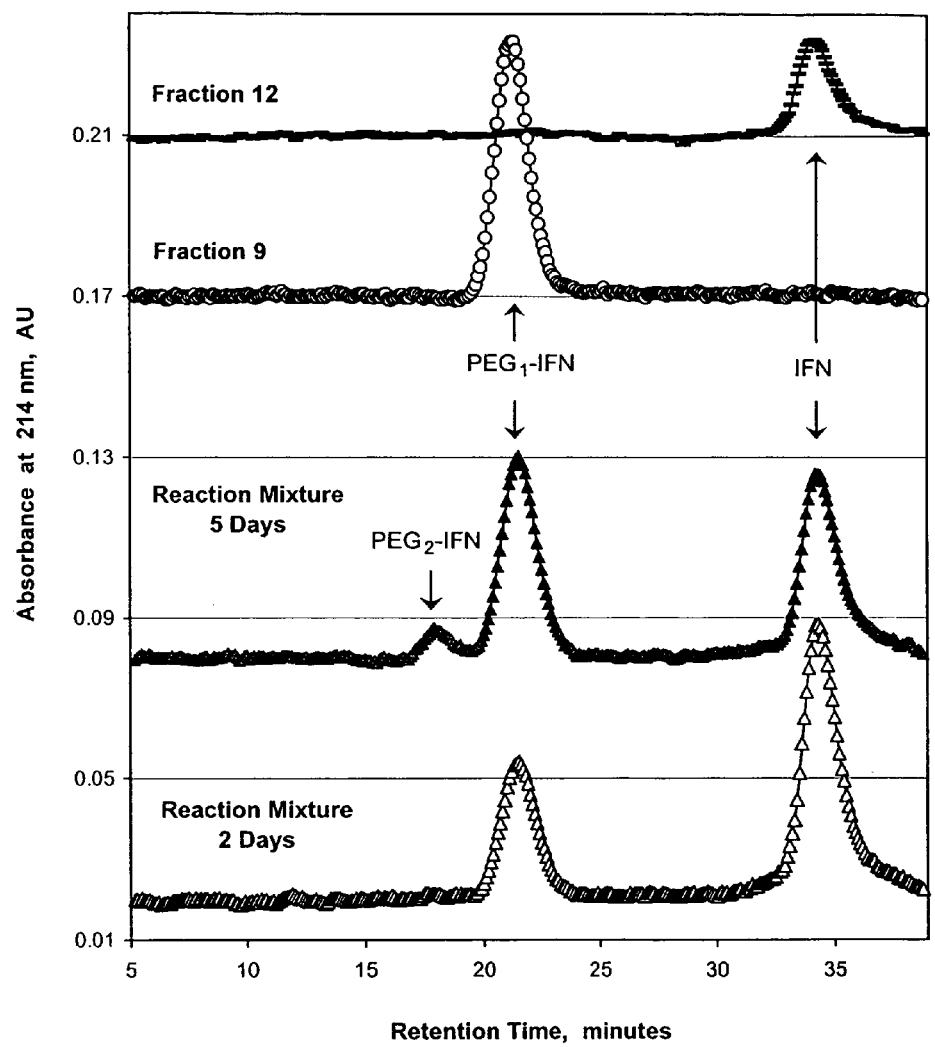

FIG. 10 shows size-exclusion chromatographic analysis of the reaction mixture fractionated as shown in FIG. 9 and of selected fractions collected from the ion-exchange column for which results are shown in FIG. 9.

Figure 11:
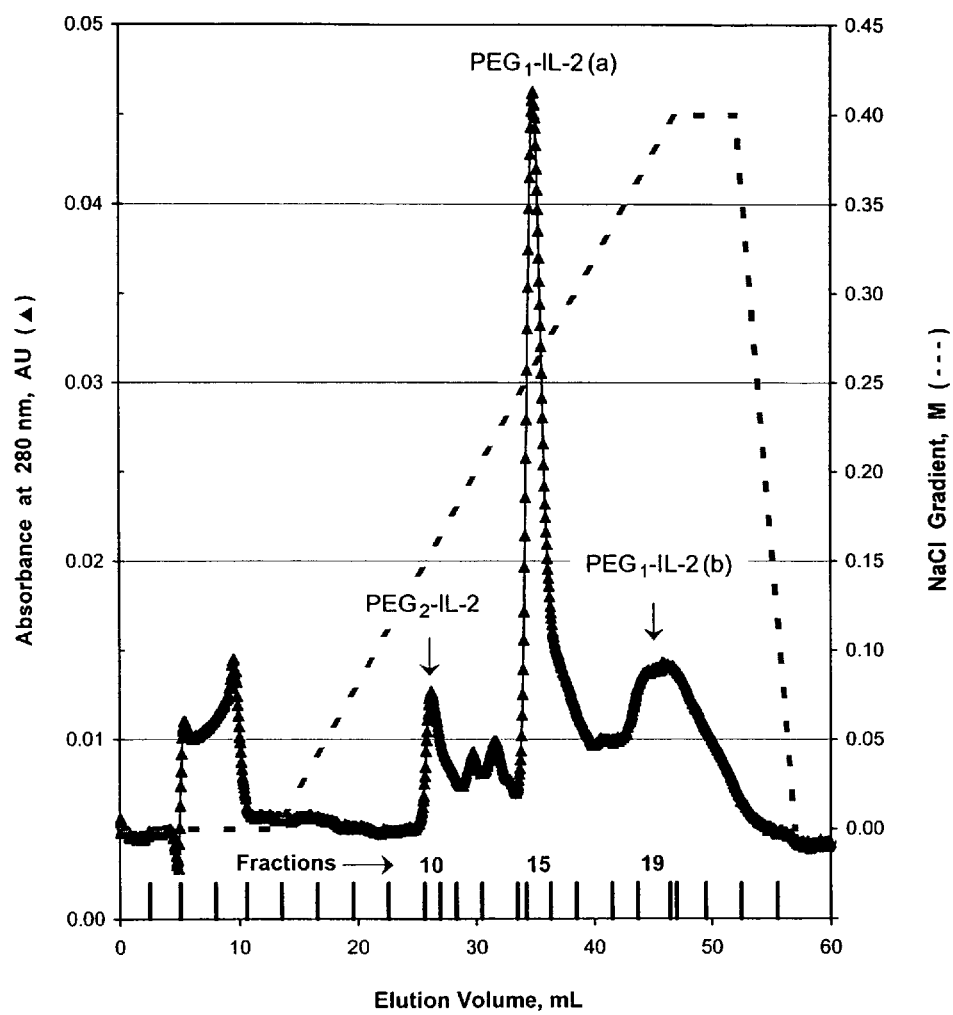

FIG. 11 shows the fractionation by cation-exchange chromatography of a reaction mixture containing human IL-2, 20-kDa mPEG-aldehyde and a reducing agent. Under the indicated elution conditions, the residual unPEGylated IL-2 was not eluted from the column, unlike the results for interferon-alpha-2b shown in FIG. 9.

Figure 12:
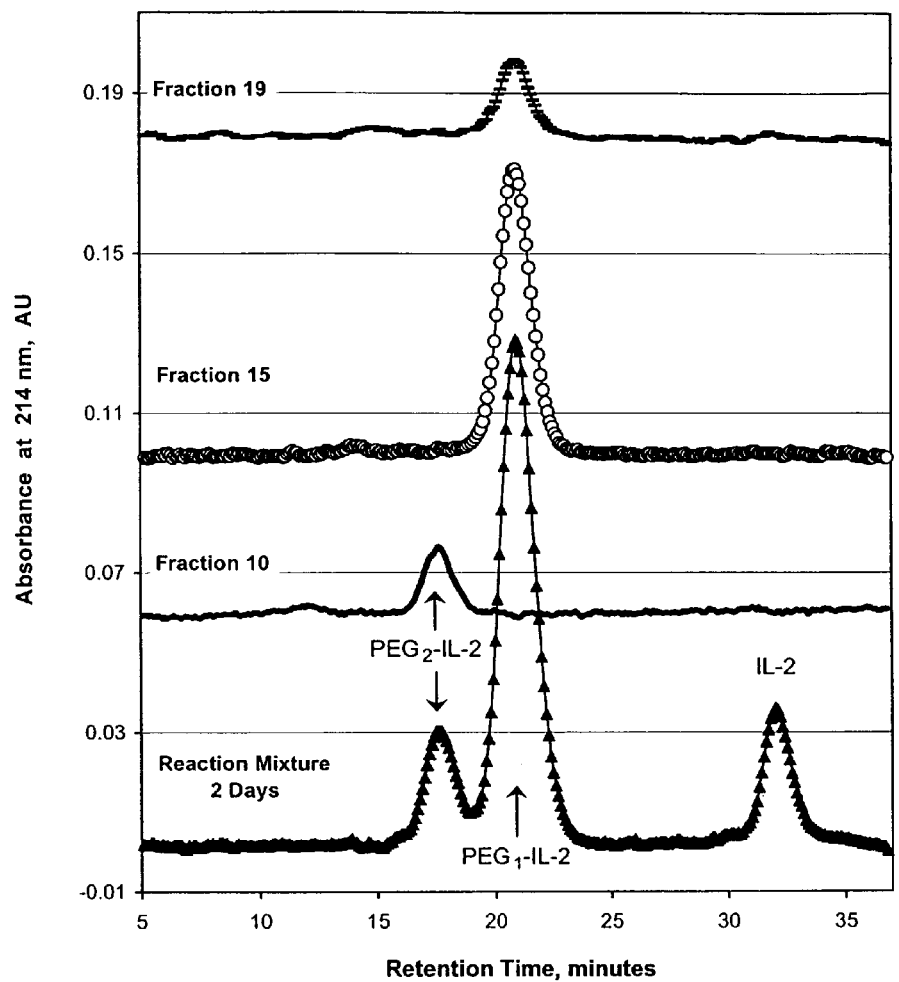

FIG. 12 shows a size-exclusion chromatographic analysis of the reaction mixture fractionated as shown in FIG. 11 and of selected fractions eluted from that column.

Figure 13:
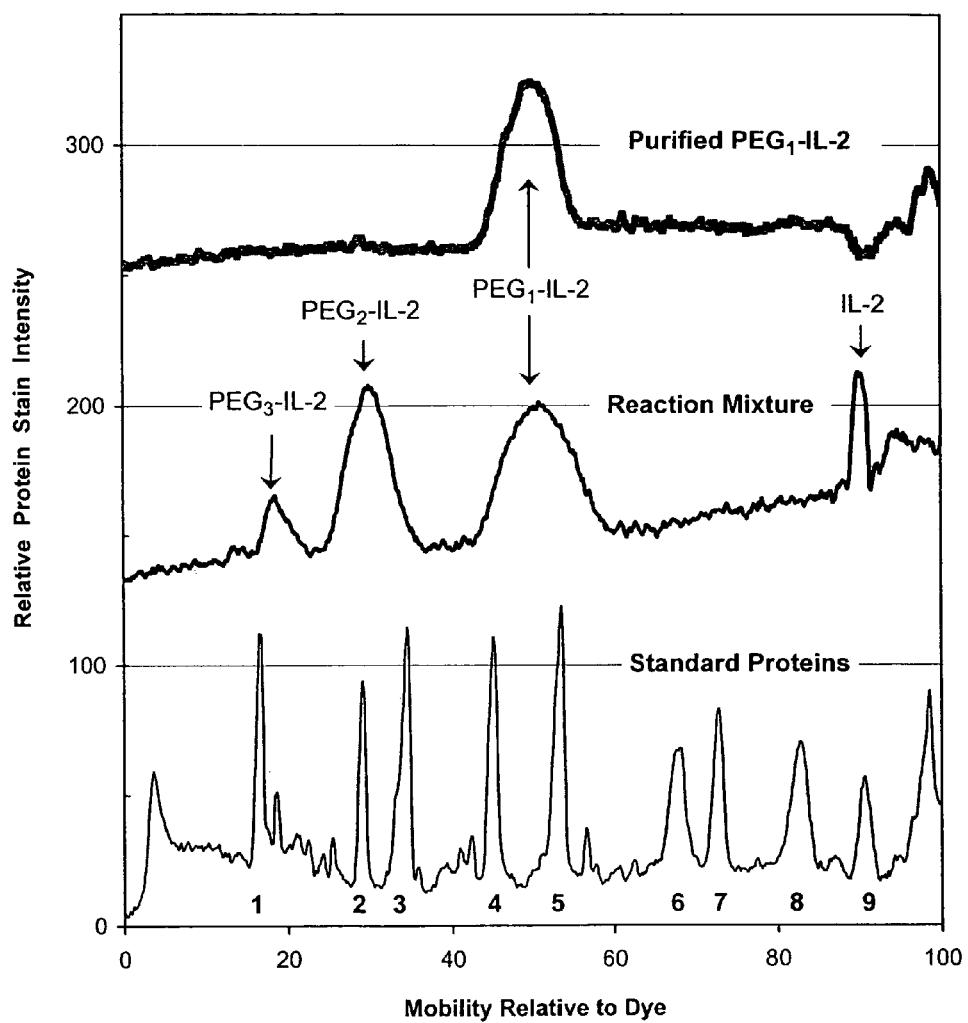

FIG. 13 shows electrophoretic analyses of a reaction mixture of PEGylated interleukin-2 ("PEG-IL-2") and of a fraction from the cation-exchange column for which the chromatogram is shown in FIG. 11.

Figure 14:
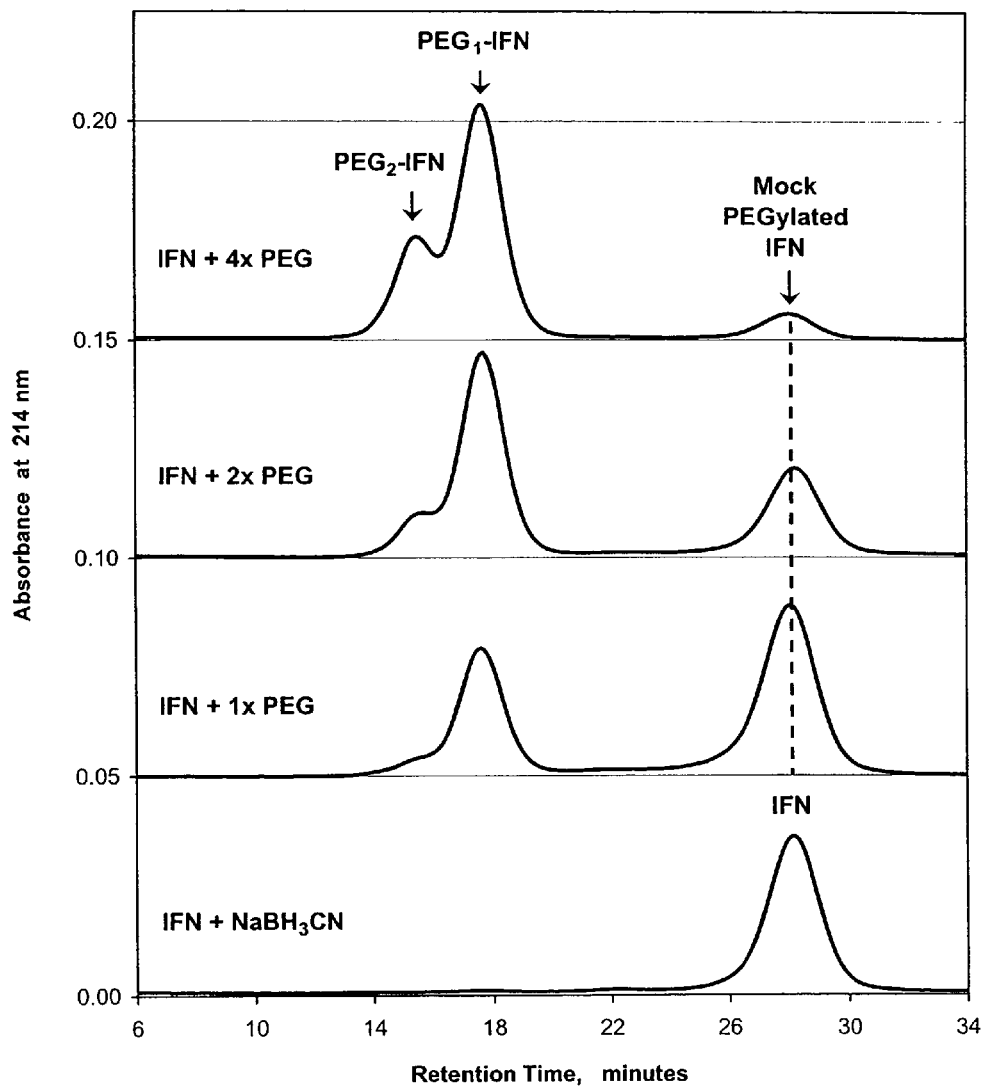

FIG. 14 depicts the resolution by size-exclusion HPLC of interferon-β-1b ("IFN") from its conjugates formed by reductive alkylation with 20 kDa mPEG aldehyde at various input concentrations ("1×," "2×" or "4×"), with sodium cyanoborohydride ($NaBH_3CN$) as the reducing agent. Conjugates containing one strand of PEG ("$PEG_1$-IFN") or two strands ("$PEG_2$-IFN") are resolved from IFN to which PEG was not coupled under these conditions ("Mock PEGylated IFN").

Figure 15:
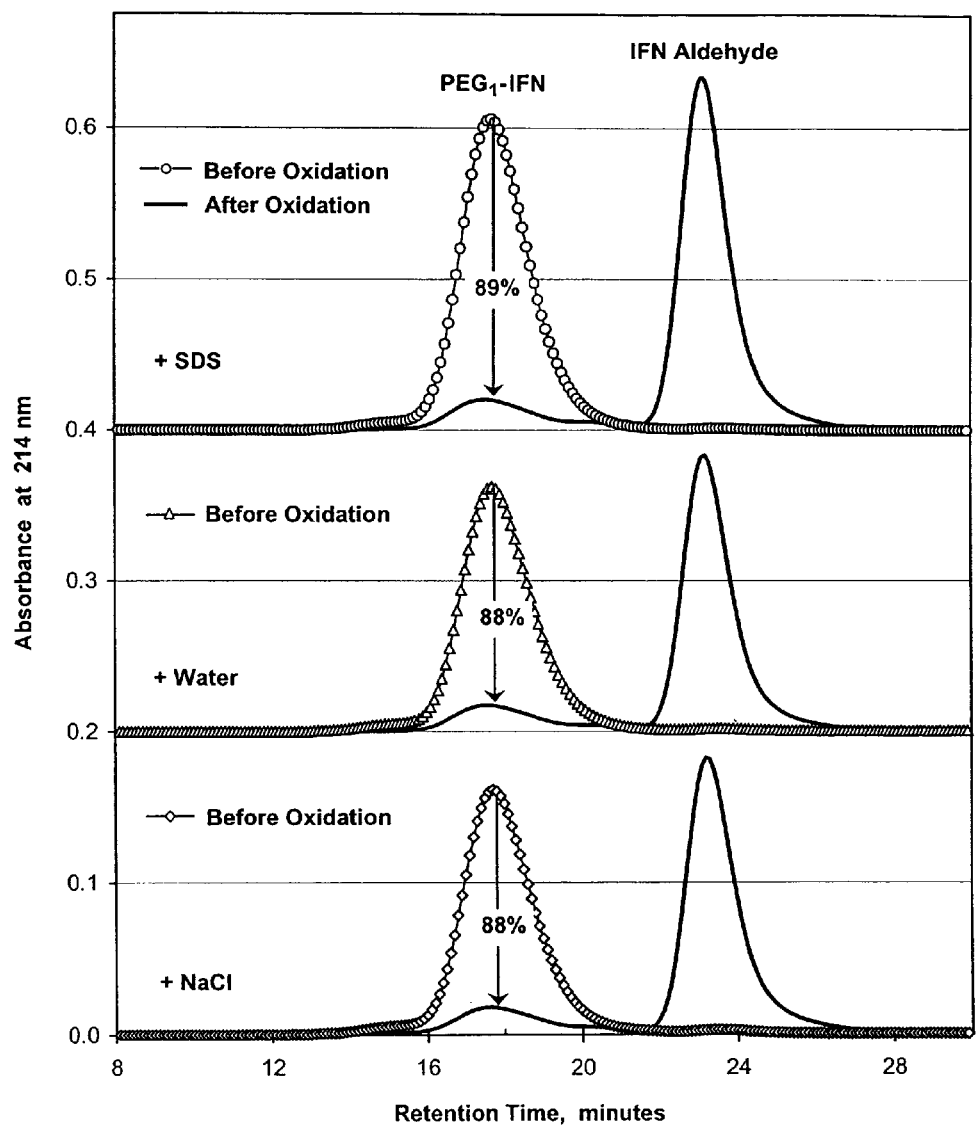

FIG. 15 demonstrates the oxidative cleavage by sodium periodate of about 90% of $PEG_1$-IFN-β synthesized by reductive alkylation under various conditions. Size-exclusion HPLC in the presence of sodium dodecyl sulfate ("SDS") resolved the residual $PEG_1$-IFN-β from the cleavage products, including formaldehyde and IFN in which the N-terminal serine was cleaved to an aldehyde ("IFN Aldehyde").

Figure 16:
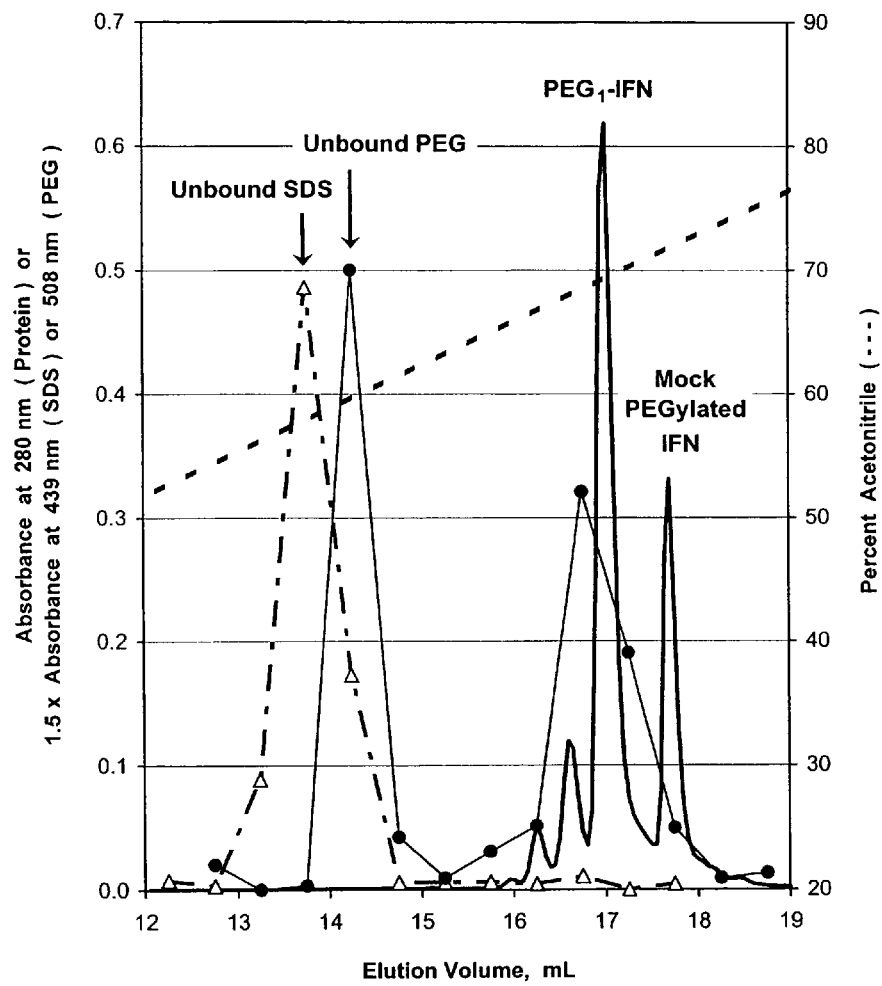

FIG. 16 depicts the resolution by reversed phase chromatography of $PEG_1$-IFN-β from Mock PEGylated IFN-β, unbound PEG, unbound SDS and minor components of the reaction mixture.

Figure 17:
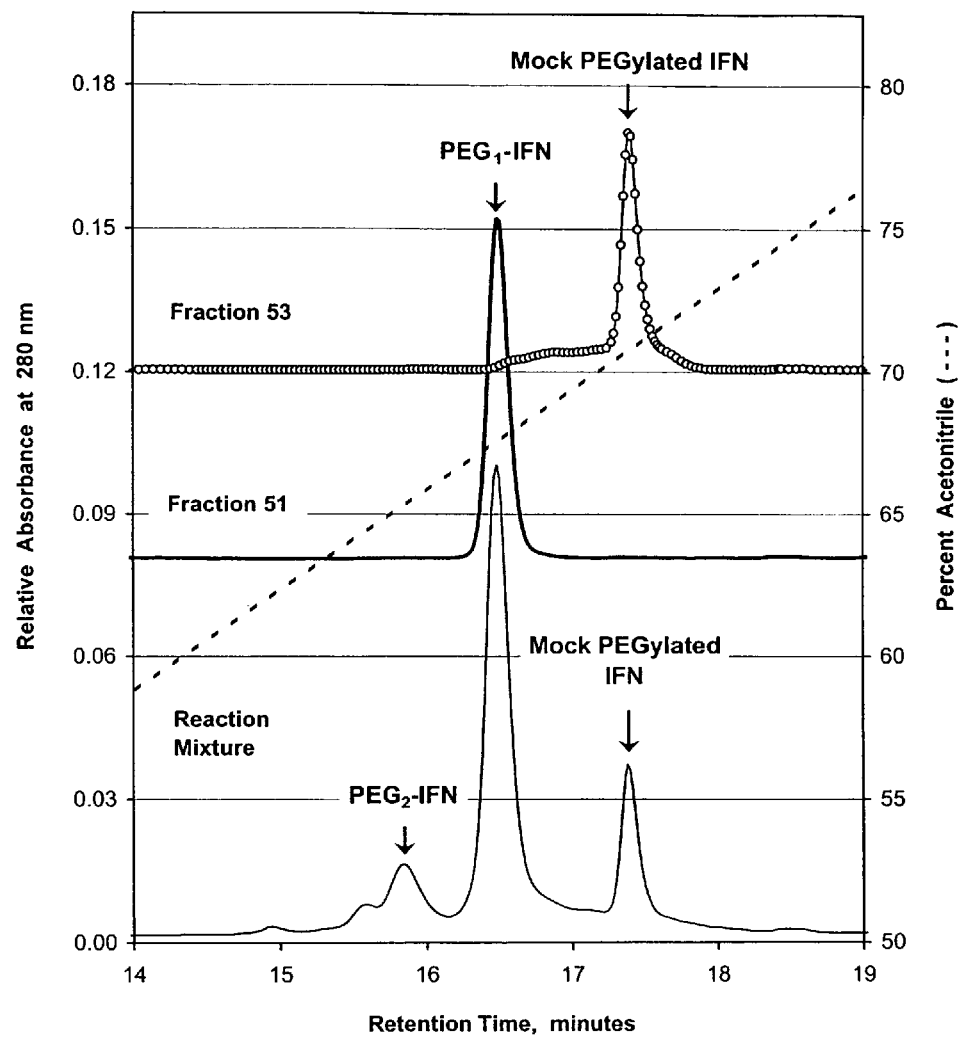

FIG. 17 depicts results of analytical reversed phase ("RP") chromatography of a PEGylation reaction mixture and fractions from a preparative RP column that were enriched in $PEG_1$-IFN-β (Fraction 51) or in Mock PEGylated IFN-β (Fraction 53), respectively.

Figure 18:
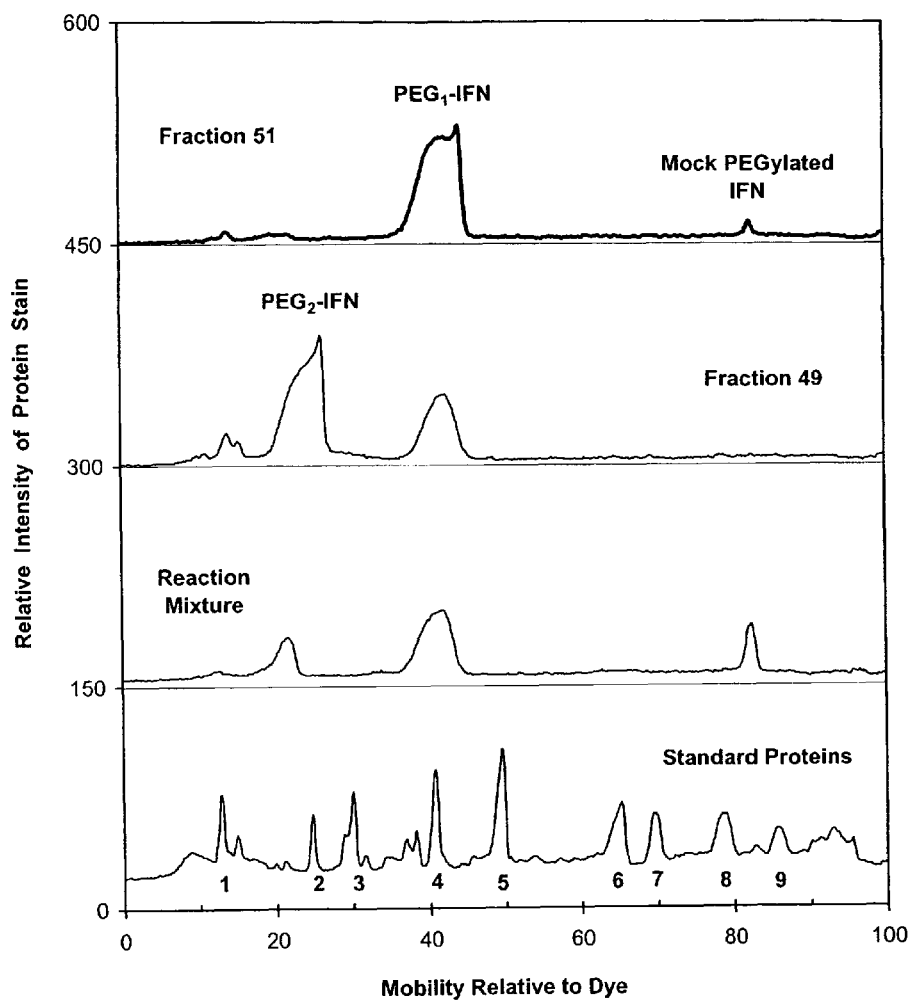

FIG. 18 depicts results of electrophoretic analyses of a PEGylation reaction mixture and fractions from a preparative RP column that are enriched either in $PEG_1$-IFN-β (Fraction 51) or in conjugates containing more than one strand of PEG (Fraction 49). The gel was stained for protein with a fluorescent dye and photographed with ultraviolet illumination. The intensity of the stain was measured with Kodak 1D imaging software.

Figure 19:
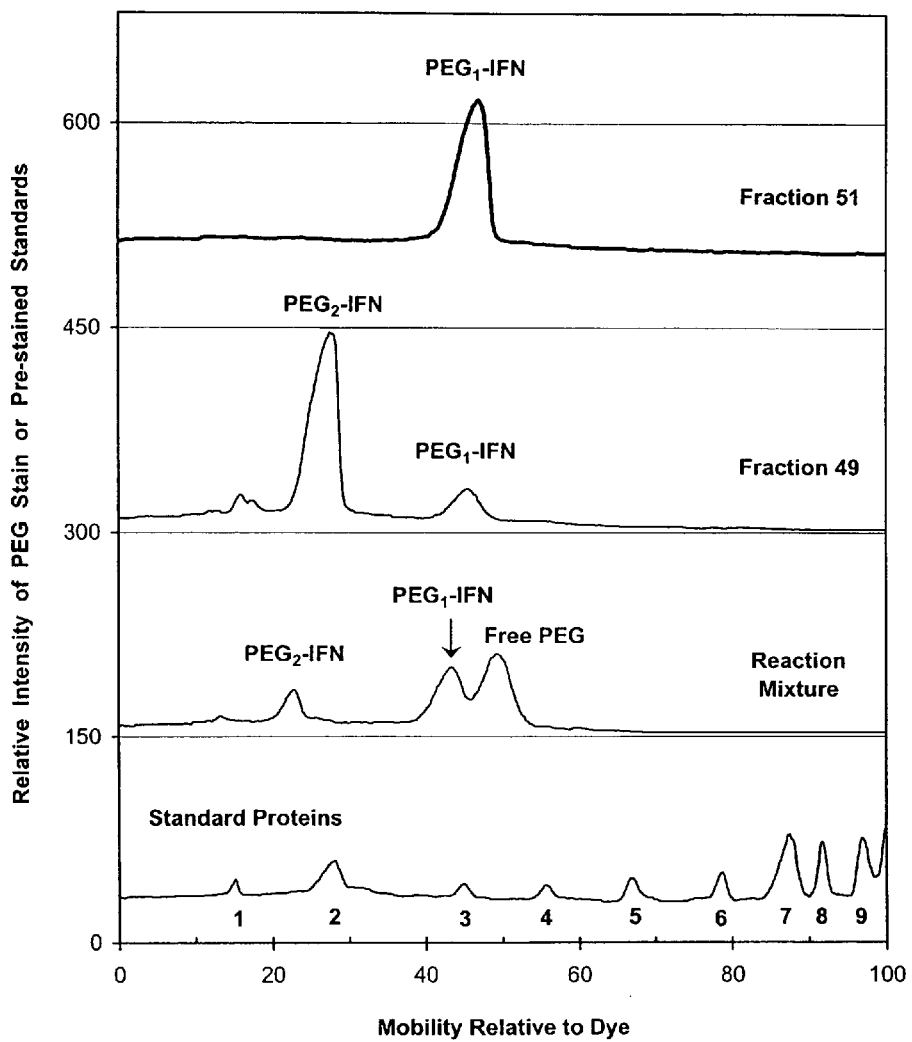

FIG. 19 depicts results of electrophoretic analyses of the same samples as in FIG. 18, except that the gel was stained for PEG with a reagent containing $BaCl_2$, $I_2$ and KI. The intensity of the stain in a photograph of the gel was measured as in FIG. 18. A peak of residual free 20-kDa PEG is detectable in the reaction mixture.

Figure 20:
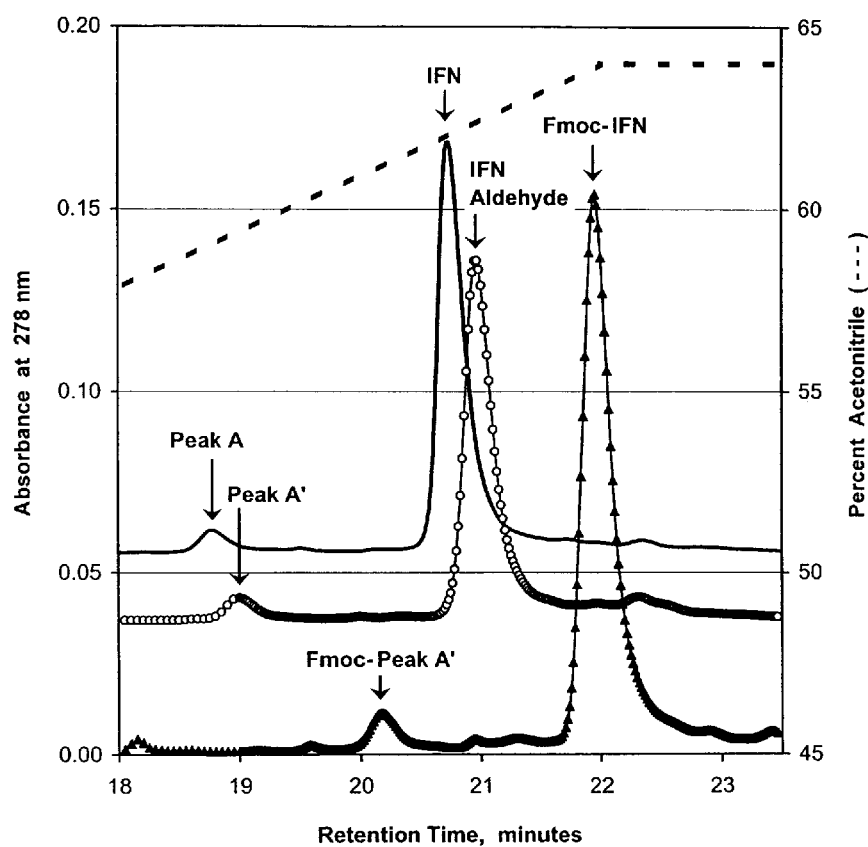

FIG. 20 depicts reversed phase chromatograms of samples of IFN-β-1b that were either untreated (top curve) or incubated with 0.5 mM $NaIO_4$, which cleaved the N-terminal serine residues of both the major and minor components to aldehyde derivatives (middle curve), or oxidized with $NaIO_4$ and reacted with 9-fluorenylmethyl carbazate ("Fmoc-carbazate"). The minor component ("Peak A") contains an oxidized methionine residue. The similar increases in the retention times of both Peak A and the major component after oxidation reflect the cleavage of the N-terminal serine residues in each peak to an aldehyde. No increase in the percentage of Peak A was detected after incubation with $NaIO_4$ under these conditions. The formation of Fmoc conjugates from the oxidized forms of Peak A and the main component is indicated by the increases in their retention times and absorbances after reaction with Fmoc-carbazate.

Figure 21:
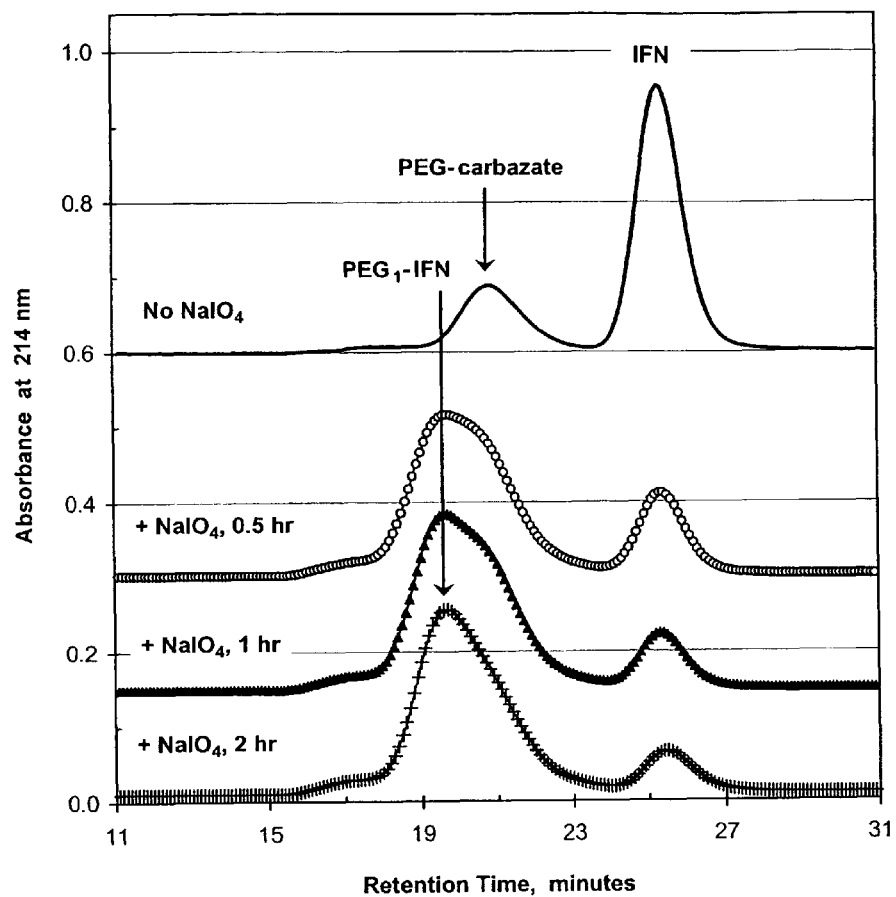

FIG. 21 demonstrates the synthesis of $PEG_1$-IFN-β by the reaction of 20-kDa PEG-carbazate with the aldehyde derivative of IFN-β. The increasing proportion of the conjugate detected after incubation of the protein with 0.125 mM $NaIO_4$ at room temperature for 0.5, 1 or 2 hours indicates that complete conversion of the N-terminal serine to an aldehyde requires more than 1 hour under these conditions. $PEG_1$-IFN-β was incompletely resolved from 20-kDa PEG-carbazate on this size-exclusion column.

Figure 22:
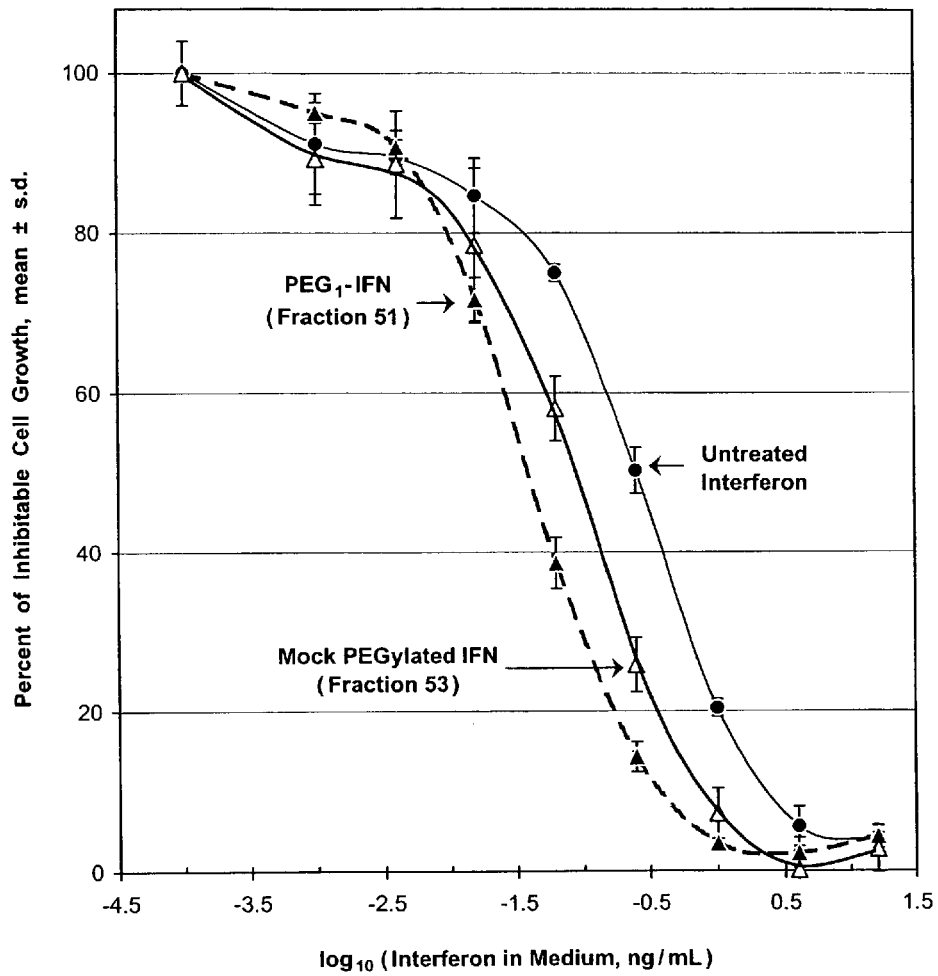

FIG. 22 demonstrates the greater antiproliferative potency on human Burkitt's lymphoma cells (Daudi cells) of dilutions of $PEG_1$-IFN-β, which was purified by reversed phase chromatography (Fraction 51, characterized in FIGS. 17-19), than that of dilutions of the stock solution of IFN-β. The concentration of purified $PEG_1$-IFN-β required to inhibit 50% of the inhibitable growth of these cells was about 40 pg/mL, which was about one sixth of that required for the stock solution of IFN-β. The concentration of purified Mock PEGylated IFN-β (Fraction 53 from the reversed phase chromatogram shown in FIG. 17) required to inhibit 50% of the inhibitable growth of these cells was about 80 pg/mL, which is about one third of that required for the stock solution of IFN-β.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described hereinafter.

DEFINITIONS

About: As used herein when referring to any numerical value, the term "about" means a value of +10% of the stated value (e.g., "about 50° C." encompasses a range of temperatures from 45° C. to 55° C., inclusive; similarly, "about 100 mM" encompasses a range of concentrations from 90 mM to 110 mM, inclusive).

Amino Acid Residue: As used herein, the term "amino acid residue" refers to a specific amino acid, usually dehydrated as a result of its involvement in two peptide bonds, in a polypeptide backbone or side chain, but also when the amino acid is involved in one peptide bond, as occurs at each end of a linear polypeptide chain. The amino acid residues are referred to by the three-letter codes or single-letter codes that are common in the art.

Antagonist: As used herein, the term "antagonist" refers to a compound, molecule, moiety or complex that reduces, substantially reduces or completely inhibits the biological and/or physiological effects of a given cytokine on a cell, tissue or organism that are mediated through the receptors for the given cytokine. Antagonists may carry out such effects in a variety of ways, including but not limited to competing with the agonist for binding site(s) or receptor(s) on the cell surface; interacting with the agonist in such a way as to reduce, substantially reduce or completely inhibit the ability of the agonist to bind to cell surface receptors; binding to and inducing a conformational change in cell surface receptors such that the receptors assume a structure to which the agonist can no longer bind (or can bind only with reduced or substantially reduced affinity and/or efficiency); inducing a physiological change (e.g., increase in intracellular signaling complexes; increase in transcriptional inhibitors; reduction in cell surface ligand receptor expression; etc.) in cells, tissues or organisms such that the binding of the agonist, or the physiological signal induced by the agonist upon binding to the cell, is reduced, substantially reduced or completely inhibited; and other mechanisms by which antagonists may carry out their activities, that will be familiar to the ordinarily skilled artisan. As the ordinarily skilled artisan will understand, an antagonist may have a similar structure to the ligand that it antagonizes (e.g., the antagonist may be a mutein, variant, fragment or derivative of the agonist), or may have a wholly unrelated structure.

Bioactive Component: As used herein, the term "bioactive component" refers to a compound, molecule, moiety or complex that has a particular biological activity in vivo, in vitro or ex vivo upon a cell, tissue, organ or organism, and that is capable of being bound to one or more polyalkylene glycols to form the conjugates of the invention. Preferred bioactive components include, but are not limited to, proteins and polypeptides such as those that are described herein.

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, thioester, thioether, urethane, amide, amine, peptide, imide, hydrazone, hydrazide, carbon-sulfur bonds, carbon-phosphorus bonds, and the like. The term "bound" is broader than and includes terms such as "coupled," "conjugated" and "attached."

Conjugate/conjugation: As used herein, "conjugate" refers to the product of covalent attachment of a polymer, e.g., PEG or PEO, to a bioactive component, e.g., a protein or glycoprotein. "Conjugation" refers to the formation of a conjugate as defined in the previous sentence. Any method normally used by those skilled in the art of conjugation of polymers to biologically active materials can be used in the present invention.

Coupled: The term "coupled", as used herein, refers to attachment by covalent bonds or by strong non-covalent interactions, typically and preferably to attachment by covalent bonds. Any method normally used by those skilled in the art for the coupling of biologically active materials can be used in the present invention.

Cytokine: As used herein, the term "cytokine" is defined as a secreted regulatory protein that controls the survival, growth, differentiation, and/or effector function of cells, in endocrine, paracrine or autocrine fashion (reviewed in Nicola, N. A., supra; Kossiakoff, A. A., et al., (1999) *Adv Protein Chem* 52:67-108). According to this definition, cytokines include interleukins, colony-stimulating factors, growth factors, and other peptide factors produced by a variety of cells, including but not limited to those specifically disclosed or exemplified herein. Like their close relatives, the polypeptide hormones and growth factors, cytokines initiate their regulatory functions by binding to specific receptor proteins on the surface of their target cells.

Disease, disorder, condition: As used herein, the terms "disease" or "disorder" refer to any adverse condition of a human or animal including tumors, cancer, allergies, addiction, autoimmunity, infection, poisoning or impairment of optimal mental or bodily function. "Conditions" as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood by those of ordinary skill in the art.

Effective Amount: As used herein, the term "effective amount" refers to an amount of a given conjugate or composition that is necessary or sufficient to realize a desired biologic effect. An effective amount of a given conjugate or composition of the present invention would be the amount that achieves this selected result, and such an amount can be determined as a matter of routine by a person skilled in the art, using assays that are known in the art and/or that are described herein, without the need for undue experimentation. For example, an effective amount for treating an immune system deficiency could be that amount necessary to cause activation of the immune system, resulting in the development of an antigen-specific immune response upon exposure to an antigen. The term is also synonymous with "sufficient amount." The effective amount for any particular application can vary depending on such factors as the disease or condition being treated, the particular composition being administered, the route of administration, the size of the subject, and/or the severity of the disease or condition. One of ordinary skill in the art can determine empirically the effective amount of a particular conjugate or composition of the present invention without necessitating undue experimentation.

One, a, or an: When the terms "one," "a," or "an" are used in this disclosure, they mean "at least one" or "one or more," unless otherwise indicated.

PEG: As used herein, "PEG" includes all polymers of ethylene oxide, whether linear or branched or multi-armed and whether end-capped or hydroxyl terminated. "PEG" includes those polymers that are known in the art as poly (ethylene glycol), methoxypoly(ethylene glycol) or mPEG or poly(ethylene glycol)-monomethyl ether, alkoxypoly(ethylene glycol), poly(ethylene oxide) or PEO, α-methyl-ω-hydroxy-poly(oxy-1,2-ethanediyl) and polyoxirane, among other names that are used in the art for polymers of ethylene oxide.

PEGylation, PEGylated and Mock PEGylated: As used herein, "PEGylation" refers to any process for the covalent coupling of PEG to a bioactive target molecule, especially a receptor-binding protein. The conjugate produced thereby is referred to as being "PEGylated." As used herein, "Mock PEGylated" refers to the portion of the protein in a PEGylation reaction mixture to which no PEG has been covalently attached. Nevertheless, the Mock PEGylated product may have been altered during the reaction or subsequent purification steps, e.g., as a consequence of exposure to the reducing agent during PEGylation by reductive alkylation and/or by having one or more inhibitory agents, compounds, etc., removed during the processing and/or purification steps.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. This term is also intended to refer to the products of post-expression modifications of the polypeptide, for example, glycosylation, hyperglycosylation, acetylation, phosphorylation and the like. A polypeptide may be derived from a natural biological source or produced by recombinant DNA technology, but is not necessarily translated from a designated nucleic acid sequence. It may be generated in any manner, including by chemical synthesis.

Protein and glycoprotein: As used herein, the term protein refers to a polypeptide generally of a size of above about 10 or more, 20 or more, 25 or more, 50 or more, 75 or more, 100 or more, 200 or more, 500 or more, 1,000 or more, or 2,000 or more amino acids. Proteins generally have a defined three-dimensional structure, although they do not necessarily have such structure, and are often referred to as folded, as opposed to peptides and polypeptides, which often do not possess a defined three-dimensional structure, but rather can adopt a large number of different conformations, and are referred to as unfolded. Peptides may, however, also have a defined three-dimensional structure. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

Remote: As used herein, the term "remote" (as in "remote N-terminal amino acid" or "remote glycosylation site") refers to a structure in which the location of one or more attachment sites for one or more polymers on a protein is/are distal to or spatially removed from one or more receptor-binding regions or domains of the protein, as assessed by molecular modeling. Conjugation of a polymer at such a remote attachment site (usually the N-terminal amino acid (for receptor-binding proteins that are therefore referred to as "remote N-terminal" or "RN" receptor-binding proteins) or one or more carbohydrate moieties or glycosylation sites on a glycoprotein (for receptor-binding proteins that are therefore referred to as "remote glycosylation" or "RG" receptor-binding proteins)) does not cause substantial steric hindrance of the binding of the protein to its receptor(s). Hence, an amino-terminal amino acid or a glycosylation site on a cytokine is said to be "located remotely from one or more receptor-binding domains" of the cytokine when conjugation (e.g., covalent attachment) of a water-soluble polymer to the amino-terminal amino acid or glycosylation site, respectively, does not interfere substantially with the ability of the cytokine to bind to its receptor(s), particularly to cell-surface receptors. It is recognized, of course, that a given cytokine may contain more than one receptor-binding domain. In such situations, an amino-terminal amino acid or glycosylation site of a cytokine can be located remotely from one such domain or from more than one of such domains, and still be considered to be "located remotely from one or more receptor-binding domains," so long as conjugation of the amino-terminal amino acid or glycosylation site does not interfere substantially with the binding of the cytokine to its receptor(s) via one or more of the receptor-binding domains. Whether or not the conjugation interferes substantially with the ability of a protein to bind to its receptor(s) can be readily determined using art-known assays of ligand-receptor binding that will be familiar to the ordinarily skilled artisan.

Figure 1A:
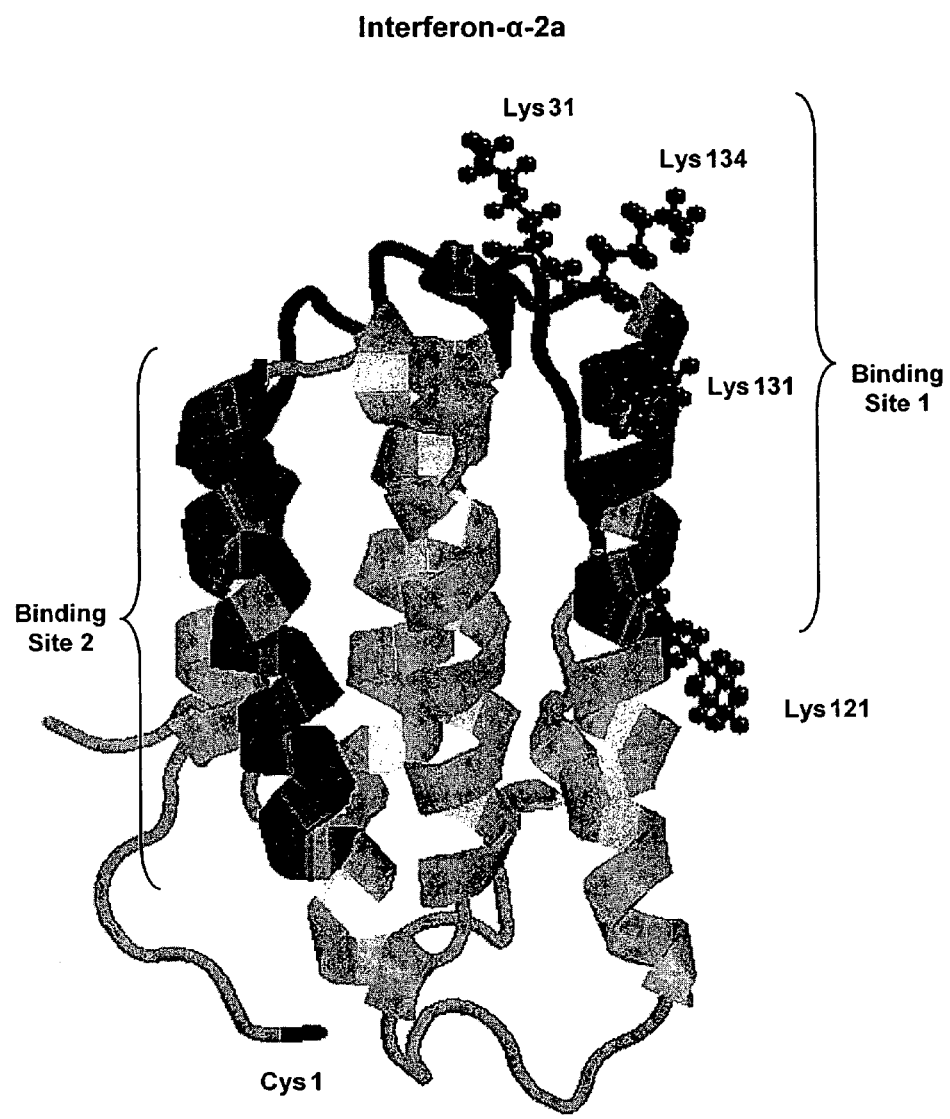
FIG. 1a shows a model of interferon-alpha-2a, in which the four lysine residues (Lys 31, Lys 121, Lys 131 and Lys 134) that are reported to be the primary sites of PEGylation in Roche's PEG-interferon product, PEGASYS®, are shown in "ball-and-stick" format (based on data of Bailon, P., et al., supra). The regions involved in binding to its receptors ("Binding Sites 1 and 2") are identified. All four of the lysine residues that are reported to be PEGylated in Pegasys are in the region of Binding Site 1. (PDB code 1ITF)
Figure 1B:
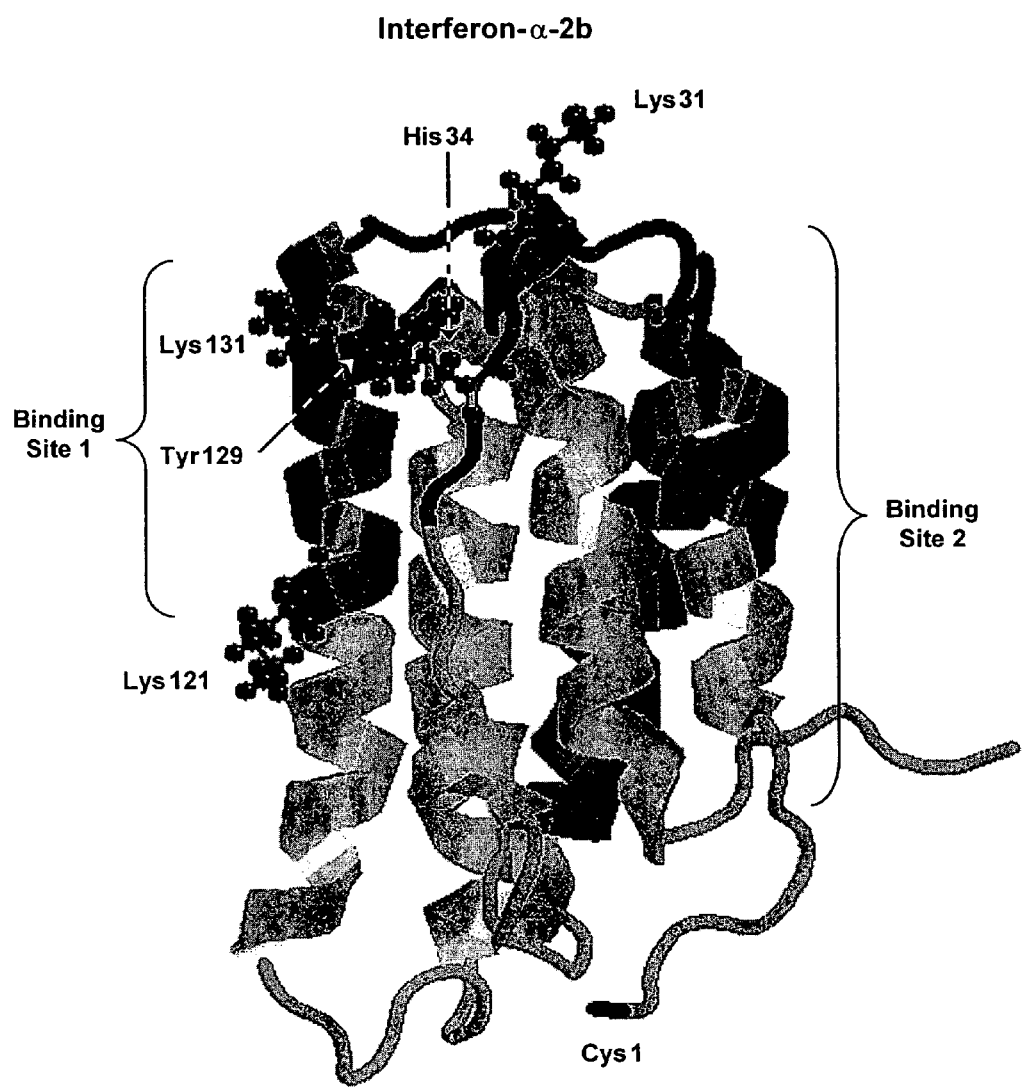
FIG. 1b shows a model of interferon-alpha-2b, in which the residues that are reported to be the major sites of PEGylation in Schering-Plough's PEG-INTRON® (His 34, Lys 31, Lys 121, Tyr 129 and Lys 131) are shown in "ball-and-stick" format (based on data of Wylie, D. C., et al., supra). These amino acid residues are in the region of Binding Site 1.
Figure 1C:
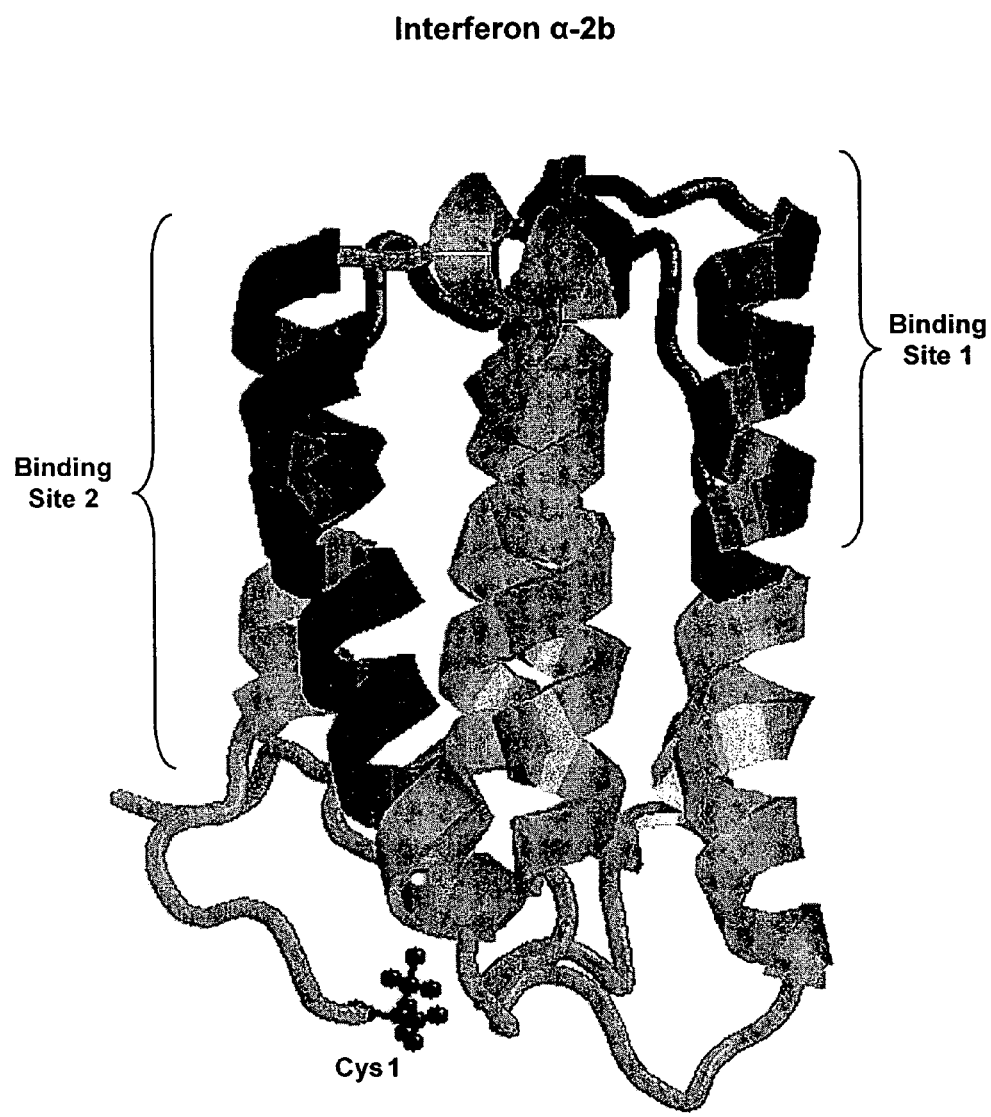
FIG. 1c shows a model of interferon-alpha-2b, in which the amino-terminal cysteine residue ("Cys 1"), a target of PEGylation according to the present invention, is shown in "ball-and-stick" format. Cys 1 is remote from Binding Sites 1 and 2.
Figure 1D:
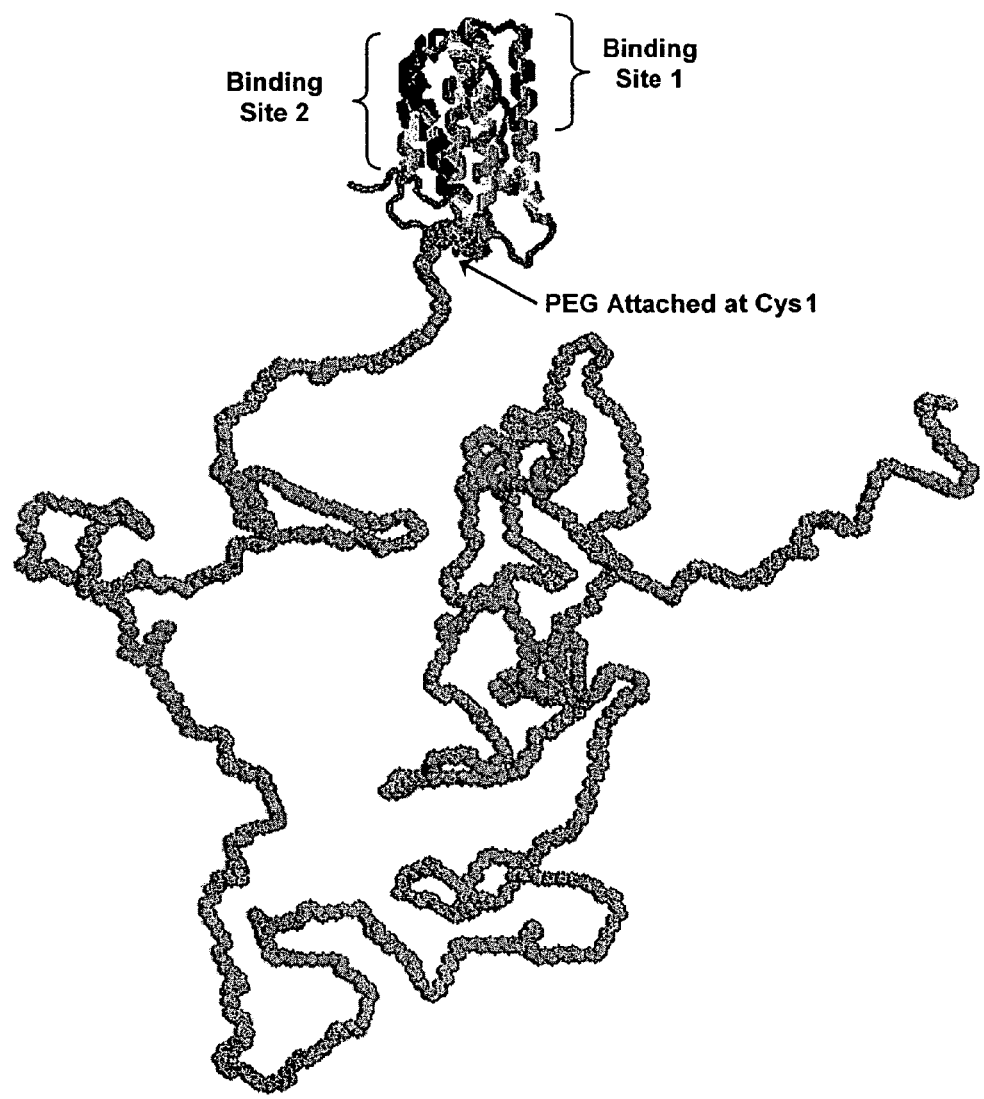
FIG. 1d shows the same model of interferon-alpha-2b as that shown in FIG. 1c, to which a single strand of 20-kDa PEG has been attached at the N-terminal cysteine residue ("Cys 1"). The structure of PEG was generated using an adaptation of the program described by Lee, L. S., et al., (1999) *Biocon-jug Chem* 10:973-981) and is rendered to the same scale as is the protein.

As shown in FIG. 1d of this specification, PEG is a highly extended and flexible polymer that occupies a large volume in solution relative to a protein of similar molecular weight. Although the amino acid residue to which PEG is attached may be remote from one or more receptor-binding sites, portions of the polymer could, nevertheless, interfere, to some extent, with receptor binding. The probability of such interference increases with the molecular weight and hence the volume occupied by the polymer in solution. In any case, targeted attachment of PEG to one or more site(s) remote from the receptor-binding region(s) will interfere less with the function of the cytokine than random PEGylation.

Methods of assessing ligand-receptor binding include, without limitation, competitive binding assays, radioreceptor binding assays, cell-based assays, surface plasmon resonance measurements, dynamic light scattering, ultracentrifugation and ultrafiltration.

Substantial, substantially: As used herein, conjugation of a protein is said not to interfere "substantially" with the ability of the protein to bind to its receptor(s) if the rate and/or amount of binding of a conjugated protein to a receptor is not less than about 40%, about 50%, about 60%, about 65%, about 70%, about 75%, about 80%, about 85%, about 90%, about 91%, about 92%, about 93%, about 94%, about 95%, about 96%, about 97%, about 98%, about 99% or about 100% or more, of the binding rate and/or amount of the corresponding cytokine that has not been conjugated.

Treatment: As used herein, the terms "treatment," "treat," "treated" or "treating" refer to prophylaxis and/or therapy. When used with respect to an infectious disease, for example, the term may refer to a prophylactic treatment that increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., to reduce or eliminate the infection or to prevent it from becoming worse.

Overview

The present invention provides methods for the synthesis of polymer conjugates of receptor-binding proteins that retain unexpectedly high receptor-binding activity relative to polymer conjugates of the same receptor-binding protein in which one or more polymers are attached randomly. Through the use of x-ray crystallographic and nuclear magnetic resonance-based structural analyses, mutational analysis and molecular modeling software, the present inventors have identified target sites for PEGylation of cytokines that are involved or are not involved in binding to their receptors. As a class of proteins, these cytokines are referred to herein as receptor-binding proteins. By selection of a synthetic strategy that targets polymer attachment to the region(s) of receptor-binding proteins that are not involved in receptor interactions, certain undesirable steric hindrances are avoided and the resultant polymer conjugates retain unusually high potency. Those receptor-binding proteins that have an amino-terminal residue that is remote from one or more of their receptor-binding regions or domains are defined herein as "remote N-terminal" or "RN" receptor-binding proteins; they include all cytokines or antagonists thereof that have their amino-terminal amino acid located remotely from the receptor-binding site or sites of the protein.

In additional embodiments of the invention, conjugates are produced comprising one or more synthetic polymers (e.g., one or more poly(ethylene glycols)) covalently coupled to cytokines that have natural glycosylation sites that are remote from one or more of their receptor-binding regions or domains. According to this aspect of the invention, the bioactive components (e.g., cytokines) of the conjugates will display well-preserved receptor-binding activities when synthetic polymers are coupled in the region of the glycosylation site(s). This subset of receptor-binding proteins is referred to herein as "RG" receptor-binding proteins. When a hydrophilic or amphipathic polymer is coupled selectively at or near such a "remote glycosylation" site, especially when the target protein is a non-glycosylated form of a protein that is naturally glycosylated, the polymer can mimic the favorable effects of the naturally occurring carbohydrate, e.g., on aggregation, stability and/or solubility. Hence attachment of the polymer at or near a glycosylation site is referred to herein as "pseudoglycosylation." Thus, the present invention provides methods for the synthesis of conjugates in which the site-selective coupling of a synthetic polymer effectively replaces the naturally occurring carbohydrate moieties. The resultant pseudoglycosylation contributes to improved solubility, decreased aggregation and retarded clearance from the bloodstream, compared to other nonglycosylated forms of the protein. This approach therefore is particularly advantageous for preparing conjugates and compositions of proteins that are produced by recombinant DNA technology in prokaryotic host cells (e.g., bacteria such as *Escherichia coli*), since prokaryotic organisms generally do not glycosylate proteins that they express.

Analogously, selective PEGylation of the carbohydrate moiety of a glycoprotein can result in "pseudohyperglycosylation" of the glycoprotein. This process was described, for example, by C. Bona et al., in PCT Publication No. WO 96/40731, the disclosure of which is incorporated herein by reference in its entirety. This approach therefore is particularly advantageous for preparing conjugates and compositions of proteins that are produced by recombinant DNA technology in eukaryotic host cells (e.g., in yeasts, plant cells and animal cells (including mammalian and insect cells), since eukaryotic organisms generally do glycosylate proteins that they express, if those proteins include naturally occurring glycosylation signals or glycosylation signals introduced by recombinant DNA technology. Such pseudoglycosylated and pseudohyperglycosylated RG receptor-binding proteins are within the scope of the present invention.

The invention thus also encompasses polymer conjugates of "RN" receptor-binding proteins that retain substantial, nearly complete or essentially complete receptor-binding activity and pseudoglycosylated or pseudohyperglycosylated "RG" receptor-binding proteins that retain substantial, nearly complete or essentially complete receptor-binding activity. As used herein, a cytokine is said to "retain substantial, nearly complete or essentially complete receptor-binding activity" when conjugated with one or more water-soluble polymers according to the present invention, if the conjugation of the cytokine does not interfere substantially with the ability of the protein to bind to its receptor(s), i.e., if the rate and/or amount of binding of the conjugated protein to its corresponding receptor(s) is not less than about 40%, about 50%, about 60%, about 65%, about 70%, about 75%, about 80%, about 85%, about 90%, about 91%, about 92%, about 93%, about 94%, about 95%, about 96%, about 97%, about 98%, about 99% or about 100% or more, of the binding rate and/or amount of an unconjugated form of the corresponding protein. Also included within the scope of the present invention are polymer conjugates of those receptor-binding proteins that are classified as both "RN" and "RG" receptor-binding proteins. Two examples of the latter proteins are interferon beta (particularly interferon-beta-1b) and IL-2.

In additional embodiments, the invention provides methods for the synthesis of polymer conjugates of receptor-binding proteins that retain unexpectedly high receptor-binding activity relative to polymer conjugates of the same receptor-binding protein in which one or more polymers are attached randomly. The invention also provides conjugates produced by such methods, and compositions comprising one or more of these conjugates of the invention that may further comprise one or more additional components or reagents, such as one or more buffer salts, one or more carbohydrate excipients, one or more carrier proteins, one or more enzymes, one or more detergents, one or more nucleic acid molecules, one or more polymers such as unconjugated PEG or polyalkylene glycol, and the like. The invention also provides kits comprising the conjugates and/or compositions of the invention.

The invention also provides pharmaceutical or veterinary compositions comprising the conjugates of the invention and at least one excipient or carrier that is acceptable for pharmaceutical or veterinary use. The invention also provides methods of treating or preventing a variety of physical disorders using such compositions, comprising administering an effective amount of one or more of the conjugates or compositions of the present invention to an animal suffering from or predisposed to a physical disorder or condition.

Further, the invention provides stabilized receptor-binding proteins and methods for their production for use in industrial cell culture, whereby unexpectedly high potencies are obtained as a result of the combined effects of substantial retention of bioactivity and increased duration of action in industrial use. The unusually high potencies of the conjugates of the present invention may be reflected in unusually high biomass production, unusually high levels of expression of recombinant proteins and other improvements in efficiencies of bioprocessing.

In additional embodiments, the invention provides alternative methods for increasing the biological potency of a preparation of interferon-beta, particularly a preparation of interferon-beta-1b. Methods according to this aspect of the invention may comprise, for example, removal of one or more inhibitory components from a preparation of interferon-beta (or interferon-beta-1b). According to this aspect of the invention, the one or more inhibitory components can be removed from the preparations by a variety of art-known methods of protein and peptide processing, purification and/or analysis, including but not limited to one or more chromatographic methods such as size-exclusion chromatography, reversed phase chromatography, hydrophobic interaction chromatography and affinity chromatography. As a practical matter, the determination of the biological potency of a given preparation of interferon-beta (i.e., whether the biological potency is increased, decreased or unaffected, relative to a stock solution of a cytokine such as interferon-beta) can be accomplished by any number of in vitro or in vivo assays that will be familiar to the ordinarily skilled artisan. For example, a cell culture assay that responds to interferon-beta can be used to determine the biological potency of interferon-beta preparations. Non-limiting examples of suitable such cell culture assays include antiproliferative assays, antiviral assays, signal transduction assays and gene activation assays, examples of which are well-known to those of ordinary skill in the art.

In related embodiments, the invention also provides methods for determining the amount of a polymer that is attached to the amino terminus of a protein having an N-terminal serine residue, in a polymer-protein conjugate synthesized by reductive alkylation. Methods according to this aspect of the invention comprise, for example, (a) reacting the conjugate with a sufficient quantity of an oxidizing agent for a sufficient time to cleave the polymer from the serine residue of the protein; and (b) measuring the increase in the portion of unconjugated protein in the preparation. Proteins suitable for use in accordance with such methods include, but are not limited to, cytokines (including interferon-beta (particularly interferon-beta-1b, which preferably has the amino acid sequence specified in SEQ ID NO:1) and megakaryocyte growth and development factor (Guerra, P. I., et al., (1998) *Pharm Res* 15:1822-1827, the disclosure of which is incorporated herein by reference in its entirety). The oxidizing agent used in certain such methods of the invention may be a periodate including, but not limited to, sodium metaperiodate, potassium metaperiodate, lithium metaperiodate, calcium periodate, barium periodate and periodic acid. Suitable methods for measuring the increase in the portion of unconjugated protein in the preparation include any variety of art-known methods of protein and peptide analysis, including, for example, size-exclusion chromatography, reversed phase chromatography, gel electrophoresis, capillary electrophoresis, ultracentrifugation, ultrafiltration, light scattering and mass spectroscopy.

In additional related embodiments, the invention provides methods for the selective oxidative cleavage of an N-terminal serine residue of a bioactive protein without oxidizing functionally essential amino acid residues of said bioactive protein. Certain such methods of the invention comprise, for example, (a) adjusting the hydrogen ion concentration of a solution of the bioactive protein to a pH of between about 5 and about 10, more preferably a pH of between about 7 and about 8; (b) mixing the solution of bioactive protein with about 0.1 moles to about 10 moles, or more preferably with about 0.5 moles to about 5 moles, of a periodate per mole of bioactive protein; and (c) incubating said mixture for at least one hour, preferably at a temperature of between about 2° C. and about 40° C. Proteins suitable for use in accordance with such methods include, but are not limited to, cytokines (including interferon-beta (particularly interferon-beta-1b, which preferably has the amino acid sequence specified in SEQ ID NO: 1).

Methods

The present inventors have discovered that targeting of polymers to the amino-terminal amino acid of an "RN" receptor-binding protein or to the vicinity of the glycosylation site of an "RG" receptor-binding protein assures that the polymer is attached at a site that is remote from one or more of the receptor-binding regions or domains of the protein, thereby minimizing steric hindrance of receptor interactions by the attached polymer molecules. Consequently, a higher percentage of the receptor-binding activity can be preserved by conjugating proteins according to the methods of the present invention than would occur if the polymer were attached within or proximal to a portion of the molecule that is involved in binding to its receptor(s). This principle, which can result in unexpectedly high retention of receptor binding activity, can be demonstrated for receptor-binding proteins that are selected from among basic fibroblast growth factor ("bFGF" or "FGF-2"), epidermal growth factor ("EGF"), insulin-like growth factor-1 ("IGF-1"), interferon-alpha ("IFN-alpha"), interferon-beta ("IFN-beta," including but not limited to IFN-beta-1b), granulocyte-macrophage-colony stimulating factor ("GM-CSF"), monocyte colony stimulating factor ("M-CSF"), Flt3 ligand, stem cell factor ("SCF"), interleukins 2, 3, 4, 6, 10, 12, 13 and 15, transforming growth factor-beta ("TGF-beta"), human growth hormone ("hGH"), prolactin, placental lactogenic hormone, ciliary neurotrophic factor ("CNTF"), leptin and structural analogs of these receptor-binding-proteins that mimic the actions of these proteins or that are receptor-binding antagonists thereof. In contrast, the selective attachment of a large polymer to the amino terminus of IFN-gamma is not predicted to preserve most of the activity of this cytokine, since such coupling is expected to interfere with binding of the active dimer to its receptors (based on data of Walter, M. R., et al., (1995) *Nature* 376: 230-235).

In a related such embodiment of the invention, polymers are coupled to the amino-terminal residue of muteins of receptor-binding proteins that function as competitive antagonists of the natural protein by binding to one or more of the same receptor(s) without initiating signal transduction. Examples are polymer conjugates of an hGH antagonist that contains the point mutation G12OR (Sundstrom, M., et al., (1996) *J Biol Chem* 271:32197-32203) and an antagonist of prolactin that contains the point mutation G129R (Goffin, V., et al., (1997) *J Mammary Gland Biol Neoplasia* 2:7-17; Chen, W. Y., et al., (1999) *Clin Cancer Res* 5:3583-3593; Chen, W. Y., PCT Publication No. WO 99/58142 A1). Other antagonists of receptor-binding proteins can be produced by selective point mutations, truncations or deletions (see e.g., Tchelet, A., et al., (1997) *Mol Cell Endocrinol* 130:141-152; Peterson, F. C., (1998) *Identification of Motifs Associated with the Lactogenic and Somatotropic Actions of Human Growth Hormone*, Ph.D. Dissertation, Ohio State University, UMI #9822357).

In additional embodiments of the invention, for "RG" receptor-binding proteins, the methods of the present invention result in the attachment of one or more synthetic polymers in proximity to the natural site of attachment of carbohydrate moieties of those receptor-binding proteins that are glycoproteins. This results in "pseudoglycosylation" of these receptor-binding proteins (for example, when they have been expressed by recombinant DNA technology in *E. coli* or other prokaryotic cells that do not perform post-translational glycosylation) or results in "pseudohyperglycosylation" of their glycoprotein forms (for example, for naturally produced glycoproteins or for glycoproteins produced by eukaryotic host cells (e.g., yeasts, plant cells and animal cells (including mammalian and insect cells), that do perform post-translational glycosylation). Examples are polymer conjugates of interferons alpha and beta, as well as of erythropoietin ("Epo") and interleukin-2. The attachment of synthetic polymers at or near the sites of natural glycosylation can be performed by any method that is known in the art, including the mutational method of R. J. Goodson, et al., ((1990) *Biotechnology* 8:343-346) and the method of R. S. Larson, et al., ((2001) *Bioconjug Chem* 12:861-869), which involves prior oxidation of the carbohydrate; the disclosures of these references are incorporated herein by reference in their entireties.

Amino-terminal modification of certain proteins has been disclosed previously (see, e.g. Dixon, H. B. F., (1984) *J Protein Chem* 3:99-108). For example, N-terminal modification of proteins has been reported to stabilize certain proteins against the action of aminopeptidases (Guerra, P. I., et al., supra), to improve the solubility of the protein (Hinds, K., et al., (2000) *Bioconjug Chem* 11:195-201), to decrease the charge on the N-terminal amino group, or to improve the homogeneity of the resulting conjugates (Kinstler, O., et al. European Patent Application No. EP 0 822 199 A2; Kinstler, O., et al., (2002) *Adv Drug Deliv Rev* 54:477-485), among others. An alternative method for coupling polymers to the alpha amino group of an N-terminal cysteine or histidine residue, by an adaptation of a procedure known in the art as "native chemical ligation," has been disclosed (Roberts, M. J., et al., PCT Publication No. WO 03/031581 A2 and U.S. patent application Publication No. 2003/0105224 A1, the disclosures of which are incorporated herein by reference in their entireties). However, the existence of the "RN" and "RG" subclasses of receptor-binding proteins, generally applicable methods for selecting members of those classes, and the preparation and use of polymer conjugates of such receptor-binding proteins as a way to preserve unexpectedly high functional activity of "RN" receptor-binding proteins, have not been recognized or described previously.

Hence, there is an advantage to determining whether or not a given cytokine has an N-terminus and/or glycosylation site(s) that are remote from the receptor-binding site(s) of the ligand. The ability to predict whether a given cytokine is an "RN" or an "RG" ligand, prior to conjugation of the ligand with a polymer, substantially decreases the experimentation required to produce polymer-ligand conjugates (e.g., cytokines or antagonists thereof conjugated with polymers, e.g., PEGs) in which the antigenicity and immunogenicity of the conjugate is reduced relative to the antigenicity and immunogenicity of the unconjugated ligand, while not substantially decreasing the receptor-binding and physiological activities of the conjugated ligand.

Accordingly, in additional embodiments, the present invention provides methods for identifying and selecting receptor-binding protein ligands (e.g., cytokines and antagonists thereof) that have an N-terminus and/or glycosylation site(s) that are remote from the receptor-binding sites of the protein ligands (i.e., methods for identifying and selecting for "RN" or "RG" proteins). In certain such embodiments of the invention, the optimum location for conjugation of one or more polymers (e.g., one or more PEGs) can be determined using molecular modeling, e.g., by viewing the 3-dimensional structure of the protein (cytokine or antagonist thereof) using molecular modeling software to predict the location(s) at which one or more polymers can be attached to the protein without a substantial loss in biological or receptor-binding activity of the protein (see also Schein, C. H., supra). An analogous approach has been demonstrated, for example, for conjugation of PEG to G-CSF in an attempt to improve its resistance to proteolytic digestion (see published U.S. application Ser. No. 2001/0016191 A1 of T. D. Osslund, the disclosure of which is incorporated by reference herein in its entirety). Suitable molecular modeling software for use in the present invention, such as RASMOL (Sayle et al., supra) and other programs used in generating the database of macromolecular structures deposited at the Protein Data Bank (PDB; see Laskowski, R. A., supra), is well-known in the art and will be familiar to those of ordinary skill in the art. Using such molecular modeling software, the three-dimensional structure of a polypeptide, e.g., a cytokine or antagonist thereof, can be predicted or determined with a high degree of confidence, based on crystallographic analyses of the ligands and their receptors. In this way, one of ordinary skill can readily determine which ligands are "RN" or "RG" ligands that are suitable for use in accordance with the present invention.

To practice the present invention, one convenient route for covalently coupling a water-soluble polymer to the alpha amino group of the N-terminal amino acid residue of a protein is by reductive alkylation of Schiff's bases formed with polymers bearing a single aldehyde group, e.g. as claimed by G. P. Royer (U.S. Pat. No. 4,002,531), but not as claimed by J. M. Harris, et al., (U.S. Pat. No. 5,252,714), since the latter inventors claim only polymers derivatized at both ends with aldehyde groups, which are cross-linking agents and are therefore ill-suited to the synthesis of long-acting receptor-binding proteins that retain substantial receptor-binding activity.

Directing the reductive alkylation of Schiff's bases of PEG-monoaldehydes toward the alpha amino group of the N-terminal amino acid of a receptor-binding protein and away from the epsilon amino groups of its lysine residues can be accomplished by a variety of methods, based on the disclosures in J. T. Edsall in Chapters 4 and 5 of *Proteins Amino Acids and Peptides as Ions and Dipolar Ions* ((1943), Reinhold Publishing Corporation, New York), the disclosure of which is incorporated herein by reference in its entirety. The acidic dissociation constant ("$pK_a$") of an alpha amino group of an N-terminal amino acid of a polypeptide is expected to be below 7.6, whereas the $pK_a$ values of the epsilon amino groups of lysine residues in polypeptides are expected to be approximately 9.5. Edsall ((1943, supra) clearly stated that aldehydes will combine with the amino group of an amino acid "only on the alkaline side of its isoelectric point."

Hence, based on the present disclosure and information that is readily available in the art, the ordinarily skilled artisan will recognize that (1) the selective reaction of aldehydes with the alpha amino group of a protein will be favored by a range of pH that is below 9.5 (approximately the $pK_a$ of the epsilon amino groups in the protein); (2) the rate of reaction of aldehydes with epsilon amino groups will decrease if the pH of the reaction is lowered toward 7.6 (approximately the $pK_a$ of the alpha amino group of the protein); (3) the rate of reaction of aldehydes with the alpha amino group will decrease less than that of the epsilon amino groups as the reaction pH is lowered toward 7.6, and (4) the selectivity for the reaction of an aldehyde with the alpha amino group will be improved somewhat by lowering the pH toward 6.6. Since the latter value is approximately one pH unit below the $pK_a$ of the alpha amino group and three pH units below the $pK_a$ of the epsilon amino groups, approximately 10% of the alpha amino groups and approximately 0.1% of the epsilon amino groups will be in their reactive, unprotonated state. Thus at pH 6.6, the fraction of unprotonated alpha amino groups is 100-fold higher than the fraction of unprotonated epsilon amino groups. Therefore, very little increase in selectivity will be obtained by lowering the pH of the reaction further, e.g., to 5.6, where, theoretically, 1% of the alpha amino groups and 0.01% of the epsilon amino groups would be in their reactive, unprotonated state. Thus, in certain embodiments of the invention, protein ligands (particularly "RN" or "RG" ligands, including cytokines and antagonists thereof) are conjugated with one or more polymers by forming a mixture between the ligand(s) and the one or more reactive polymers at a pH of about 5.6 to about 7.6; at a pH of about 5.6 to about 7.0; at a pH of about 6.0 to about 7.0; at a pH of about 6.5 to about 7.0; at a pH of about 6.6 to about 7.6; at a pH of about 6.6 to about 7.0; or at a pH of about 6.6. The present methods thus differ significantly from those known in the art, in which coupling of polymers to alpha amino groups on the N-terminal amino acid residues of ligands is carried out at a pH of about 5 (Kinstler, O., et al., (2002) supra; EP 0 822 199 A2; U.S. Pat. Nos. 5,824,784 and 5,985,265; Roberts, M. J., et al., (2002), supra; Delgado, C., et al., U.S. application Publication No. 2002/0127244 A1), while coupling of polymers to epsilon amino groups of lysine residues in the ligand polypeptide backbone is carried out at a pH of 8.0 (Kinstler, O., et al., EP 0 822 199 A2; U.S. Pat. Nos. 5,824,784 and 5,985,265). In the same way, the present methods also are significantly distinct from enzymatic methods that have been used for coupling alkylamine derivatives of poly(ethylene glycol) to certain proteins using transglutaminase, which is carried out at a pH of 7.5 (Sato, H., (2002) *Adv Drug Deliv Rev* 54:487-504).

Reduction of the resultant Schiff's bases with mild reducing agents, such as sodium cyanoborohydride or pyridine borane (Cabacungan, J. C., et al., (1982) *Anal Biochem* 124: 272-278), forms secondary amine bonds that preserve the positive charge of the N-terminal alpha amino group of the protein at physiological pH. Such bonds that retain the same charge as the native protein are more likely to preserve its biological activity than alternative linkage chemistries that neutralize the charge, e.g., by the formation of amide bonds (Burg, J., et al., PCT Publication No. WO 02/49673 A2; Kinstler, O., et al., European Patent Application No. EP 0 822 199 A2; Kinstler, O., et al., (1996) *Pharm Res,* 13:996-1002; Kita, Y., et al., supra) or urethane bonds (Gilbert, C. W., et al., U.S. Pat. No. 6,042,822; Grace, M., et al., (2001) *J Interferon Cytokine Res* 21:1103-1115; Youngster, S., et al., (2002) *Curr Pharm Des* 8:2139-2157).

Alternative approaches to selective coupling of polymers to N-terminal amino acid residues are known to those skilled in the art. Included are methods for coupling hydrazide, hydrazine, semicarbazide or other amine-containing polymers to N-terminal serine or threonine residues that have been oxidatively cleaved to aldehydes with periodate (Dixon, H. B. F., supra; Geoghegan, K. F., U.S. Pat. No. 5,362,852; Gaertner, H. F., et al., (1996) *Bioconjug Chem* 7:38-44; Drummond, R. J., et al., U.S. Pat. No. 6,423,685).

Suitable Polymers

In certain embodiments of the invention, it is desirable to minimize the formation of intramolecular and intermolecular cross-links by polymers such as PEG during the reaction in which the polymer is coupled to the bioactive component to produce the conjugates of the invention. This can be accomplished by using polymers that are activated at only one end (referred to herein as "monofunctionally activated PEGs" or "monofunctionally activated PAGs") or polymer preparations in which the percentage of bifunctionally activated (referred to in the case of linear PEGs as "bis-activated PEG diols") or multi-functionally activated polymers is less than about 30%, or more preferably less than about 10% or most preferably less than about 2% (w/w). The use of activated polymers that are entirely or nearly entirely monofunctional can minimize the formation of all of the following: intramolecular cross links within individual protein molecules, "dumbbell" structures, in which one strand of polymer connects two protein molecules, and larger aggregates or gels.

Activated forms of polymers that are suitable for use in the methods and compositions of this invention can include any linear or branched, monofunctionally activated forms of polymers that are known in the art. For example, included are those with molecular weights (excluding the mass of the activating group) in the range of about 1 kDa to about 100 kDa. Suitable ranges of molecular weights include but are not limited to about 5 kDa to about 30 kDa; about 8 kDa to about 14 kDa; about 10 kDa to about 20 kDa; about 18 kDa to about 60 kDa; about 18 kDa to about 22 kDa; about 12 kDa to about 30 kDa, about 5 kDa, about 10 kDa, about 20 kDa or about 30 kDa. In the case of linear PEGs, molecular weights of about 10 kDa, about 20 kDa or about 30 kDa correspond to degrees of polymerization (n) of about 230, about 450 or about 680 monomeric units of ethylene oxide, respectively. It should be noted that long before the existence of the "RN" and "RG" classes of receptor-binding proteins was recognized, the advantages of coupling therapeutic proteins to polymers having relatively high molecular weights (i.e., >20-30 kDa) were first disclosed (Saifer, M., et al., PCT Publication No. WO 89/01033 A1, published Feb. 9, 1989, which is incorporated herein by reference in its entirety).

In other embodiments of the invention, conjugates of receptor-binding proteins with unusually high percentages of retained bioactivity can be prepared for use in vitro, e.g., in cell culture, by coupling monofunctionally activated polymers of about 1 kDa, about 2 kDa or about 5 kDa, according to the methods of this invention. For such in vitro applications, this lower range of molecular weights may be preferred.

Optionally, a linear polymer can have a reactive group at one end or both ends, thereby creating a "reactive polymer." In certain embodiments of this invention, it can be desirable to use the N-hydroxysuccinimidyl ester of the monopropionic acid derivative of PEG, as disclosed in J. M. Harris, et al., U.S. Pat. No. 5,672,662, which is incorporated herein fully by reference, or other N-hydroxysuccinimide-activated PEG-monocarboxylic acids. In certain other embodiments, it can be desirable to use either the monosuccinimidyl carbonate derivatives of PEG ("SC-PEG"), as described in M. Saifer, et al., U.S. Pat. Nos. 5,006,333; 5,080,891; 5,283,317 and 5,468,478, or the mono-p-nitrophenyl carbonate derivative of PEG, as disclosed in S. J. Kelly, et al., supra; in L. D. Williams, et al. PCT Publication No. WO 00/07629 A2, L. D. Williams, et al., U.S. Pat. No. 6,576,235 and in M. R. Sherman, et al., PCT Publication No. WO 01/59078 A2. Moreover, other types of reactive groups can be used to synthesize polymer conjugates of proteins. These derivatives include, but are not limited to, monoaldehyde derivatives of PEGs (Royer, G. P., U.S. Pat. No. 4,002,531; Harris, J. M., et al., U.S. Pat. No. 5,252,714), monoamine, mono-tribromophenyl carbonate, monocarbonyl-imidazole, mono-trichlorophenyl carbonate, mono-trifluorophenyl carbonate, monohydrazide, monohydrazine, monosemicarbazide, monocarbazate, mono-thiosemicarbazide, monoiodoacetamide, monomaleimide, mono-orthopyridyl disulfide, mono-oxime, monophenylglyoxal, mono-thiazolidine-2-thione, monothioester, monothiol, monotriazine and monovinylsulfone derivatives of PEGs. In additional embodiments, cytokines, chemokines, growth factors, polypeptide hormones and antagonists thereof can be coupled to one or more polymers as described in commonly owned, co-pending U.S. patent application Ser. No. 10/669,597, the disclosure of which is incorporated herein by reference in its entirety.

Bioactive Components

As noted above, the conjugates of the invention comprise one PAG or PAO, and particularly one strand of PEG, covalently attached to one or more bioactive components. Bioactive components to which one or more polymers (or strands thereof) have been covalently attached are referred to herein variously and equivalently as "conjugated bioactive components" or "modified bioactive components." These terms are to be distinguished herein from "unconjugated bioactive components," "initial bioactive components" or "unmodified bioactive components," all of which terms refer to bioactive components that have not had polymers covalently attached thereto. It is to be understood, however, that an "unconjugated," "unmodified" or "initial" bioactive component may contain other, non-polymer conjugations or modifications when compared to a wild-type or native molecule, and would still be considered to be "unconjugated," "unmodified" or "initial" in accordance with the present invention, since the bioactive component would be "unconjugated," "unmodified" or "initial" with respect to the attachment of polymers, as is the case for bioactive components that are referred to herein as "Mock PEGylated."

The term "stabilizing" a bioactive component (or "methods of stabilization" or "stabilized bioactive component") indicates that a bioactive component has been stabilized according to the methods of this invention (i.e., a bioactive component to which a polymer has been covalently attached according to the methods of the invention). Such stabilized bioactive components will exhibit certain altered biochemical and biophysical characteristics when compared to a bioactive component that has not been stabilized (i.e., a bioactive component to which a polymer has not been covalently attached). Included among such altered biochemical and biophysical parameters, particularly for receptor-binding proteins, may be decreased susceptibility to proteolytic degradation and particularly the maintenance of the activity of a receptor-binding protein during incubation under certain harsh environmental or experimental conditions. In certain embodiments of the invention, the altered biochemical and biophysical parameters may include, for example, an increased half-life in the circulation in vivo, increased bioavailability, increased duration of action in vitro, and the like.

Any receptor-binding protein (typically a cytokine) having biological (i.e., physiological, biochemical or pharmaceutical) activity associated with portions of the molecule that are remote from its amino terminus or from a naturally occurring or mutationally-introduced glycosylation site can be suitably used as an initial component in the present invention. Such bioactive components include, but are not limited to, peptides, polypeptides, proteins and the like. Bioactive components also include fragments, muteins and derivatives of such peptides, polypeptides, proteins and the like, particularly such fragments, muteins and derivatives having biological (i.e., physiological, biochemical or pharmaceutical) activity.

Suitable peptides, polypeptides and proteins, glycoproteins and the like that are useful as bioactive components in the present invention include any peptide, polypeptide or protein, etc., having one or more than one available amino group, thiol group or other group that is remote from the receptor-binding region or regions of the bioactive component and to which polymers can be selectively attached. Such peptides, polypeptides, proteins, glycoproteins and the like include cytokines, which may have any of a variety of structures (Nicola, N. A., supra; Schein, C. H., supra).

For example, suitable peptides, polypeptides and proteins of interest include, but are not limited to the class of cytokines having structures comprising four α-helical bundles (both long-chain and short-chain subclasses) (for review, see Schein, C. H., supra). A variety of such four-helical bundle proteins are suitable for use in the present invention, including but not limited to interleukins, e.g., IL-2, IL-3, IL-4, IL-5, IL-6, IL-7, IL-9, IL-10, IL-11, IL-12 (p35 subunit), IL-13, IL-15 and IL-17; colony-stimulating factors, e.g., macrophage colony-stimulating factor (M-CSF) and granulocyte-macrophage colony-stimulating factor (GM-CSF; Rozwarski, D. A., et al., (1996) *Proteins* 26:304-313); interferons, e.g., IFN-α, IFN-β (including but not limited to IFN-β-1b) and consensus IFN; leukemia inhibitory factor (LIF); erythropoietin (Epo); thrombopoietin (Tpo); megakaryocyte growth and development factor (MGDF); stem cell factor (SCF), also known in the art as Steel Factor (Morrissey, P. J., et al., (1994) *Cell Immunol* 157:118-131; McNiece, I. K., et al., (1995) *J Leukoc Biol* 58:14-22); oncostatin M (OSM); phospholipase-activating protein (PLAP); neurotrophic factors; and peptide mimetics thereof. Although prolactin and growth hormone are classical hormones, which circulate widely in the body, unlike the cytokines, which are usually produced near their target cells, prolactin and growth hormone belong to the same structural class as the cytokines with four α-helical bundles (Nicola, N. A., supra; Goffin, V., et al., supra) and they are similarly suitable targets for polymer coupling and for production of the present conjugates in accordance with the present invention.

Receptor-binding proteins of the long chain β-sheet or β-barrel structural classes (for review, see Schein, C. H., supra) are also suitable for use in preparing the conjugates and compositions of the present invention. These include, but are not limited to: the tumor necrosis factor family of cytokines, e.g., TNF-α, TNF-β and Fas ligands, which display β-jelly roll structures; the IL-1 (including IL-1α and IL-1β) and FGF (including basic fibroblast growth factor (bFGF), acidic FGF, FGF-4 and keratinocyte growth factor (KGF; FGF-7)) families, which show a beta-trefoil fold (Schein, C. H., supra; Schlessinger, J., et al., supra); IL-12; IL-16; Epidermal Growth Factor (EGF; Lu, H.- S., et al., supra); and the platelet-derived growth factors (PDGFs), transforming growth factors (including transforming growth factor-α and transforming growth factor-β (TGF-β)) and nerve growth factors, which adopt cystine-knot structures.

An additional structural class of proteins that are advantageously used in the conjugates and compositions of the present invention is that of the disulfide-rich mixed α/β cytokines and growth factors (for review, see Schein, C. H., supra), including but not limited to: the EGF family, which has a beta-meander structure; IL-8; RANTES; neutrophil activating peptide-2 (NAP-2); stromal cell-derived factor-1α (SDF-1α); the monocyte chemoattractant proteins (MCP-1, MCP-2 and MCP-3); the eotaxins (e.g., eotaxin-1, eotaxin-2 and eotaxin-3); myeloid progenitor inhibitory factor-1 (MPIF-1); neurotactin, macrophage migration inhibitory factor (MIF); growth-related oncogene/melanoma growth stimulatory activity (GRO-α/MGSA); somatomedins; and insulin and the insulin-like growth factors (e.g., IGF-1 and IGF-2). A related structural class of proteins of use in the conjugates and compositions of the present invention is cytokines with mosaic structures, which includes growth factors such as IL-12 and hepatocyte growth factor (Nicola, N. A., supra).

Other proteins of interest include, but are not limited to: growth hormones (particularly human growth hormone (hGH; see Tchelet, A., et al., (1997) *Mol Cell Endocrinol* 130:141-152) and antagonists thereof (see, e.g., Sundström, M., et al., (1996) *J Biol Chem* 271:32197-32203), prolactin and antagonists thereof, chorionic gonadotropin, follicle-stimulating hormone, thyroid-stimulating hormone, pigmentary hormones, hypothalamic releasing factors, antidiuretic hormones and receptor-binding antagonists of cytokines and growth factors of all of the above structural classes. Many such proteins exist in both glycosylated and non-glycosylated forms. The non-glycosylated forms may result from their production using recombinant DNA techniques in prokaryotes or using chemical synthesis. Such non-glycosylated products are among the peptides and proteins that are suitable bioactive components of the present invention. Finally, although some antibodies function as receptor-binding agonists or antagonists (see, e.g., Morris, J. C., et al., (2000) *Ann Rheum Dis* 59 (*Suppl I*):i109-i114), such immunoglobulins are not suitable candidates for N-terminal polymer coupling within the scope of this invention, i.e., they are not RN receptor-binding proteins, since the amino-terminal regions of both the light and heavy chains participate in antigen recognition.

Of particular use as bioactive components for use in preparing the polymer conjugates of the present invention are interferon-alpha, interferon-beta, IL-2, IL-4, IL-10, hGH, prolactin, insulin, IGF-1, EGF, bFGF and erythropoietin (Epo). Also of particular use are muteins and fragments of such bioactive components, particularly those capable of binding to the receptors for the corresponding wild-type or intact polypeptide, whether or not this binding induces a biological or physiological effect. In certain such embodiments, muteins and fragments of the bioactive components can act as antagonists for the corresponding ligands, which reduce, substantially reduce or completely inhibit the binding of ligands to their receptors and/or the activity of the ligands on their target cells, tissues and/or organisms. Other antagonists, which may or may not be structural analogues, muteins, variants or derivatives of the ligands of interest, are also suitable for preparation of the conjugates in accordance with the present invention. As a practical matter, whether or not a given mutein, fragment, variant, derivative or antagonist antagonizes the biological and/or physiological effects of a given ligand can be determined, without undue experimentation, using assays for the biological/physiological effects of the ligand itself, a variety of which are well-known in the art and/or described herein.

The structures (primary, secondary, tertiary and, where applicable, quaternary) for these and other polypeptides of interest that are advantageously used in accordance with the present invention are well-known in the art and will be familiar to one of ordinary skill, particularly in view of the structures provided herein and in the references cited herein, which are incorporated herein by reference in their entireties.

Conjugates

The present invention provides stable conjugates of bioactive components, particularly of cytokines, for use in a variety of applications. Such conjugates of the invention have a number of advantages over those previously known in the art, as shown by the following non-limiting and exemplary comparisons of art-known conjugates:

H. Hiratani (European Patent No. EP 0098 110 B1 and U.S. Pat. No. 4,609,546) discloses conjugates of copolymers of ethylene oxide and propylene oxide ("PEG-PPG," a member of the general class of PAGs) with proteins, including interferons and interleukins, wherein no preference for avoiding regions of the proteins involved in-receptor binding is disclosed. In these references, interferons alpha, beta and gamma were considered to be equivalent targets for coupling of PAG, unlike in the present invention wherein interferon-gamma is not considered to be a suitable target for N-terminal coupling because the amino terminus is within the receptor-binding region of this cytokine. In addition, Hiratani discloses conjugates synthesized only with PAGs of 1 kDa to 10 kDa, whereas the methods of the present invention prefer the coupling of water-soluble, synthetic polymers with molecular weights exceeding 10 kDa for therapeutic applications. Analogously, N. V. Katre ((1990) supra) discloses that coupling larger numbers of strands of 5-kDa mPEG to human recombinant interleukin-2 increases the life-times of the resultant conjugates in the bloodstreams of mice and rabbits. However, this reference did not disclose or recognize the advantage of coupling a smaller number of longer strands of PEG or of coupling a single strand of high molecular weight PEG to the amino terminus of IL-2, as provided by the present invention.

G. Shaw (U.S. Pat. No. 4,904,584 and PCT Publication No. WO 89/05824 A2) discloses methods for inducing site-selective attachment of amine-reactive polymers by introducing, replacing or deleting lysine residues in the target protein, especially Epo, G-CSF and IL-2. However, unlike the disclosure of the present invention, these references do not disclose that amine-reactive polymers can react with any amine in the target protein other than the epsilon amino groups of lysine residues, clearly distinguishing these disclosures from the present invention.

D. E. Nitecki et al., (U.S. Pat. No. 4,902,502) disclose multiply PEGylated IL-2 conjugates that were prepared from various chloroformate derivatives of PEG that were intended to react with the epsilon amino groups of lysine residues. In contrast to the present methods, however, this reference discloses no method to avoid PEGylation of lysine residues in regions of the IL-2 protein that are involved in receptor binding, nor any awareness that avoidance of such sites is advantageous.

N. Katre, et al., (U.S. Pat. No. 5,206,344) disclose PEG-IL-2 conjugates in which PEG is coupled to the epsilon amino groups of lysine residues, to the unpaired sulfhydryl group of the naturally occurring cysteine residue at position 125 (counting from the amino terminus) or to the sulfhydryl group of a cysteine residue that has been mutationally introduced between the first and twentieth residues from the amino terminus of IL-2. Included among the muteins that are disclosed in the '344 patent is "des-ala-1" IL-2, i.e., a mutein in which the amino-terminal alanine is deleted and not PEGylated. In contrast to the present disclosure, however, the '344 patent does not disclose any method for avoiding coupling PEG to amino acid residues that are involved in binding to receptors, nor any recognition that such an approach would be advantageous. Consistent with this notion, and in contrast to the present invention, the broad range of points of attachment proposed in the '344 patent does not suggest that coupling PEG to the amino terminus of IL-2 would be especially advantageous.

S. P. Monkarsh, et al., (1997) *Anal Biochem* 247:434-440 and S. P. Monkarsh, et al., (1997) in Harris, J. M., et al., eds., *Poly(ethylene glycol): Chemistry and Biological Applications*, pp. 207-216, American Chemical Society, Washington, D.C., disclose that reacting interferon-alpha-2a with a three-fold molar excess of an activated PEG with a molecular weight of 5,300 Daltons produces eleven positional isomers of monoPEG-interferon, corresponding to the eleven lysine residues in interferon-alpha-2a. No PEG-interferon in which the PEG is coupled to the alpha amino group at the amino terminus of the interferon was reported. The eleven positional isomers reported in these references displayed antiviral activities in cell cultures that ranged from 6% to 40% of that of the unmodified interferon and antiproliferative activities in cell cultures that ranged from 9% to 29% of that of the unmodified interferon. Such results clearly demonstrate that the random PEGylation of lysine residues practiced by these investigators interfered with the functions of interferon-alpha-2a mediated by its receptors, in contrast to conjugates prepared by the methods of the present invention. In addition, unlike the conjugates of the present invention, there was no N-terminally PEGylated interferon in the conjugates reported in these references.

O. Nishimura et al., (U.S. Patent Statutory Invention Registration No. H1662) disclose conjugates of interferon-alpha, interferon-gamma and IL-2 that are prepared by reductive alkylation of activated "polyethylene glycol methyl ether aldehydes" with sodium cyanoborohydride at pH 7.0 (for the interferon conjugates) or pH 7.15 (for the IL-2 conjugates). The conjugates prepared by such methods, however, were reported to have lost up to 95% of the bioactivity of the unmodified proteins, apparently due to the presence of multiple sites of polymer attachment, all of which were reported to be on the epsilon amino groups of lysine residues (cf., FIGS. 1 and 4 of the present invention).

D. K. Pettit, et al., (1997) *J Biol Chem* 272:2312-2318, disclose polymer conjugates of interleukin-15 ("IL-15"). The conjugated IL-15 reported in this reference, however, not only lost its IL-2-like growth-promoting capacity as a result of coupling polymers to lysine residues in regions of the protein that are involved in receptor binding, but it also showed antagonism rather than agonism. These authors conclude that selective inhibition of binding of IL-15 to one of several cell surface receptors can be a consequence of polymer conjugation and that such inhibition can not only decrease receptor binding, but can reverse the biological effect of the protein. By avoiding the coupling of polymers to portions of the receptor-binding protein that are involved in interactions with their receptors, the present invention avoids this undesirable consequence of polymer coupling.

J. Hakimi, et al., (U.S. Pat. Nos. 5,792,834 and 5,834,594) disclose urethane-linked PEG conjugates of proteins, including interferon-alpha, IL-2, interleukin-1 ("IL-1") and an antagonist of the IL-1-receptor, which were reportedly prepared in order to decrease the immunogenicity, increase the solubility and increase the biological half-life of the respective proteins. In these references, PEG was coupled to "various free amino groups," with no reference to N-terminal PEGylation and no disclosure that the N-terminal alpha amino groups could or should be PEGylated. These patents also state that the conjugate disclosed therein "has at least a portion" of the original biological activity of the starting protein, thus indicating possible loss of substantial bioactivity. This result would be consistent with the use of the untargeted PEGylation methods disclosed therein. In contrast to the present invention, these patents do not disclose any attempt to improve the retention of bioactivity of their conjugates by altering the selectivity of the PEGylation processes disclosed therein.

O. B. Kinstler, et al., (European Patent Application No. EP 0 822 199 A2) disclose a process for reacting poly(ethylene glycol) with the alpha amino group of the amino acid at the amino terminus of a polypeptide, especially consensus interferon and G-CSF, which are two of the proteins manufactured by Amgen, Inc., the assignee of this patent application. This publication indicates that "a pH sufficiently acidic to selectively activate the alpha amino group" is a necessary feature of the disclosed process. In contrast, by the present invention it has been discovered that lowering the pH decreases the reactivity of amino groups with PEG aldehydes and that the alpha amino group is more reactive when it is not protonated, i.e., at a pH above its $pK_a$. Thus, the present inventors find that no pH is "sufficiently acidic to selectively activate the alpha amino group" of any of the RN cytokine conjugates of the present invention. The explanations of the pH dependence of the reactivity of N-terminal alpha amino groups with aldehydes given by J. T. Edsall (supra) and by R. S. Larsen et al., ((2001) *Bioconjug Chem* 12:861-869) are more compatible with the experience of the present inventors. Furthermore, Kinstler et al. report the use of N-terminal PEGylation of polypeptides for increased homogeneity of the resulting conjugates and protection of the amino terminus from degradation by proteinases, but do not disclose that N-terminal PEGylation can preserve a greater fraction of the receptor-binding activity of certain receptor-binding proteins (see, e.g., PCT Publication No. WO 96/11953; European Patent No. EP 0 733 067 B1, and U.S. Pat. Nos. 5,770,577, 5,824,784 and 5,985,265, all of Kinstler, O. B., et al.).

The European application of Kinstler et al. (EP 0 822 199 A2) also generalizes the benefits of N-terminal PEGylation to all polypeptides, which has not been the experience of the present inventors. Specifically, since the amino termini of antibody molecules occur proximal to the antigen-combining region of the antibody proteins (Chapman, A. P. (2002) *Adv Drug Deliv Rev* 54:531-545), N-terminal PEGylation of antibodies is unexpectedly deleterious to bioactivity, compared to random PEGylation of lysine residues, as disclosed by Larsen, R. S., et al., supra. Similarly, N-terminal PEGylation of receptor-binding proteins that are not "RN" receptor-binding proteins, e.g., interferon-gamma (see FIG. 8), is expected to be more inhibitory of interactions with receptors than random PEGylation of the lysine residues of such receptor-binding proteins.

Thus, as noted above, the methods of the present invention are distinguished from those disclosed by Kinstler et al. in the publications cited herein, in that the conjugates of the present invention are prepared by conjugating one or more cytokines or antagonists thereof that are selected as RN receptor-binding proteins with one or more polymers by forming a mixture between the ligand(s) and the one or more polymers at a pH of about 5.6 to about 7.6; at a pH of about 5.6 to about 7.0; at a pH of about 6.0 to about 7.0; at a pH of about 6.5 to about 7.0; at a pH of about 6.6 to about 7.6; at a pH of about 6.6 to about 7.0; or at a pH of about 6.6. In contrast, the methods of Kinstler et al. rely on conjugation of ligands at a pH below 5.5, which pH range the present inventors have found to be suboptimal or inferior for preparing preparations of ligands selectively conjugated with polymers at remote N-terminal amino acids and/or at remote glycosylation sites.

Pepinsky, B., et al., (PCT Publication No. WO 00/23114 and U.S. patent application Publication No. 2003/0021765 A1) disclose polymer conjugates of glycosylated interferon-beta-1a that are more active than nonglycosylated interferon-beta-1b in an antiviral assay. When Pepinsky et al. coupled 5-kDa or 20-kDa mPEG to the amino terminus of IFN-β-1a by reductive alkylation, no effect of PEGylation on the antiviral potency was observed, whereas the coupling of PEGs of higher molecular weight decreased or eliminated the potency. This reference also discloses that polyalkylene glycol can be coupled to the interferon-beta-1a via a variety of coupling groups at various sites, including the amino terminus, the carboxyl terminus and the carbohydrate moiety of the glycosylated protein. The methods disclosed in this publication, however, are stated not to be generalizable: "[t]hese studies indicate that, despite the conservation in sequence between interferon-beta-1a and interferon-beta-1b, they are distinct biochemical entities and therefore much of what is known about interferon-beta-1b cannot be applied to interferon-beta-1a, and vice versa." In contrast, the present invention discloses the common features embodied in "RN" and "RG" receptor-binding proteins, as defined herein. According to the present invention, both interferon-beta-1a and interferon-beta-1b are "RN" receptor-binding proteins. In addition, interferon-beta-1b is an "RG" receptor-binding protein. Accordingly, in contrast to the methods of WO 00/23114, the methods of the present invention are useful for preparing stable, bioactive conjugates of both interferon-beta-1b and interferon-beta-1a.

Z. Wei, et al., (U.S. Pat. No. 6,077,939), disclose methods for coupling water-soluble polymers (especially PEG) to the N-terminal alpha carbon atom of a polypeptide (especially erythropoietin), wherein the amine at the alpha carbon of the N-terminal amino acid is first transaminated to an alpha carbonyl group that is then reacted with a PEG derivative to form an oxime or a hydrazone bond. Since the disclosed objective of this reference was to develop a method that would be applicable to proteins in general, no consideration was given to the preservation of receptor-binding activity that can result from the choice of the amino terminus as the site of PEGylation of certain receptor-binding proteins. Thus, in contrast to the disclosure of Wei, et al., the present invention does not require the removal of the N-terminal alpha amino group, but, in contrast, can preserve the charge of the N-terminal alpha amino group at neutral pH through the formation of a secondary amine linkage between the protein and the polymer.

C. W. Gilbert et al., (U.S. Pat. No. 6,042,822; European Patent No. EP 1 039 922 B1) disclose the desirability of a mixture of positional isomers of PEG-interferon-alpha-2b wherein an especially desirable isomer has PEG coupled to a histidine residue of interferon-alpha-2b, especially histidine-34, and demonstrate that the PEG linkage to histidine-34 is unstable. Since histidine-34 lies on the surface of interferon-alpha-2b in a region that must come into intimate contact with an interferon receptor in order to trigger signal transduction (see FIG. 1b of the present specification), the instability of the linkage between PEG and histidine-34 disclosed in these references appears to be critical to the function of the PEG-interferon conjugate disclosed therein. Substantially pure histidine-linked protein polymer conjugates were described by S. Lee et al., U.S. Pat. No. 5,985,263. In contrast, the present invention demonstrates that one preferred conjugate is a PEG-interferon conjugate wherein the PEG is stably linked at a site that is remote from the receptor-binding domains of the interferon component.

P. Bailon, et al., ((2001) *Bioconjug Chem* 12:195-202), disclose that interferon-alpha-2a that is PEGylated with one molecule of 40-kDa di-mPEG-lysine per molecule of interferon is comprised of four major positional isomers. This reference discloses that nearly all of the PEG was attached by amide bonds to lysines 31, 121, 131 or 134, each of which is within or adjacent to the receptor-binding domains of interferon-alpha-2a (residues 29-35 and 123-140, according to Bailon et al.; see FIG. 1a of the present specification). N-terminal PEGylation was not reported by Bailon et al. Antiviral activity of the isolated mixture of positional isomers of PEG-interferon against Vesicular Stomatitis Virus infection of Madin-Darby bovine kidney cells in vitro was reported to be 7% of that of the unconjugated interferon-alpha-2a that was tested. The substantial loss of bioactivity that was observed for these PEG-interferon conjugates that do not include N-terminally PEGylated interferon thus clearly distinguishes the conjugates of Bailon et al. from those of the present invention.

R. B. Pepinsky et al., ((2001) *J Pharmacol Exp Ther* 297: 1059-1066), disclose synthesis of a conjugate from (1) glycosylated interferon-beta-1a having an N-terminal methionine residue and (2) a 20-kDa PEG-aldehyde. The conjugate, which is referred to in the reference as being monoPEGylated at the N-terminal methionine, is said to retain full bioactivity in an antiviral assay. While these authors disclose that their choice of the N-terminal site for PEGylation of glycosylated interferon-beta-1a was dictated by the availability of site-selective PEGylation reagents and molecular modeling, they acknowledge that "some effects are product specific." Moreover, and in contrast to the present invention, the observations reported therein were not generalized to include the class of receptor-binding proteins that are defined herein as "RN" receptor-binding proteins.

J. Burg, et al., (PCT Publication No. WO 01/02017 A2) disclose the production of alkoxyPEG conjugates of erythropoietin glycoproteins, wherein one to three strands of a methoxyPEG was/were reacted with sulfhydryl groups that were introduced chemically by modification of epsilon amino groups of lysine residues on the surface of the glycoprotein. In contrast to the present invention, however, this reference does not disclose any attempt to couple PEG to the free alpha amino group of the N-terminal amino acid of erythropoietin or to avoid modifying lysine residues in regions of the erythropoietin glycoprotein that are essential for interactions with erythropoietin receptors.

J. Burg, et al., (PCT Publication No. WO 02/49673 A2) disclose the synthesis of N-terminally amide-linked PEG conjugates of natural and mutein erythropoietin glycoproteins by a process that employs selectively cleavable N-terminal peptide extensions that are cleaved before PEGylation and after reversible citraconylation of all epsilon amino groups of the lysine residues of the glycoprotein. The disclosed rationale for the multi-step process in this reference was to make the PEGylation process selective for the free alpha amino group of the N-terminal amino acid in order to produce homogeneous monoPEGylated conjugates, thereby avoiding the need to separate monoPEGylated conjugates from multiply PEGylated derivatives. This method differs from that of the present invention in a number of important respects, including but not limited to: (1) the approach of Burg et al. is limited to erythropoletin glycoproteins to which alkoxyPEG is linked via amide bonds, while the present invention is applicable to a variety of bioactive components conjugated using a variety of synthetic polymers; (2) the present invention applies to both glycosylated and nonglycosylated "RN" and "RG" receptor-binding proteins, whereas Burg et al. disclose only the conjugation of glycoproteins; (3) the present invention encompasses both alkoxyPEGs, such as mPEG, and monofunctionally-activated hydroxyPEGs, whereas Burg et al. disclose only the use of alkoxyPEGs; and (4) in the present invention, secondary amine linkages between the polymer and the protein are preferred over the amide linkages used by Burg et al., since the former are more stable and conserve the positive charge on the amino group. In analogous work from the same group, J. Burg, et al., (U.S. Pat. No. 6,340,742) disclose the production of amide-linked conjugates of erythropoietin glycoproteins, wherein one to three strands of alkoxyPEG is/are linked to one to three amino groups of the protein. In contrast to the present invention, however, this reference reports no preference for the alpha amino group of the N-terminal amino acid or for amino groups that are not in regions that are involved in interactions with receptors.

C. Delgado et al., (U.S. Pat. No. 6,384,195) disclose conjugates of granulocyte-macrophage colony-stimulating factor that are prepared using a reactive polymer that is represented as tresyl monomethoxyPEG and is referred to therein as "TMPEG." This reference indicates that when TMPEG is contacted with recombinant human GM-CSF, "[t]he modified material contains species with no activity and with higher activity than unmodified material." As one of ordinary skill will readily recognize, species with no activity are undesirable in a mixture of polymer-bioactive component conjugates, particularly in compositions for therapeutic use that comprise such conjugates, since they can contribute to the risks of administering the conjugate to a patient in need of such administration without contributing to the beneficial effects. As noted herein, the present invention overcomes this limitation in the art at least in part by avoiding modification of GM-CSF and other receptor-binding proteins at sites on the proteins that are involved in its receptor-binding activity, thereby reducing or eliminating the synthesis of species with no activity. The present invention also provides methods for the fractionation and purification of conjugates that have different sizes, different charges and/or different extents of shielding of charges on the protein by the polymer (see FIGS. 9-12).

It is noteworthy that U.S. Pat. No. 6,384,195 does not mention the N-terminal PEGylation of GM-CSF and therefore does not recognize the advantages of the methods of the present invention. Finally, U.S. Pat. No. 6,384,195 indicates a preference for conjugates in which more than one PEG is coupled to each molecule of GM-CSF, without any consideration of where on the GM-CSF molecule those PEG molecules are attached (other than being coupled to lysine residues). By stating a preference for conjugates with up to six PEG molecules per GM-CSF, the reference thus states a preference for conjugates in which PEG might be attached to all possible lysine residues, thereby ensuring that PEG will be attached in positions that sterically hinder close approach of the protein to its cell-surface receptors (see FIG. 3 of the present specification). By contrast, the present invention indicates the undesirability of coupling PEG to lysine residues, except when those lysine residues are remote from the domains of the receptor-binding protein that are essential for interactions with the receptors and hence for signal transduction (in the case of agonists) or in order to competitively inhibit signal transduction (in the case of antagonists).

T. Nakamura, et al., (PCT Publication No. WO 02/32957 A1) discloses that increasing the molecular weight of PEG that is coupled to the epsilon amino group of the lysine residue at position 52 of erythropoietin glycoprotein increases the erythropoietic effect of the conjugate in vivo while decreasing the affinity of the conjugate for erythropoietin receptors. In contrast to the present invention, however, this reference does not disclose the coupling of PEG at the amino terminus or near a glycosylation site, nor does it recognize any advantage to doing so.

Hence, the present invention provides conjugates of bioactive components coupled to synthetic polymers that have distinct structural and functional advantages to those that have been previously disclosed.

Compositions

The invention provides conjugates or complexes comprising one or more bioactive components, suitably one or more cytokines, coupled to one or more stabilizing polymers such as one or more PEGs. Typically, such conjugates are produced by the methods of the present invention described herein; however, conjugates having the structures and activities described herein, regardless of the methods used to produce such conjugates, are considered equivalent to those produced by the present methods and are therefore encompassed by the present invention. In related aspects, the invention also provides compositions comprising one or more such conjugates or complexes. Compositions according to this aspect of the invention will comprise one or more (e.g., one, two, three, four, five, ten, etc.) of the above-described conjugates or complexes of the invention. In certain such aspects, the compositions may comprise one or more additional components, such as one or more buffer salts, one or more chaotropic agents, one or more detergents, one or more proteins (e.g., albumin or one or more enzymes), one or more unbound polymers, one or more osmotically active agents and the like. The compositions of this aspect of the invention may be in any form, including solid (e.g., dry powder) or solution (particularly in the form of a physiologically compatible buffered salt solution comprising one or more of the conjugates of the invention).

A. Pharmaceutical Compositions

Certain compositions of the invention are particularly formulated for use as pharmaceutical compositions for use in prophylactic, diagnostic or therapeutic applications. Such compositions will typically comprise one or more of the conjugates, complexes or compositions of the invention and one or more pharmaceutically acceptable carriers or excipients. The term "pharmaceutically acceptable carrier or excipient," as used herein, refers to a non-toxic solid, semi-solid or liquid filler, diluent, encapsulating material or formulation auxiliary of any type that is capable of being tolerated by a recipient animal, including a human or other mammal, into which the pharmaceutical composition is introduced, without adverse effects resulting from its addition.

The pharmaceutical compositions of the invention may be administered to a recipient via any suitable mode of administration, such as orally, rectally, parenterally, intrasystemically, vaginally, intraperitoneally, topically (as by powders, ointments, drops or transdermal patch), buccally, as an oral or nasal spray or by inhalation. The term "parenteral" as used herein refers to modes of administration that include intravenous, intra-arterial, intramuscular, intraperitoneal, intracisternal, subcutaneous and intra-articular injection and infusion.

Pharmaceutical compositions provided by the present invention for parenteral injection can comprise pharmaceutically acceptable sterile aqueous or nonaqueous solutions, dispersions, suspensions or emulsions, as well as sterile powders for reconstitution into sterile injectable solutions or dispersions prior to use. Examples of suitable aqueous and non-aqueous carriers, diluents, solvents or vehicles include water, ethanol, polyols (such as glycerol and the like, propylene glycol, poly(ethylene glycol)), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Such pharmaceutical compositions of the present invention may also contain adjuvants such as preservatives, wetting agents, emulsifying agents and dispersing agents. Prevention of the action of microorganisms may be ensured by the inclusion of various antibacterial and antifungal agents, for example, paraben, benzyl alcohol, chlorobutanol, phenol, sorbic acid, and the like. It may also be desirable to include osmotic agents such as sugars, sodium chloride and the like. Prolonged absorption of the injectable pharmaceutical form may be brought about by the inclusion of agents that delay absorption, such as aluminum monostearate, hydrogels and gelatin.

In some cases, in order to prolong the effect of the drugs, it is desirable to slow the absorption from subcutaneous or intramuscular injection. This may be accomplished by the use of a liquid suspension of crystalline or amorphous material with poor solubility in aqueous body fluids. The rate of absorption of the drug then depends upon its rate of dissolution, which, in turn, may depend upon its physical form. Alternatively, delayed absorption of a parenterally administered drug form can be accomplished by dissolving or suspending the drug in an oil vehicle.

Injectable depot forms are made by forming microencapsulated matrices of the drug in biodegradable polymers such as polylactide-polyglycolide. Depending upon the ratio of drug to carrier polymer and the nature of the particular carrier polymer employed, the rate of drug release can be controlled. Examples of other biodegradable polymers include biocompatible poly(orthoesters) and poly(anhydrides). Depot injectable formulations are also prepared by entrapping the drug in liposomes or microemulsions that are compatible with body tissues.

The injectable formulations can be sterilized, for example, by filtration through a bacteria-retaining filter, or by incorporating sterilizing agents in the form of sterile solid compositions that can be dissolved or dispersed in sterile water or other sterile injectable medium prior to use.

Solid dosage forms for oral administration include capsules, tablets, pills, powders and granules. In such solid dosage forms, the active compounds are mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and gum acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) accelerators of absorption, such as quaternary ammonium compounds, g) wetting agents such as, for example, cetyl alcohol and glycerol monostearate, h) adsorbents such as kaolin and bentonite clay, and i) lubricants such as talc, calcium stearate, magnesium stearate, solid PEGs, sodium lauryl sulfate, and mixtures thereof. In the case of capsules, tablets and pills, the dosage form may also comprise buffering agents.

Solid compositions of a similar type may also be employed as fillers in soft- and hard-filled gelatin capsules using such excipients as lactose (milk sugar) as well as high molecular weight PEGs and the like.

The solid dosage forms of tablets, dragees, capsules, pills and granules can be prepared with coatings and shells such as enteric or chronomodulating coatings and other coatings well known in the pharmaceutical formulating art. They may optionally contain opacifying agents and can also be of such a composition that they release the active ingredient(s) only, or preferentially, in a certain part of the gastrointestinal tract, optionally, in a delayed manner. Examples of embedding compositions that can be used include polymeric substances and waxes. The active compounds can also be in microencapsulated form, if appropriate, with one or more of the above-mentioned excipients.

Liquid dosage forms for oral administration can include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, PEGs and fatty acid esters of sorbitan, and mixtures thereof.

In addition to inert diluents, the oral compositions can also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose and sucrose. Desirably, at least 95% by weight of the particles of the active ingredient have an effective particle size in the range of 0.01 to 10 micrometer.

Alternatively, the pharmaceutical composition may be pressurized and contain a compressed gas, such as nitrogen or a liquefied gas propellant. The liquefied propellant medium and indeed the total composition may be preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferable to use the solid anionic surface-active agent in the form of a sodium salt.

A further form of topical administration is to the eye. In this mode of administration, the conjugates or compositions of the invention are delivered in a pharmaceutically acceptable ophthalmic vehicle, such that the active compounds are maintained in contact with the ocular surface for a sufficient time period to allow the compounds to penetrate the conjunctiva or the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories that can be prepared by mixing the conjugates or compositions of the invention with suitable non-irritating excipients or carriers such as cocoa butter, PEG or a suppository wax, which are solid at room temperature but liquid at body temperature and therefore melt in the rectum or vaginal cavity and release the drugs.

The pharmaceutical compositions used in the present therapeutic methods may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. In addition to one or more of the conjugates or compositions of the invention, the present pharmaceutical compositions in liposome form can also contain one or more stabilizers, preservatives, excipients, and the like. The preferred lipids are the phospholipids and the phosphatidyl cholines (lecithins), both natural and synthetic. Methods to form liposomes are known in the art (see, e.g., Zalipsky, S., et al., U.S. Pat. No. 5,395,619). Liposomes that comprise phospholipids that are conjugated to PEG, most commonly phosphatidyl ethanolamine coupled to monomethoxyPEG, have advantageous properties, including prolonged lifetimes in the blood circulation of mammals (Fisher, D., U.S. Pat. No. 6,132,763).

B. Uses

As noted elsewhere herein, the methods, conjugates and compositions of the present invention are advantageously used in methods for maintaining or enhancing the bioactivity of the biological components without interfering with the ability of the biological components to bind to their receptors. Certain such methods of the invention may entail delivering one or more of the conjugates and compositions to cells, tissues, organs or organisms. In particular, the invention provides controlled delivery of the one or more components of the conjugates, complexes or compositions to cells, tissues, organs or organisms, thereby providing the user with the ability to regulate, temporally and spatially, the amount of a particular component that is released for activity on the cells, tissues, organs or organisms.

In general, such methods of the invention involve one or more activities. For example, one such method of the invention comprises: (a) preparing one or more conjugates or compositions of the invention as detailed herein; and (b) contacting one or more cells, tissues, organs or organisms with the one or more conjugates or compositions, under conditions favoring the binding of the one or more conjugates or compositions of the invention to the cells, tissues, organs or organisms. Once the bioactive components of the conjugates and/or compositions of the invention have been bound by (or, in some cases, internalized by) the cells, tissues, organs or organisms, the components proceed to carry out their intended biological functions. For example, peptide components may bind to receptors or other components on or within the cells, tissues, organs or organisms; to participate in metabolic reactions within the cells, tissues, organs or organisms; to carry out, upregulate or activate, or downregulate or inhibit, one or more enzymatic activities within the cells, tissues, organs or organisms; to provide a missing structural component to the cells, tissues, organs or organisms; to provide one or more nutritional needs to the cells, tissues, organs or organisms; to inhibit, treat, reverse or otherwise ameliorate one or more processes or symptoms of a disease or physical disorder; and the like.

In additional embodiments, the conjugates and compositions of the invention can be used in industrial cell culture, due to the unexpectedly high potencies of the bioactive components of the conjugates that are obtained as a result of the combined effects of substantial retention of their bioactivity and increased duration of action even under the conditions of industrial use. These unexpectedly high potencies of the present conjugates can lead to unusually high biomass production, unusually high levels of expression of recombinant proteins, and other improvements in efficiencies of bioprocessing.

C. Dose Regimens

The conjugates, complexes or compositions of the invention can be administered in vitro, ex vivo or in vivo to cells, tissues, organs or organisms to deliver thereto one or more bioactive components (i.e., one or more cytokines or antagonists thereof). One of ordinary skill will appreciate that effective amounts of a given active compound, conjugate, complex or composition can be determined empirically and may be employed in pure form or, where such forms exist, in pharmaceutically acceptable formulation or prodrug form. The compounds, conjugates, complexes or compositions of the invention may be administered to an animal (including a mammal, such as a human) patient in need thereof as veterinary or pharmaceutical compositions in combination with one or more pharmaceutically acceptable excipients. The therapeutically effective dose level for any particular patient will depend upon a variety of factors including the type and degree of the cellular response to be achieved; the identity and/or activity of the specific compound(s), conjugate(s), complex(es) or composition(s) employed; the age, body weight or surface area, general health, gender and diet of the patient; the time of administration, route of administration, and rate of excretion of the active compound(s); the duration of the treatment; other drugs used in combination or coincidental with the specific compound(s), conjugate(s), complex(es) or composition(s); and like factors that are well known to those of ordinary skill in the pharmaceutical and medical arts. For example, it is well within the ordinary skill of the art to start doses of a given compound, conjugate, complex or composition of the invention at levels lower than those required to achieve the desired therapeutic effect and to gradually increase the dosages until the desired effect is achieved.

Dose regimens may also be arranged in a patient-specific manner to provide a predetermined concentration of a given active compound in the blood, as determined by techniques accepted and routine in the art, e.g. size-exclusion, ion-exchange or reversed-phase high performance liquid chromatography ("HPLC"), bioassays or immunoassays. Thus, patient dose regimens may be adjusted to achieve relatively constant blood levels, as measured by HPLC or immunoassays, according to methods that are routine and familiar to those of ordinary skill in the medical, pharmaceutical and/or pharmacological arts.

D. Diagnostic and Therapeutic Uses

A diagnostic use of a conjugate of the invention might be for locating cells or tissues having unusually high binding capacity for the cytokine, e.g., a cancer, within the body of an animal, especially a human, by administration of a conjugate or composition of the invention, in which the conjugate (or one or more components, i.e., the bioactive component and/or the synthetic polymer) is labeled or comprises one or more detectable labels so as to enable detection, e.g., by optical, radiometric, fluorescent or resonant detection according to art-known methods. For example, the majority of non-small cell lung cancers express unusually high concentration of receptors for epidermal growth factor (Bunn, P. A., et al., (2002) *Semin Oncol* 29(*Suppl* 14):38-44). Hence, in another aspect of the invention, the conjugates and compositions of the invention may be used in diagnostic or therapeutic methods, for example in diagnosing, treating or preventing a variety of physical disorders in an animal, particularly a mammal such as a human, predisposed to or suffering from such a disorder. In such approaches, the goal of the therapy is to delay or prevent the development of the disorder, and/or to cure, induce a remission or maintain a remission of the disorder, and/or to decrease or minimize the side effects of other therapeutic regimens.

Hence, the conjugates, complexes and compositions of the present invention may be used for protection, suppression or treatment of physical disorders, such as infections or diseases. The term "protection" from a physical disorder, as used herein, encompasses "prevention," "suppression" and "treatment." "Prevention" involves the administration of a complex or composition of the invention prior to the induction of the disease or physical disorder, while "suppression" involves the administration of the conjugate or composition prior to the clinical appearance of the disease; hence, "prevention" and "suppression" of a physical disorder typically are undertaken in an animal that is predisposed to or susceptible to the disorder, but that is not yet suffering therefrom. "Treatment" of a physical disorder, however, involves administration of the therapeutic conjugate or composition of the invention after the appearance of the disease. It will be understood that in human and veterinary medicine, it is not always possible to distinguish between "preventing" and "suppressing" a physical disorder. In many cases, the ultimate inductive event or events may be unknown or latent, and neither the patient nor the physician may be aware of the inductive event until well after its occurrence. Therefore, it is common to use the term "prophylaxis," as distinct from "treatment," to encompass both "preventing" and "suppressing" as defined herein. The term "protection," used in accordance with the methods of the present invention, therefore, is meant to include "prophylaxis." Methods according to this aspect of the invention may comprise one or more steps that allow the clinician to achieve the above-described therapeutic goals. One such method of the invention may comprise, for example: (a) identifying an animal (preferably a mammal, such as a human) suffering from or predisposed to a physical disorder; and (b) administering to the animal an effective amount of one or more of the conjugates, complexes or compositions of the present invention as described herein, such that the administration of the conjugate, complex or composition prevents, delays or diagnoses the development of, or cures or induces remission of, the physical disorder in the animal.

As used herein, an animal that is "predisposed to" a physical disorder is defined as an animal that does not exhibit a plurality of overt physical symptoms of the disorder but that is genetically, physiologically or otherwise at risk for developing the disorder. In the present methods, the identification of an animal (such as a mammal, including a human) that is predisposed to, at risk for, or suffering from a given physical disorder may be accomplished according to standard art-known methods that will be familiar to the ordinarily skilled clinician, including, for example, radiological assays, biochemical assays (e.g., assays of the relative levels of particular peptides, proteins, electrolytes, etc., in a sample obtained from an animal), surgical methods, genetic screening, family history, physical palpation, pathological or histological tests (e.g., microscopic evaluation of tissue or bodily fluid samples or smears, immunological assays, etc.), testing of bodily fluids (e.g., blood, serum, plasma, cerebrospinal fluid, urine, saliva, semen and the like), imaging, (e.g., radiologic, fluorescent, optical, resonant (e.g., using nuclear magnetic resonance ("NMR") or electron spin resonance ("ESR")), etc. Once an animal has been identified by one or more such methods, the animal may be aggressively and/or proactively treated to prevent, suppress, delay or cure the physical disorder.

Physical disorders that can be prevented, diagnosed or treated with the conjugates, complexes, compositions and methods of the present invention include any physical disorders for which the bioactive component (typically, the cytokine or antagonist thereof) of the conjugates or compositions may be used in the prevention, diagnosis or treatment. Such disorders include, but are not limited to, a variety of cancers (e.g., breast cancers, uterine cancers, ovarian cancers, prostate cancers, testicular cancers, leukemias, lymphomas, lung cancers, neurological cancers, skin cancers, head and neck cancers, bone cancers, colon and other gastrointestinal cancers, pancreatic cancers, bladder cancers, kidney cancers and other carcinomas, sarcomas, adenomas and myelomas); iatrogenic diseases; infectious diseases (e.g., bacterial diseases, fungal diseases, viral diseases (including hepatitis, diseases caused by cardiotropic viruses, HIV/AIDS, and the like), parasitic diseases, and the like); genetic disorders (e.g., cystic fibrosis, amyotrophic lateral sclerosis, muscular dystrophy, Gaucher's disease, Pompe's disease, severe combined immunodeficiency disorder, dwarfism and the like), anemia, neutropenia, thrombocytopenia, hemophilia and other blood disorders; neurodegenerative disorders (e.g., multiple sclerosis ("MS," including but not limited to relapsing-remitting MS, primary progressive MS, secondary progressive MS, and the like), Creutzfeldt-Jakob Disease, Alzheimer's disease, and the like); enzymatic disorders (e.g., gout, uremia, hypercholesterolemia, and the like); disorders of uncertain or multifocal etiology (e.g., cardiovascular disease, hypertension, inflammatory bowel disease and the like); autoimmune disorders (e.g., systemic lupus erythematosus, rheumatoid arthritis, psoriasis, and the like) and other disorders of medical importance that will be readily familiar to the ordinarily skilled artisan. The conjugates, complexes, compositions and methods of the present invention may also be used in the prevention of disease progression, such as in chemoprevention of the progression of a premalignant lesion to a malignant lesion.

The therapeutic methods of the invention thus use one or more conjugates, complexes or compositions of the invention, or one or more of the pharmaceutical compositions of the invention, that may be administered to an animal in need thereof by a variety of routes of administration, including orally, rectally, parenterally (including intravenously, intraarterially, intramuscularly, intraperitoneally, intracisternally, subcutaneously and intra-articular injection and infusion), intrasystemically, vaginally, intraperitoneally, topically (as by powders, ointments, drops or transdermal patch), buccally, as an oral or nasal spray or by inhalation. By the invention, an effective amount of the conjugates, complexes or compositions can be administered in vitro, ex vivo or in vivo to cells or to animals suffering from or predisposed to a particular disorder, thereby preventing, delaying, diagnosing or treating the disorder in the animal. As used herein, "an effective amount of a conjugate (or complex or composition)" refers to an amount such that the conjugate (or complex or composition) carries out the biological activity of the bioactive component (i.e., the cytokine or antagonist thereof) of the conjugate, complex or composition, thereby preventing, delaying, diagnosing, treating or curing the physical disorder in the animal to which the conjugate, complex or composition of the invention has been administered. One of ordinary skill will appreciate that effective amounts of the conjugates, complexes or compositions of the invention can be determined empirically, according to standard methods well-known to those of ordinary skill in the pharmaceutical and medical arts; see, e.g., Beers, M. H., et al., eds. (1999) *Merck Manual of Diagnosis & Therapy,* 17th edition, Merck and Co., Rahway, N.J.; Hardman, J. G., et al., eds. (2001) *Goodman and Gilman's The Pharmacological Basis of Therapeutics,* 10th edition, McGraw-Hill Medical Publishing Division, New York; Speight, T. M., et al., eds. (1997) *Avery's Drug Treatment,* 4th edition, Adis International, Auckland, New Zealand; Katzung, B. G. (2000) *Basic & Clinical Pharmacology,* 8th edition, Lange Medical Books/McGraw-Hill, New York; which references and references cited therein are incorporated entirely herein by reference.

It will be understood that, when administered to a human patient, the total daily, weekly or monthly dosage of the conjugates, complexes and compositions of the present invention will be decided by the attending physician within the scope of sound medical judgment. For example, satisfactory results are obtained by administration of certain of the conjugates, complexes or compositions of the invention at appropriate dosages depending on the specific bioactive compound used, which dosages will be readily familiar to the ordinarily skilled artisan or which may be readily determined empirically using only routine experimentation. According to this aspect of the invention, the conjugates, complexes or compositions can be administered once or, in divided doses, e.g., once or twice per day, or once or twice per week, or once or twice per month, etc. Appropriate dose regimens for various modes of administration (e.g., parenteral, subcutaneous, intramuscular, intra-ocular, intranasal, etc.) can also be readily determined empirically, using only routine experimentation, or will be readily apparent to the ordinarily skilled artisan, depending on the identity of the bioactive component (i.e., the cytokine or antagonist thereof) of the conjugate, complex or composition.

In additional applications, the conjugates, complexes and compositions of the invention may be used to specifically target a diagnostic or therapeutic agent to a cell, tissue, organ or organism that expresses a receptor for, binds, incorporates or otherwise can take up, the bioactive component (i.e., the cytokine or antagonist thereof) of the conjugate, complex or composition. Methods according to this aspect of the invention may comprise, for example, contacting the cell, tissue, organ or organism with one or more conjugates, complexes or compositions of the invention, which additionally comprise one or more diagnostic or therapeutic agents, such that the conjugate, complex or composition is bound to or taken up by the cell, tissue, organ or organism, thereby delivering the diagnostic or therapeutic agent to the cell, tissue, organ or organism. The diagnostic or therapeutic agent used in accordance with this aspect of the invention may be, but is not limited to, at least one agent selected from a nucleic acid, an organic compound, a protein or peptide, an antibody, an enzyme, a glycoprotein, a lipoprotein, an element, a lipid, a saccharide, an isotope, a carbohydrate, an imaging agent, a detectable probe, or any combination thereof, which may be detectably labeled as described herein. A therapeutic agent used in this aspect of the present invention may have a therapeutic effect on the target cell (or tissue, organ or organism), the effect being selected from, but not limited to, correcting a defective gene or protein, a drug action, a toxic effect, a growth stimulating effect, a growth inhibiting effect, a metabolic effect, a catabolic affect, an anabolic effect, an antiviral effect, an antifungal effect, an antibacterial effect, a hormonal effect, a neurohumoral effect, a cell differentiation stimulatory effect, a cell differentiation inhibitory effect, a neuromodulatory effect, an anti-neoplastic effect, an anti-tumor effect, an insulin stimulating or inhibiting effect, a bone marrow stimulating effect, a pluripotent stem cell stimulating effect, an immune system stimulating effect, and any other known therapeutic effect that may be provided by a therapeutic agent delivered to a cell (or tissue, organ or organism) via a delivery system according to this aspect of the present invention.

Such additional therapeutic agents may be selected from, but are not limited to, known and new compounds and compositions including antibiotics, steroids, cytotoxic agents, vasoactive drugs, antibodies and other therapeutic agents. Non-limiting examples of such agents include antibiotics and other drugs used in the treatment of bacterial shock, such as gentamycin, tobramycin, nafcillin, parenteral cephalosporins, etc.; adrenal corticosteroids and analogs thereof, such as dexamethasone, mitigate the cellular injury caused by endotoxins; vasoactive drugs, such as an alpha adrenergic receptor blocking agent (e.g., phenoxybenzamine), a beta adrenergic receptor agonist (e.g., isoproterenol), and dopamine.

The conjugates, complexes and compositions of the invention may also be used for diagnosis of disease and to monitor therapeutic response. In certain such methods, the conjugates, complexes or compositions of the invention may comprise one or more detectable labels (such as those described elsewhere herein). In specific such methods, these detectably labeled conjugates, complexes or compositions of the invention may be used to detect cells, tissues, organs or organisms expressing receptors for, or otherwise taking up, the bioactive component (i.e., cytokine or antagonist thereof) of the conjugates, complexes or compositions. In one example of such a method, the cell, tissue, organ or organism is contacted with one or more of the conjugates, complexes or compositions of the invention under conditions that favor the binding or uptake of the conjugate by the cell, tissue or organism (e.g., by binding of the conjugate to a cell-surface receptor or by pinocytosis or diffusion of the conjugate into the cell), and then detecting the conjugate bound to or incorporated into the cell using detection means specific to the label used (e.g., fluorescence detection for fluorescently labeled conjugates; magnetic resonance imaging for magnetically labeled conjugates; radioimaging for radiolabeled conjugates; etc.). Other uses of such detectably labeled conjugates may include, for example, imaging a cell, tissue, organ or organism, or the internal structure of an animal (including a human), by administering an effective amount of a labeled form of one or more of the conjugates of the invention and measuring detectable radiation associated with the cell, tissue, organ or organism (or animal). Methods of detecting various types of labels and their uses in diagnostic and therapeutic imaging are well known to the ordinarily skilled artisan, and are described elsewhere herein.

In another aspect, the conjugates and compositions of the invention may be used in methods to modulate the concentration or activity of a specific receptor for the bioactive component of the conjugate on the surface of a cell that expresses such a receptor. By "modulating" the activity of a given receptor is meant that the conjugate, upon binding to the receptor, either activates or inhibits the physiological activity (e.g., the intracellular signaling cascade) mediated through that receptor. While not intending to be bound by any particular mechanistic explanation for the regulatory activity of the conjugates of the present invention, such conjugates can antagonize the physiological activity of a cellular receptor by binding to the receptor via the bioactive component of the conjugate, thereby blocking the binding of the natural agonist (e.g., the unconjugated bioactive component) and preventing activation of the receptor by the natural agonist, while not inducing a substantial activation of the physiological activity of the receptor itself. Methods according to this aspect of the invention may comprise one or more steps, for example contacting the cell (which may be done in vitro or in vivo) with one or more of the conjugates of the invention, under conditions such that the conjugate (i.e., the bioactive component portion of the conjugate) binds to a receptor for the bioactive component on the cell surface but does not substantially activate the receptor. Such methods will be useful in a variety of diagnostic, and therapeutic applications, as the ordinarily skilled artisan will readily appreciate.

Kits

The invention also provides kits comprising the conjugates and/or compositions of the invention. Such kits typically comprise a carrier, such as a box, carton, tube or the like, having in close confinement therein one or more containers, such as vials, tubes, ampoules, bottles, syringes and the like, wherein a first container contains one or more of the conjugates and/or compositions of the present invention. The kits encompassed by this aspect of the present invention may further comprise one or more additional components (e.g., reagents and compounds) necessary for carrying out one or more particular applications of the conjugates and compositions of the present invention, such as one or more components useful for the diagnosis, treatment or prevention of a particular disease or physical disorder (e.g., one or more additional therapeutic compounds or compositions, one or more diagnostic reagents, one or more carriers or excipients, and the like), one or more additional conjugates or compositions of the invention, and the like.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

PEG-Interferon-Alpha Conjugates

Interferon-alpha is a commercially important medicinal protein with a world market in the year 2001 exceeding U.S. $2 billion, primarily for the treatment of patients with hepatitis C virus ("HCV") infections. In the United States, between three and four million people are infected with chronic hepatitis C and about 10,000 HCV-related deaths occur each year (Chander, G., et al., (2002) *Hepatology* 36:5135-5144). In attempting to improve the usefulness of IFN-alpha, both of the companies that are primarily responsible for its development and marketing (Schering-Plough Corp. and F. Hoffmann-La Roche A G) have developed and commercially launched conjugates of IFN-alpha with monomethoxypoly(ethylene glycol) or "mPEG." In each case, mPEG is linked to each molecule of interferon-alpha at only one point of attachment. In each case, the product contains a mixture of positional isomers with markedly reduced receptor-binding activity, compared to the unmodified interferon. In each case, the increased bioavailability and duration of action of the conjugate in vivo more than compensates for the decreased bioactivity in vitro that results from PEG conjugation, as measured by improved clinical effectiveness of one injection of the conjugate per week, compared to three injections of the unmodified protein per week, for the treatment of chronic infection with HCV (Manns, M. P., et al., (2001) *Lancet* 358:958-965).

In the PEG-interferon-alpha-2a conjugate of F. Hoffmann-La Roche, two strands of 20-kDa mPEG are coupled to a single lysine linker (so-called "branched PEG") that is linked primarily to one of Lys 31, Lys 121, Lys 131 or Lys 134 (Bailon, P., et al., supra), all of which are within or adjacent to a receptor-binding domain of interferon-alpha-2a (see Binding Site 1 in FIG. 1a).

In the PEG-interferon-alpha-4b conjugate of Schering-Plough Corp., a single strand of 12-kDa mPEG is coupled predominantly to a histidine residue at position 34 (His 34; Wylie, D. C., et al., supra; Gilbert, C. W., et al., U.S. Pat. No. 6,042,822; Wang, Y.-S., et al., supra), which is in a region that is important for binding to a receptor (see FIG. 1b). Other sites of PEG attachment in the product of Schering-Plough (Lys 121, Tyr 129 and Lys 131) are also seen to be in or near Binding Site 1 (FIG. 1b).

In contrast to these two commercial products, the conjugate of the present invention has a single strand of water soluble, synthetic polymer, preferably PEG or mPEG, linked to the N-terminal amino acid residue, which is remote from the receptor-binding regions of the protein (see the spatial relationship between Cys-1 and the Binding Sites in FIGS. 1c and 1d), demonstrating that interferon-alpha is an "RN" cytokine. FIGS. 9 and 10 show cation-exchange and size-exclusion chromatograms, respectively, of an exemplary PEG-interferon-alpha conjugate of the present invention. The reaction mixture contained interferon-alpha-2b in which an additional methionine residue was present at the amino terminus, preceding Cys-1, which is the first residue of the natural sequence. The reactive PEG was 20-kDa PEG-aldehyde, which was present at a concentration of 0.2 mM. The reducing agent was sodium cyanoborohydride, at a final concentration of 14 mM. Progress of the reaction was monitored periodically by size-exclusion chromatography during incubation at 4° C. Although IFN-alpha was sufficiently soluble to be PEGylated under the conditions described, other cytokines, e.g., IFN-beta, are less soluble and may need to be PEGylated in the presence of a surfactant, as described for IFN-alpha by C. W. Gilbert et al., (U.S. Pat. No. 5,711,944) and for interferons alpha and beta by R. B. Greenwald, et al., (U.S. Pat. No. 5,738,846).

The cation-exchange column used for the fractionation shown in FIG. 9 was TOYOPEARL® MD-G SP chromatography resin (1×6.8 cm; Tosoh Biosep, Montgomeryville, Pa.), developed with a linear gradient of 0-0.4 M NaCl in 20 mM sodium acetate buffer, pH 4.6, at a flow rate of 0.5 mL/minute. The size-exclusion column used to obtain the data in FIG. 10 was SUPERDEX® 200 gel filtration chromatography media (HR 10/30; Amersham Biosciences, Piscataway, N.J.), eluted at 0.5 mL/minute in 20 mM sodium acetate buffer containing 150 mM NaCl, pH 4.6. Other suitable ion-exchange and size-exclusion chromatographic media and fractionation conditions are known to those skilled in the art. Amino-terminal amino acid analysis by automated Edman degradation of the purified monoPEG-IFN-alpha-2b of this invention demonstrated that >90% of the PEG was attached to the N-terminal residue. The analysis was performed by Commonwealth Biotechnologies, Inc. (Richmond, Va.).

Example 2

PEG-Interleukin-2 Conjugates

Interleukin-2 ("IL-2") is a cytokine that displays immunomodulatory activity against certain cancers, including renal cell carcinoma and malignant melanoma. However, clinical efficacy is poor, with the result that only a small fraction of patients experience partial or complete responses (Weinreich, D. M., et al., (2002) *J Immunother* 25:185-187). IL-2 has a short half-life in the bloodstream, which is implicated in its low rate of induction of remission in cancer patients. Attempts to make IL-2 more useful by random PEGylation of lysine residues have not been optimal (Chen, S. A., et al., (2000) *J Pharmacol Exp Ther* 293:248-259). Attempts to selectively attach PEG to IL-2 at its glycosylation site (Goodson, R. J., et al., supra) or at a non-essential cysteine (Cys 125) or to muteins of IL-2 containing cysteine between residues 1 and 20 (Katre, N., et al., U.S. Pat. No. 5,206,344) have not led to clinically useful products.

Figure 4:
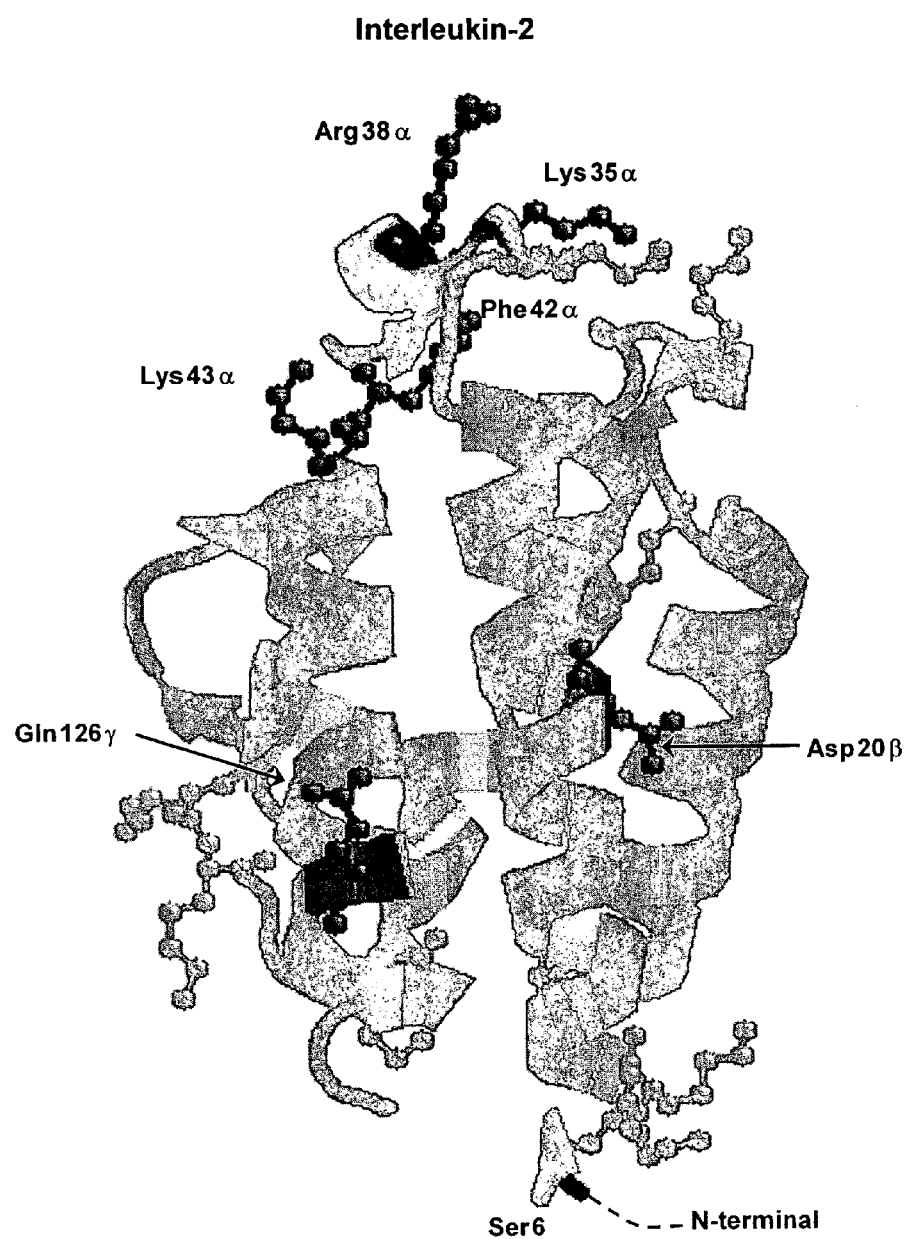

FIG. 4 shows the distribution of lysine residues with respect to the receptor-binding regions of IL-2, showing that many of the surface-accessible lysine residues are in regions that are involved in receptor binding. In fact, Lys-35 and Lys-43 have been identified as required for interaction with the alpha-receptor for IL-2, suggesting a mechanism for the inactivation of IL-2 by PEGylation of lysine residues. FIG. 4 also shows that the N-terminal region of IL-2 is remote from the receptor-binding regions of the protein, demonstrating that IL-2 has the structure of an "RN" cytokine. Our conclusion that IL-2 is an "RN" cytokine is compatible with the observations of H. Sato, et al., ((2000) *Bioconjug Chem* 11:502-509), who employed enzymatic transglutamination to couple one or two strands of 10-kDa mPEG to one or two of the glutamine residues ("Q") in the sequence AQQIVM that those authors introduced into an IL-2 mutein as an N-terminal extension. Sato et al. reported that their conjugate that was PEGylated near the amino terminus by transglutamination of their mutein retained more bioactivity than a conjugate prepared by random PEGylation of lysines in the IL-2 mutein. For a review of analogous approaches to PEGylation of other proteins, see Sato, H., (2002) supra. Based on the spatial separation of the amino terminus of IL-2 from the receptor-binding regions of the protein, as shown in FIG. 4, one can understand that the glycosylation site at residue Thr-3 (not shown) renders IL-2 an "RG" receptor-binding protein, as defined herein. Thus, IL-2 is both an RN cytokine and an RG cytokine.

FIGS. 11 and 12 show cation-exchange and size-exclusion chromatograms, respectively, of an exemplary PEG-IL-2 conjugate of the present invention, which was PEGylated by N-terminally selective, reductive alkylation, as in Example 1. The conditions used for fractionation were the same as those described for FIGS. 9 and 10, respectively. FIG. 13 shows a polyacrylamide gel electrophoretic analysis of the same conjugate in the presence of sodium dodecyl sulfate ("SDS-PAGE"), before and after its purification by ion-exchange chromatography, as shown in FIG. 11. The gel contained a gradient of 4-12% total acrylamide in Bis-Tris buffer (Catalog #NP0335, Invitrogen, Carlsbad, Calif.). The samples, each containing about 1-2 mcg protein, were heated at 90° C. for 10 minutes prior to analysis. The gel was run at a constant voltage of 117-120 for about 135 minutes, with cooling. One portion of the gel was stained with Sypro® Ruby protein gel stain (Molecular Probes, Eugene, Oreg.) and the other portion was stained for PEG by an adaptation of the methods of C. E. Childs ((1975) *Microchem J* 20:190-192) and B. Skoog ((1979) *Vox Sang* 37:345-349). Amino-terminal amino acid analysis by automated Edman degradation of the purified monoPEG-IL-2 in each of the two peaks in FIG. 11 demonstrated that >90% of the PEG was attached to the N-terminal residue. The analysis was performed by Commonwealth Biotechnologies, Inc. (Richmond, Va.).

Example 3

Members and Non-Members of the Class of "RN" Receptor-Binding Proteins

Figure 2:
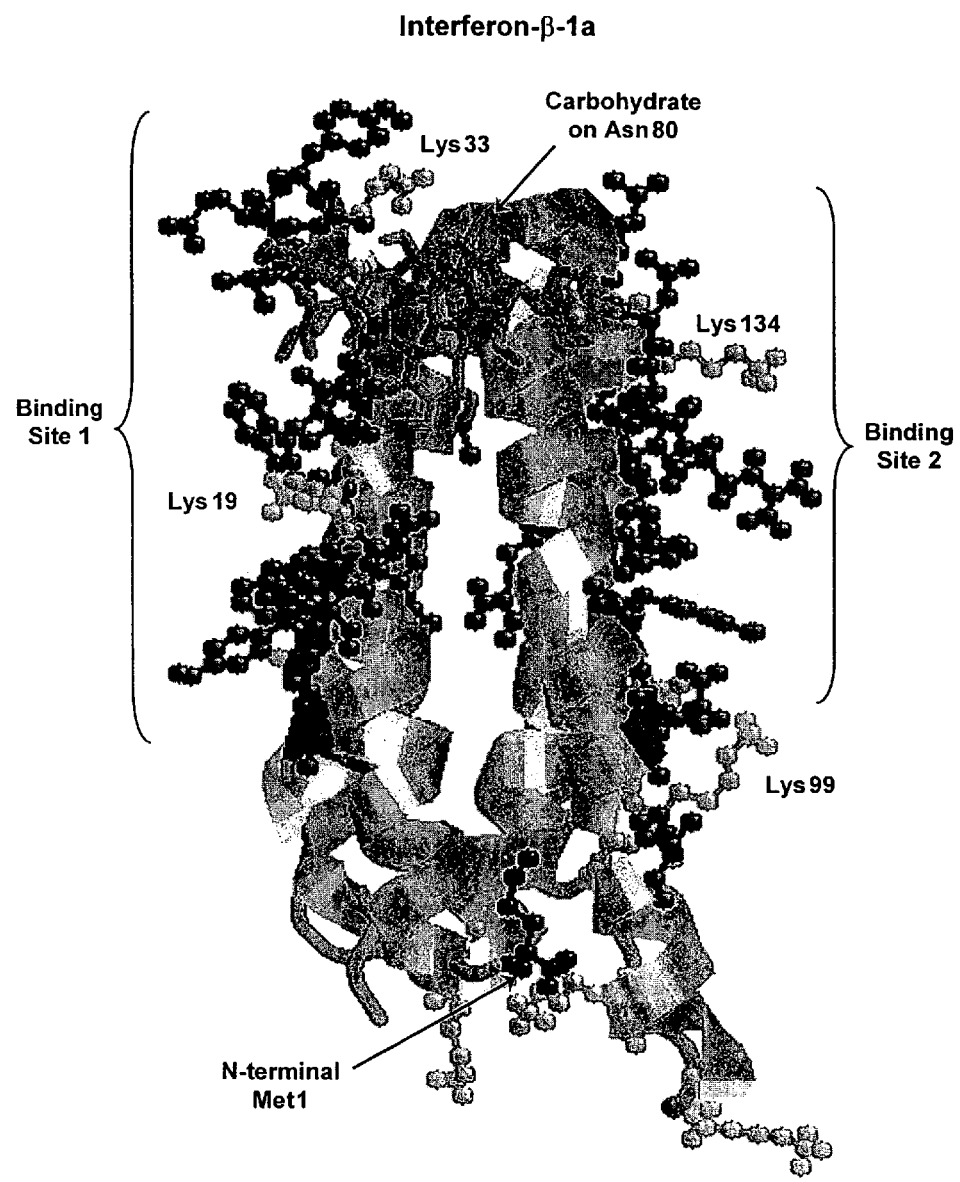

FIGS. 2, 3 and 5-8 show the surface distributions of lysine residues of the receptor-binding proteins interferon-beta, granulocyte-macrophage colony-stimulating factor ("GM-CSF"), epidermal growth factor ("EGF"), basic fibroblast growth factor ("bFGF," which is also known in the art as "FGF-2"), insulin-like growth factor-1 ("IGF-1") and interferon-gamma ("IFN-gamma") relative to their receptor-binding regions, as well as showing which of these proteins are "RN" cytokines and growth factors. In addition, FIG. 2 shows that interferon-beta is an "RG" cytokine.

FIG. 2 shows lysine residues distributed throughout the regions of Binding Site 1 and Binding Site 2 of interferon-beta, whereas the amino terminus of the polypeptide chain is remote from the receptor-binding regions of the protein, demonstrating that IFN-beta is an RN cytokine.

Figure 3:
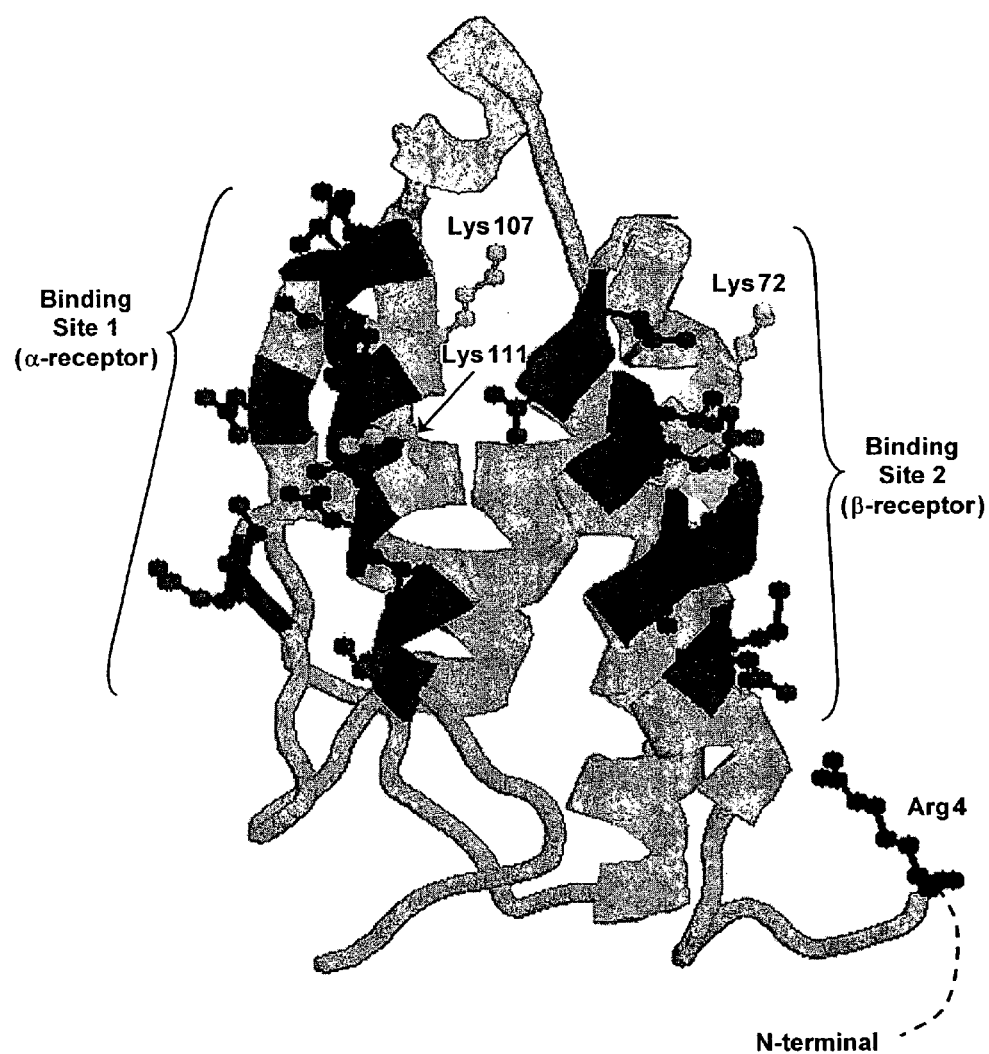

FIG. 3 shows lysine residues distributed throughout the regions of Binding Site 1, which binds the alpha receptor, and Binding Site 2, which binds the beta receptor, of GM-CSF, whereas the amino terminus of the polypeptide chain is remote from the receptor-binding regions of the protein, demonstrating that GM-CSF is an RN cytokine.

Figure 5:
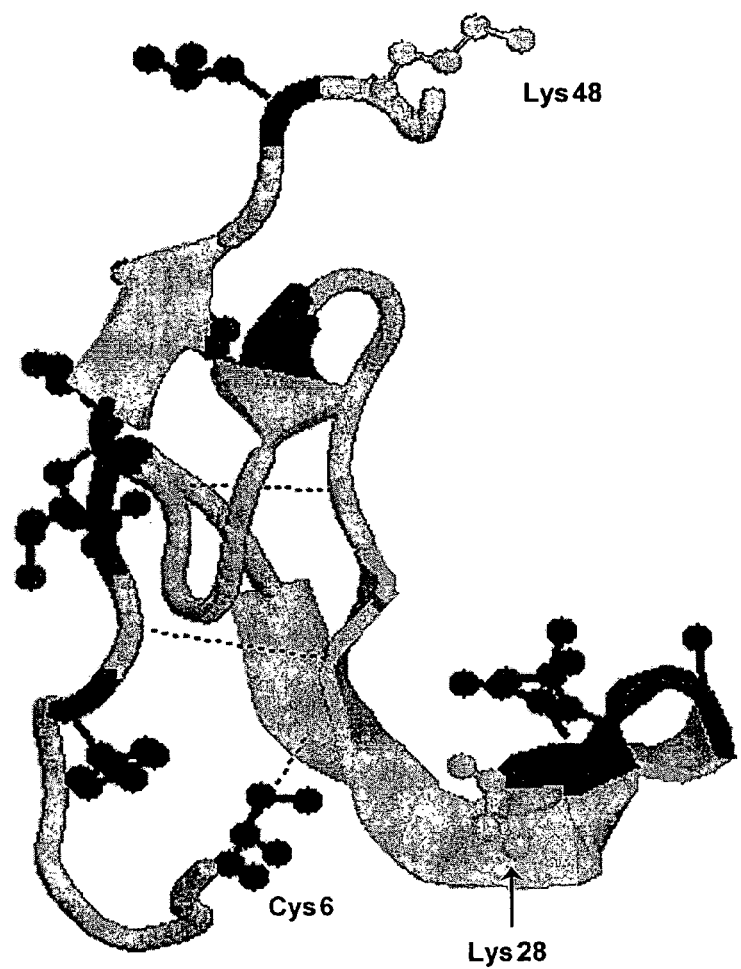

FIG. 5 shows lysine residues distributed along the polypeptide chain of epidermal growth factor ("EGF"), including lysine residues that are in or near receptor-binding regions of the protein, whereas the amino terminus of the polypeptide chain is more remote from the receptor-binding regions of the protein.

Figure 6:
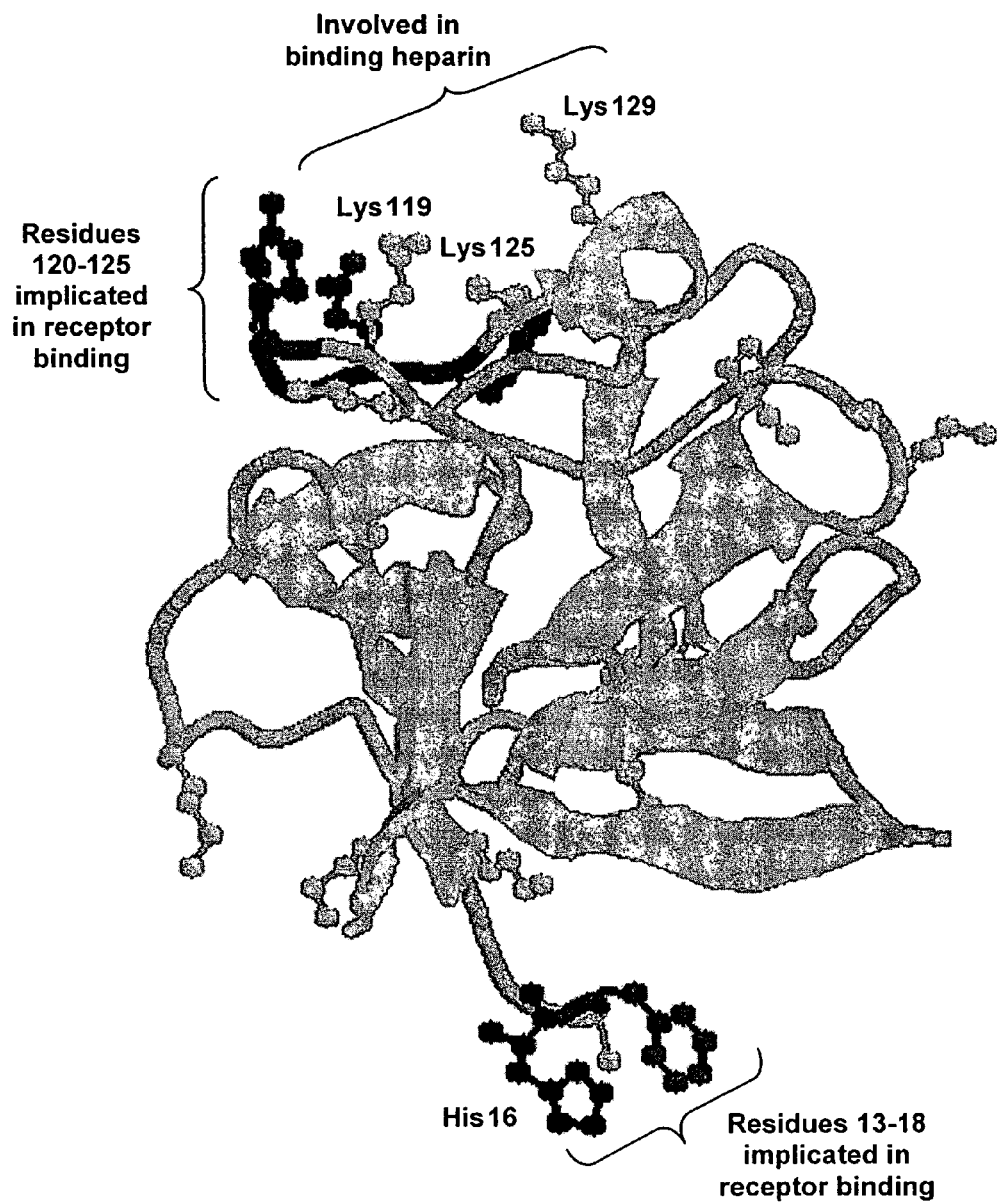

FIG. 6 shows that several lysine residues of basic fibroblast growth factor ("bFGF") are implicated in binding to receptors or to heparin, both of which are necessary for signal transduction by bFGF (Schlessinger, J., et al., supra). The amino terminus of bFGF is remote from the heparin-binding region of bFGF and may be sufficiently remote from receptor binding sites to render bFGF an RN growth factor.

Figure 7:
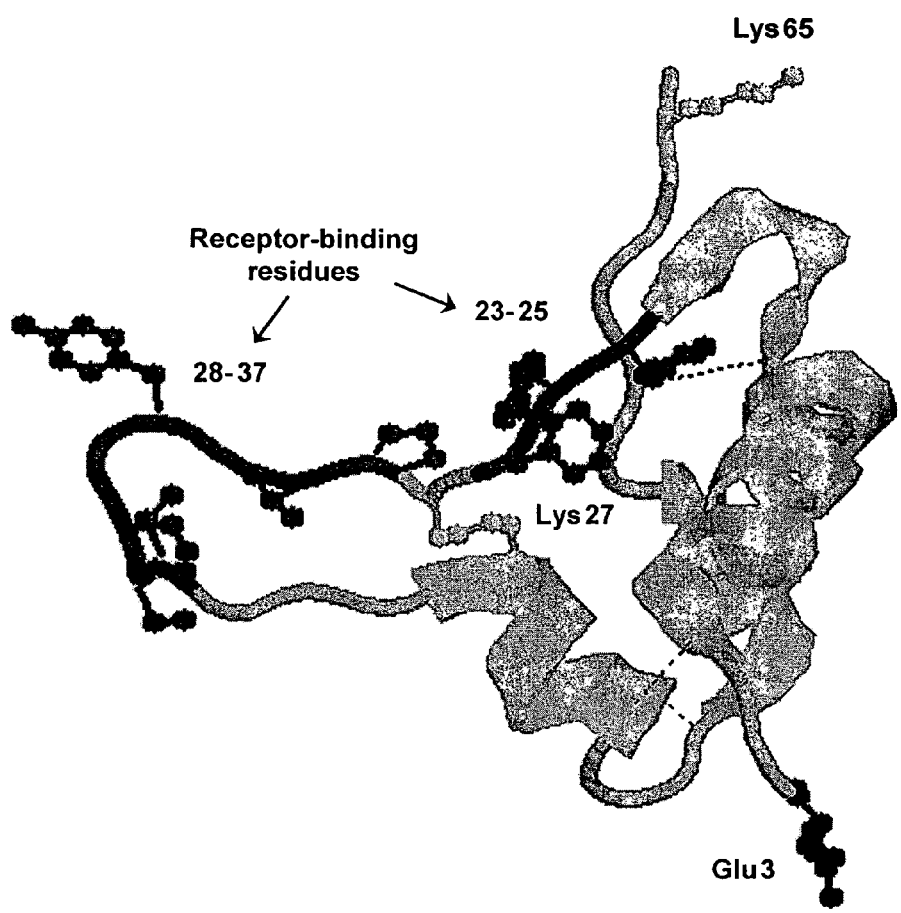

FIG. 7 shows that several lysine residues of insulin-like growth factor-1 ("IGF-1") are within or adjacent to the receptor-binding regions of the polypeptide, whereas the amino terminus of IGF-1 is remote from the receptor-binding domains, demonstrating that IGF-1 is an RN growth factor.

Figure 8:
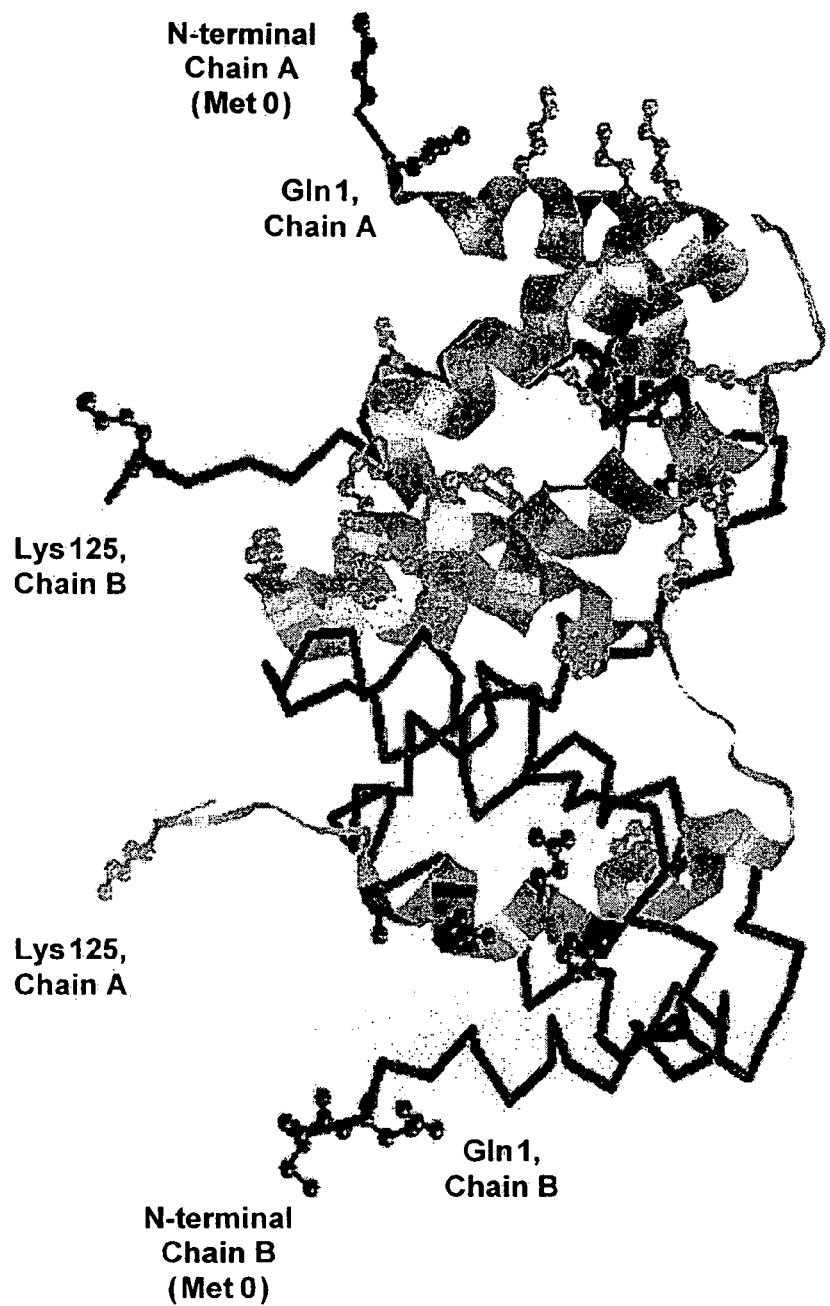

FIG. 8 shows that interferon-gamma ("IFN-gamma") exists as a homodimer in which the two polypeptide chains have extensive interactions. Several lysine residues of each polypeptide are adjacent to amino acid residues of IFN-gamma that have been implicated in binding to receptors or are in the dimerization interface. The "ball-and-stick" format of amino acid residue Gln-1 is intended to reflect the evidence for the functional importance of this N-terminal residue. (The crystal structure on which this figure is based included an additional methionine residue, labeled "Met 0," that it is not present in the natural protein.) Since the N-terminal residues of IFN-gamma are remote from the dimerization interface, N-terminal PEGylation could avoid the inhibitory effects of lysine PEGylation on homodimerization of IFN-gamma. On the other hand, the interactions of the dimer with its receptors are likely to be inhibited by coupling polymers to the amino terminus, particularly when long strands of polymer are attached.

IFN-gamma, IL-10 and stem cell factor are examples of cytokines that function as homodimers (Walter, M. R., et al., supra; Josephson, K., et al., (2000) *J Biol Chem* 275:13552-13557; McNiece, I. K., et al., supra). Dimerization of receptor-binding proteins presents special issues for the characterization of their N-terminally monoPEGylated conjugates, since different possible molecular structures can be present in preparations of conjugates with similar or identical size and shape. For example, a dimer that consists of one diPEGylated monomer and one unPEGylated monomer ($PEG_2$-$protein_1$ + $protein_1$) would be difficult or impossible to distinguish from a dimer that consist of two N-terminally PEGylated monomers ($PEG_1$-$protein_1$)$_2$ by most size-based analyses of the dimeric conjugate (e.g., size-exclusion chromatography or evaluation of the sedimentation coefficient, light scattering or diffusion coefficient), yet the receptor-binding potency of these two conjugates, each containing an average of one PEG per protein monomer, might be quite different.

For the long-chain beta-sheet receptor-binding proteins that form homotrimers, e.g. tumor necrosis factor alpha ("TNF-alpha"), the number of isomers of $PEG_3$-$protein_3$ trimers is even larger than for the receptor-binding proteins that occur in solution as homodimers. Since chemical modification of TNF close to the amino terminus has been shown to inactivate this cytokine (Utsumi, T., et al., (1992) *Mol Immunol* 29:77-81), TNF-alpha is not likely to retain substantial activity when PEGylated with reagents and under conditions that are selective for the N-terminal residue.

For the characterization of conjugates of cytokines that function as oligomers, a combination of analytical methods is required. Amino-terminal sequence analysis can detect the presence of monomers with free N-terminal alpha amino groups and electrophoretic analysis of dissociated monomers (e.g. SDS-PAGE or capillary electrophoresis) can reveal the presence of unPEGylated and multiply-PEGylated monomers of the receptor-binding proteins. Without such evidence, the synthesis of monoPEGylated conjugates of such homodimer- and homotrimer-forming proteins cannot be demonstrated unequivocally.

These examples, especially as graphically illustrated by FIGS. 1-8, provide a readily visualized basis for understanding the potential role of steric hindrance of protein-receptor interactions by PEGylation of receptor-binding proteins within or adjacent to receptor-binding domains of these bioactive components. The large volume that is occupied by the highly extended and flexible PEG strands (see FIG. 1*d*) also would sterically hinder the association of monomers of certain receptor-binding proteins into functional homodimers or homotrimers, if the PEG were coupled in regions that are reported to be required for interactions between the monomers. Thus, the targeting of PEGylation to sites that are remote from receptor-binding regions of receptor-binding proteins decreases the likelihood that PEGylation will interfere with the intermolecular interactions that are required for their function. By proceeding in accordance with the method of this invention, more of the benefits that are expected from PEGylation of receptor-binding proteins can be realized. The resulting conjugates combine the expected benefits of improved solubility, increased bioavailability, greater stability and decreased immunogenicity with an unexpectedly high retention of bioactivity.

Example 4

PEGylation of Interferon-β-1b by Reductive Alkylation

In one series of embodiments, conjugates of interferon-β-1b ("IFN-β-1b;" SEQ ID NO:1) with monomethoxyPEG ("mPEG") were synthesized by reductive alkylation with 20-kDa or 30-kDa mPEG-aldehyde, using borane-pyridine complex as the reducing agent (Cabacungan, J. C., et al., supra). Interferon-β-1b, free of carrier proteins and at a concentration of about 1.9 mg/mL in a solution containing approximately 3 mg/mL SDS, was obtained from Chiron Corporation (Emeryville, Calif.). This protein is referred to as "BETASERON®" in the formulation that is marketed by Berlex Laboratories, a U.S. subsidiary of Schering AG, and as "BETAFERON®" in the formulation that is marketed directly by Schering. Borane-pyridine complex (Aldrich 17,975-2, Milwaukee, Wis.) was diluted to 450 mM borane in 60% (v/v) aqueous acetonitrile. 20-kDa mPEG n-propionaldehyde ("PEG-aldehyde;" NOF Corporation, Tokyo) was dissolved in 1 mM HCl at a concentration of 30 mg/mL. After dissolution, 0.1 mL of the PEG-aldehyde solution was added to 0.7 mL of IFN-β-1b solution and mixed. Addition of 0.05 mL of 100 mM acetate buffer, pH 4.6, gave the reaction mixture a final pH of 5. To another reaction mixture containing 0.1 mL of PEG-aldehyde solution and 0.7 mL of IFN-β-1b solution, 0.05 mL of a mixture of 200 mM acetic acid, 200 mM $Na_2HPO_4$ and 68 mM NaOH was added to give a final pH of 6.4. To three 0.85-mL aliquots of each of these mixtures, 0.1 mL of either water, 1.5 M NaCl or 10 mg/mL SDS was added. The diluted borane-pyridine complex was then added to each reaction mixture to give a final concentration of 23 mM borane. Each of the resultant reaction mixtures was divided into two tubes that were incubated for 2 days at either 4° C. or room temperature. Aliquots of the reaction mixtures were analyzed by size-exclusion HPLC in 10 mM Tris, 150 mM NaCl, pH 8.3, containing 0.3 mg/mL SDS, at a flow rate of 0.5 mL/min on a SUPEROSE® 12 gel filtration chromatography media column (Amersham Biosciences HR 10/30; Piscataway, N.J.). The absorbance of the eluate was monitored at 214 nm. With an input ratio of approximately 2 moles of PEG per mole of protein, the predominant species was monoPEGylated interferon-β-1b ($PEG_1$-IFN-β-1b). The yield of $PEG_1$-IFN-β-1b was between 65% and 72% under all of the tested incubation conditions (at pH 5 or pH 6.4; at 4° C. or room temperature; in the presence or absence of NaCl or additional SDS).

In other experiments, $NaBH_3CN$ was used as the reducing agent and the samples were analyzed by size-exclusion HPLC on a SUPERDEX® 200 HR 30/10 gel filtration chromatography media column (Amersham Biosciences) in 10 mM acetate, 150 mM NaCl, pH 4.6, containing 1 mg/mL SDS, at a flow rate of 0.5 mL/min. The results of one such experiment are shown in FIG. 14. The input concentrations of 20-kDa mPEG were approximately 0.1 mM, 0.2 mM and 0.4 mM (designated "1×," "2×" and "4×" in FIG. 14, respectively) and the reaction mixtures were incubated at room temperature for 3 days. The control sample (bottom tracing) was incubated with only the reducing agent. When the same samples were chromatographed under the same conditions except for the omission of SDS from the elution buffer, the unPEGylated IFN-β-1b was not detected in the eluate. Similar results were obtained when 30-kDa mPEG n-propionaldehyde was substituted for 20-kDa mPEG n-propionaldehyde in the methods of this Example 4. Similar results were also obtained when 10-kDa mPEG n-propionaldehyde was substituted for 20-kDa mPEG n-propionaldehyde. Alternatively, mPEG-acetaldehydes or butyraldehydes can be employed. Selective N-terminal PEGylation of IFN-β by the method of this example produces conjugates of enhanced bioactivity whether the N-terminal amino acid is serine, as in IFN-β-1b, methionine, as in IFN-β-1a, or another amino acid.

Example 5

Determination of the Extent of N-terminal PEGylation by Oxidative Cleavage

The fraction of PEG coupled to the alpha amino group of the N-terminal serine residue of a protein, rather than the epsilon amino groups of accessible lysine residues, was assessed by a novel method involving oxidative cleavage of the alkylated serine residue. A reaction mixture in which $PEG_1$-IFN-β-1b was the predominant species (approximately 70% of the total protein) was dialyzed against 1 mg/mL SDS in acetate buffer, pH 4.6. The pH was then adjusted to 7.4 by the addition of 10 mM $Na_3PO_4$. Portions of this solution were incubated at 4° C. for up to 20 hours in the absence of sodium periodate or with final concentrations of 0.1 through 10 mM $NaIO_4$. Following incubation, the reaction mixtures were chromatographed on a SUPEROSE® 6 gel filtration chromatography media column in 10 mM acetate buffer, 150 mM NaCl, pH 4.6, containing 1 mg/mL SDS. Similar results with respect to the recovery of monoPEGylated IFN-β-1b were obtained on a SUPEROSE® 12 gel filtration chromatography media column, with the advantage that the SUPEROSE® 12 gel filtration chromatography media column permitted resolution of the unmodified IFN-β-1b from the "salt peak." A graph of the areas under the peaks of absorbance at 214 nm corresponding to $PEG_1$-IFN-β-1b versus periodate concentration showed a steep decrease in the area up to about 1 mM periodate and a nearly constant level of residual $PEG_1$-IFN-β-1b between about 1 mM and 10 mM periodate. Similar analyses after treatment with ≥3 mM periodate for 0.2, 2 or 7 hours indicated that the oxidative cleavage of the serine-linked PEG was substantially complete within 2 hours. The residual PEG conjugates contained only lysine-linked PEG, which linkage was stable to treatment with up to at least 10 mM periodate. The fraction of the conjugates that survived oxidation with periodate was similar to the fraction estimated by Edman degradation to be PEGylated at sites other than the amino terminal. Similar results are obtained when the distribution of conjugates that are stable or unstable to the oxidative procedures described in this example is assessed by a variety of analytical methods, including, but not limited to reversed phase chromatography, capillary electrophoresis, gel electrophoresis, ultracentrifugation, mass spectroscopy, light scattering or ultrafiltration.

Interferon-β-1b was coupled to 20-kDa PEG-aldehyde with borane-pyridine complex as the reducing agent under various conditions, as described in Example 4. The monoPEGylated IFN-β-1b was purified by chromatography on a SUPEROSE® 12 gel filtration chromatography media column in 20 mM sodium phosphate buffer, 150 mM NaCl, pH 7.4, containing 0.3 mg/mL SDS, at a flow rate of 0.5 mL/min. Portions of the purified $PEG_1$-β-1b conjugates were incubated for 2 hours at room temperature in the absence or presence of 3 mM sodium periodate. FIG. 15 shows chromatograms of the untreated and oxidatively cleaved samples of $PEG_1$-IFN-β-1b on a SUPEROSE® 12 gel filtration chromatography media column in 10 mM Tris, 150 mM NaCl, pH 8.3, containing 0.3 mg/mL SDS, run at 0.5 mL/min. These data indicate that approximately 90% of the PEG in $PEG_1$-

IFN-β-1b synthesized at pH 6.4 was coupled to the N-terminal serine. This result was not altered significantly by performing the coupling after the addition of either 150 mM NaCl (lower curves) or 1 mg/mL SDS (upper curves) to the reaction mixtures or by performing the coupling reactions at pH 5 (results not shown). Similar results are obtained when monohydroxyPEG n-propionaldehydes are substituted for mPEG n-propionaldehydes or when PEG aldehydes other than n-propionaldehyde are employed. Likewise, the method of this example measures the extent of N-terminal reductively alkylated proteins other than IFN-β-1b, wherein such proteins have an N-terminal serine residue. Similarly, oxidative cleavage of polymers linked by reductive alkylation to N-terminal serine residues is achieved using periodates other than sodium periodate, including, but not limited to: sodium metaperiodate (referred to elsewhere herein and known in the art as sodium periodate), potassium metaperiodate, lithium metaperiodate, calcium periodate, barium periodate and periodic acid.

Polymer conjugates synthesized by reductive alkylation of other cytokines to which the method of this Example 5 are applicable include interleukin-1-alpha (Geoghegan, K. F., et al., supra) and megakaryocyte growth and development factor (Guerra, P. I., et al., supra).

Example 6

Purification of Conjugates and Removal of Free PEG and SDS by Reversed Phase Chromatography Reversed phase ("RP") chromatography was used by S. Hershenson et al. (U.S. Pat. No. 4,894,330), to purify IFN-β-1b after its expression in bacterial cell culture. The present inventors adapted the methods of Hershenson et al. to separate the individual PEGylated species synthesized as described in Example 4 from the unmodified protein. This procedure also resolved the free PEG and most of the SDS from the protein peaks. FIG. 16 shows an analytical chromatogram on a Jupiter™ C4 300 Å column (15 cm×4.6 mm; Phenomenex; Torrance, Calif.) with a gradient of 20% acetonitrile plus 0.04% trifluoroacetic acid to 80% acetonitrile plus 0.1% trifluoroacetic acid. One-tenth milliliter of the reaction mixture was loaded and 0.5 mL fractions were collected at a flow rate of 1 mL/min. A peak of IFN-β-1b that was unmodified except by exposure to the PEGylation reagents ("Mock PEGylated") and peaks of PEG conjugates containing one or more strands of PEG per molecule of protein were detected by monitoring the absorbance at 280 nm (solid curve). In this experiment, the column was maintained at 40° C. Qualitatively similar results, but with different retention times, were obtained by chromatography at room temperature.

The results of assays of SDS in the collected fractions are shown by the open triangles. A stock solution of the SDS assay reagent contained 1 mg/mL of a carbocyanine dye, Stains-All (Sigma, #E-9379; 3,3'-diethyl-9-methyl-4,5,4',5'-dibenzothiacarbocyanine), in 50% (v/v) aqueous isopropanol (Rusconi, F., et al., (2001) *Anal Biochem* 295:31-37). The working reagent was prepared just before use by mixing 2 mL of the stock solution plus 2 mL of N,N-dimethylformamide and 41 mL of water. Addition of SDS to this reagent caused spectral changes that are specific to SDS and resulted in a decrease in the absorbance peak at 510-515 nm and the appearance of an absorbance peak at 439 nm. The changes in absorbance at 439 nm upon addition of 2 mcL of each fraction from the RP chromatography column to 250 mcL of the working reagent in a 96-well plate were monitored in a SpectraMax 250 Plate reader (Molecular Devices, Sunnyvale, Calif.).

The results of an assay for PEG in the collected fractions are shown by the filled circles in FIG. 16. The PEG assay reagent was prepared immediately before use by mixing 1 volume of 20% (w/v) barium chloride in 1 N HCl with 4 volumes of 4 mg/mL iodine in 1% (w/v) potassium iodide. From each fraction of the RP chromatography column (and the PEG standards), a 10 mcL aliquot was added to 90 mcL of water in the wells of a 96-well plate, followed by 100 mcL of PEG assay reagent. After the samples and reagent were mixed and incubated at room temperature for 15 minutes, the absorbance at 508 run was measured in a SpectraMax plate reader. The graphs in FIG. 16 demonstrate that RP chromatography under these conditions separated the Mock PEGylated protein from conjugates containing one or more strands of 20-kDa PEG, while resolving the unbound PEG and SDS from the conjugates. Similar results were obtained with conjugates containing PEGs of other molecular weights (e.g., 10-kDa or 30-kDa PEG) and other acid-stable linkages between the PEG and the IFN-β-1b.

Example 7

Chromatographic and Electrophoretic Analyses of Purified Fractions from Preparative Reversed Phase HPLC Reversed phase chromatography under conditions similar to those described in Example 6 was performed on larger samples (0.3 or 0.5 mL) of PEGylation reaction mixtures on the same Jupiter C4 column with a modified gradient. When larger samples were loaded, resolution among the various forms of interferon (Mock PEGylated, $PEG_1$-IFN-β-1b or conjugates with more than one strand of PEG) was not as clear as that shown in FIG. 16. Nevertheless, fractions that were highly enriched either in Mock PEGylated or in monoPEGylated protein were obtained, as shown by rechromatography of small aliquots of the partially purified fractions on the same RP column (FIG. 17). The chromatograms were analyzed using EZChrom Elite software (Scientific Software, Inc., Pleasanton, Calif.). From this analysis, the preparation shown in the upper curve (Fraction 53 from the preparative RP column) contained about 70-80% Mock PEGylated IFN-β-1b, while the preparation shown in the middle curve (Fraction 51) contained about 99% $PEG_1$-IFN-β-1b. The bottom curve in FIG. 17 shows a chromatogram of the reaction mixture from which the fractions were derived, in which about 19% of the absorbance was associated with the Mock PEGylated protein, about 61% with the peak of $PEG_1$-IFN, about 12% with the peak labeled $PEG_2$-IFN, and 5-6% with forms that eluted earlier than $PEG_2$-IFN. Qualitatively similar results are obtained when reversed phase columns from other manufacturers are used.

The same reaction mixture (analyzed by RP chromatography in FIG. 17) and two fractions of PEG-interferon purified by RP chromatography were analyzed by polyacrylamide gel electrophoresis in the presence of SDS ("SDS-PAGE"). The results are shown in FIGS. 18 and 19. Replicate samples were incubated with a reducing agent (Invitrogen, #NP0004; Carlsbad, Calif.) or without reducing agent for 10 minutes either at ambient temperature or at 102° C. and electrophoresed for 140 minutes at 120 V through a 4-12% Bis-Tris gel (Invitrogen, #NP0321B). The tracings shown in FIGS. 18 and 19 were from the samples that were neither reduced nor heated. The proteins in the gel were stained with SYPRO®

Ruby Stain (Molecular Probes #S-12000, Eugene, Oreg.), illuminated at 302 nm and photographed using an Orange/Red visible light filter (Molecular Probes, #S-6655) (FIG. 18). The digital images were analyzed using 1D Imaging Analysis software from Kodak (Rochester, N.Y.). The horizontal axis represents migration distance relative to the dye front (100 units) and the vertical axis represents the relative intensity of the fluorescent protein stain. The baseline values for the various lanes have been shifted vertically to clarify the presentation of the results. The bottom tracing represents a mixture of standard proteins (Mark12™, #LC5677 from Invitrogen), in which the peaks numbered 1 through 9 are identified as proteins having the following molecular weights (all in kDa): 200, 116, 97.1, 66.3, 55.4, 36.5, 31.0, 21.5 and 14.4. The second tracing from the bottom shows the electrophoretic analysis of the reaction mixture. In this mixture, the percentages of protein stain associated with each form of IFN-β-1b were: 14% Mock PEGylated; 64% $PEG_1$-IFN; 20% $PEG_2$-IFN and about 2% of forms larger than $PEG_2$-IFN. The third tracing from the bottom shows a fraction from the RP chromatographic column that contained 33±1% $PEG_1$-EFN; 64±1% $PEG_2$-IFN and about 6% of forms larger than $PEG_2$-IFN. The top curve shows a fraction containing 95±1% $PEG_1$-IFN, about 2% of Mock PEGylated IFN and about 2% of forms larger than $PEG_2$-IFN. The percentages indicated above are the mean and standard deviation of results of four replicate analyses of each sample. Qualitatively similar results were obtained with PEGs of 10 kDa and 30 kDa.

FIG. 19 displays the results from SDS-PAGE analyses, as described for FIG. 18, except the gel was stained for PEG using 20% (w/v) $BaCl_2$ in 1 N HCl combined with 4 volumes of 4 mg/mL $I_2$ in 1% (w/v) KI. The bottom tracing represents a mixture of pre-stained standard proteins (SeeBlue Plus2™, Invitrogen #LC5625), in which the peaks numbered 1 through 9 identify the proteins with the following apparent molecular weights (in kDa): 204, 111, 68.8, 51.5, 40.2, 28.9, 20.7, 14.9 and c. 6. Quantitative analysis of the PEG-stained gel indicates that about 99% of the PEG in Fraction 51 from the RP column (top curve) is associated with $PEG_1$-IFN, while the fraction enriched in the diPEG conjugate (second curve from top) contained 25±1% of $PEG_1$-IFN and about 3% of forms larger than $PEG_2$-IFN, in addition to about 71% of $PEG_2$-IFN. In estimating the relative quantities of the various forms of IFN-β-1b stained for PEG, the area under the $PEG_2$-IFN peak was divided by 2. In the reaction mixture (second curve from bottom), about 50% of PEG stain was associated with unbound PEG, about 35% with $PEG_1$-IFN, about 14% with $PEG_2$-IFN and about 1% with forms larger than $PEG_2$-IFN.

Example 8

Selective N-Terminal Oxidation of Interferon-β-1b and Coupling to a Low Molecular Weight Carbazate An alternative method of coupling mPEG to the amino terminus of IFN-β-1b was used to increase the apparent selectivity for this attachment site to about 100% from the value of about 90% obtained by reductive alkylation, as described in Examples 4 and 5. The first step in this method of PEGylation is based on a similar principle to the oxidative cleavage of reductively alkylated PEG-IFN-β-1b described in Example 5. This approach takes advantage of the unique sensitivity of an N-terminal serine or threonine residue to be cleaved to an aldehyde by periodate, as reported by H. B. F. Dixon (supra) and by K. F. Geoghegan et al., ((1992) *Bioconjug Chem* 3:138-146; Geoghegan, K. F., U.S. Pat. No. 5,362,852; Drummond, R. J., et al., U.S. Pat. No. 6,423,685). When the N-terminal serine residue of IFN-β-1b was maximally oxidized, e.g., after treatment with 3 mM $NaIO_4$ for 2 hours at room temperature, the resulting peak of protein absorbance appeared broad upon preliminary size-exclusion chromatography on a Superose 6 column. Subsequent analysis on a Superose 12 column in 10 mM acetate, 150 mM NaCl, pH 4.6, containing 0.3 mg/mL SDS, clearly resolved the oxidized protein into two forms that were inferred to be monomers and dimers of the protein. The identities of these two peaks were confirmed by SDS-PAGE, performed as described in Example 7.

Analyses by reversed phase chromatography further documented the discovery that preferential oxidation of the N-terminal serine was achieved with minimal oxidation of at least one essential methionine residue. L. S. Lin et al., ((1996) *Pharm Biotechnol* 9:275-301) and L. Lin ((1998) *Dev Biol Stand* 96:97-104) showed that RP chromatography resolved preparations of IFN-β-1b into a major component ("Peak B") and a minor component that eluted earlier ("Peak A"). Lin ((1998) supra) further demonstrated that Peak A contained IFN-β-1b in which a functionally active methionine (Met 61 of BETASERON) was oxidized to a sulfoxide. The present inventors have discovered conditions under which nearly complete oxidation of the N-terminal serine can be achieved with minimal oxidation of Met 61, as reflected in the percentage of Peak A in RP chromatograms. Oxidation of Met 61, as measured by RP chromatography, was used as a surrogate marker for oxidation of the other methionine residues of IFN-β-1b (Met 35 and Met 116 of BETASERON).

Studies of the extent of oxidation of Met 61 as a function of the pH and time of incubation with 0.25 mM $NaIO_4$ at 4° C. are summarized in Table 1.

TABLE 1

Effects of pH and the time of exposure to periodate on the extent of methionine oxidation, as measured by the area of Peak A after reversed phase chromatography.

| Time of Exposure to 0.25 mM $NaIO_4$ | Percent Peak A pH 6.9 | Percent Peak A pH 7.7 |
|---|---|---|
| 0 | 4.9 | 4.8 |
| 2 hours | 5.1 | 5.2 |
| 6 hours | 5.6 | 5.0 |
| 18 hours | 7.3 | 5.4 |
| 9 days | 21.2 | 15.7 |

The demonstration of aldehyde formation by N-terminal oxidation of IFN-β-1b was facilitated by its conjugation to 9-fluorenylmethyl carbazate ("Fmoc-carbazate," also known in the art as "Fmoc-hydrazide") (Fluka 46917; Zhang, R.-E., et al., (1991) *Anal Biochem* 195:160-167). The distinctive absorbance spectra of Fmoc-carbazate adducts of IFN-β-1b enabled their discrimination from the corresponding unconjugated forms of the protein without the use of a fluorescence detector. Interferon-β-1b was oxidized by treatment with various concentrations of $NaIO_4$ at pH 7.8 for various periods of time (0.5 to 2 hours at room temperature or up to several days in the cold). In the experiments shown in FIG. 20, the protein was incubated for 1 hour at room temperature with 0.5 mM $NaIO_4$. The reaction was terminated by the addition of glycerol. After 30 minutes at room temperature, the pH was reduced by the addition of acetic acid to a final concentration of 19 mM. To each mL of resultant mixture, 182 mcL of 15 mM Fmoc-carbazate in methanol was added to give a final concentration of 2.3 mM Fmoc-carbazate. This reaction mixture was incubated overnight at 4-8° C. prior to analysis by reversed phase chromatography.

FIG. 20 illustrates the effects on RP chromatographic behavior of incubation of IFN-β-1b with 0.5 mM $NaIO_4$ for 1 hour at room temperature and of coupling of the products of oxidation to Fmoc-carbazate. A comparison of the results for the control sample (upper curve) with those for the oxidized sample (middle curve with open circles) shows that the retention times of both the main component and of Peak A (reflecting the presence of about 5% of IFN-β-1b with an oxidized methionine residue) are increased by 0.2 to 0.3 minutes by oxidation. As measured by the percentage of Peak A, compared to Peak A', less than 1% oxidation of methionine was detected after incubation with $NaIO_4$ under these conditions.

The results of bioassays that are described in Example 11 provide additional evidence that controlled oxidation (e.g., for up to 2 hours in the cold) with 0.1 to 0.3 mM periodate preserved the integrity of the amino acid residues of the protein that are essential for bioactivity.

As shown in the lower curve with filled triangles in FIG. 20, evidence for the formation of Fmoc adducts was provided by the shift to longer retention times for both the major component and Peak A' (the N-terminal aldehyde derivative of Peak A). Furthermore, there was a 50% increase in the ratio of absorbance at 278 nm to that at 214 nm for the shifted peaks. For both forms of the protein, the increases in retention times due to formation of the corresponding N-terminal aldehydes (0.2-0.3 minutes) were much smaller than the increases resulting from formation of the corresponding Fmoc derivatives (1.0-1.2 minutes).

Example 9

Synthesis of PEG-Carbazate Adducts of N-Terminally Oxidized Interferon-β-1b

Interferon-β-1b, selectively oxidized at the amino terminus as described in Example 8, was also coupled to a carbazate derivative of PEG, by an adaptation of methods described by R. J. Drummond et al. (PCT Publication No WO 99/45026; U.S. Pat. No. 6,423,685) and by S. Zalipsky et al., (PCT Publication No. WO 92/16555 A1 and in. Harris, J. M., et al., eds., (1997) *Chemistry and Biological Applications of Poly (ethylene glycol)*, pp. 318-341, Washington, D.C., American Chemical Society). PEG-carbazate was synthesized by the reaction of hydrazine with a p-nitrophenyl carbonate derivative of 20-kDa PEG ("NPC-PEG" from NOF Corporation). After incubation of the protein at room temperature in the absence of periodate or in the presence of 0.125 mM $NaIO_4$ for 0.5, 1 or 2 hours, the samples were diluted with 4 volumes of 20-kDa PEG-carbazate in 10 mM acetate buffer, 150 mM NaCl, pH 4.6, containing 1 mg/mL SDS, and incubated for 1 day at room temperature. The samples were analyzed by size-exclusion chromatography on a SUPEROSE® 12 gel filtration chromatography media column in 10 mM Tris, 150 mM NaCl, pH 8.3, containing 0.3 mg/mL SDS. As shown in FIG. 21, oxidation of the protein for up to 2 hours prior to reaction with PEG-carbazate resulted in a progressive decrease in the concentration of the unmodified protein (eluted at a retention time of about 25 minutes) and a progressive increase in the proportion of absorbance associated with the $PEG_1$-IFN-β-1b conjugate (eluted at a retention time of about 20 minutes). Yields of $PEG_1$-IFN-β-1b exceeding 80% have been obtained by this method. Similar results were obtained using monocarbazate derivatives of 10-kDa or 30-kDa PEG.

Example 10

Bioassay of MonoPEGylated Interferon-β-1b, Purified by Reversed Phase HPLC

The use of human Daudi Burkitt's lymphoma cells (ATCC #CCL-231, Manassas, Va.) for antiproliferative assays of interferon-β-1a and various muteins was described by L. Runkel et al. ((2000) *Biochemistry* 39:2538-2551). FIG. 22 depicts the results of assays of the antiproliferative activities on Daudi cells of untreated IFN-β-1b and an N-terminally monoPEGylated conjugate that was partially purified by RP chromatography. The cells were grown in supplemented RPMI 1640 medium (Gibco #11875-093, Grand Island, N.Y.) with 10% (v/v) fetal calf serum (Irvine Scientific #3000, Santa Ana, Calif.). One hundred thousand cells were inoculated into 250 mcL of medium in each well of a 48-well plate and allowed to grow at 37° C. with 5% $CO_2$ for 4 hours prior to being mixed with an equal volume of pre-warmed medium or dilutions of IFN-β-1b or a PEG conjugate in medium. During 3 days, the number of cells diluted only with medium increased to 590±24% (s.d.) of the number at time zero, based on cell counts with a Coulter counter (Model ZI, Miami, Fla.). Under conditions of maximal growth inhibition by IFN-β-1b or its PEG conjugates, the number of cells increased to 283±8% of the number at time zero. Thus the maximal percent of growth inhibition observed in this experiment was 48%. The data in FIG. 22 for various concentrations of two preparations of IFN-β-1b are expressed as a percent of the inhibitable cell growth.

FIG. 22 shows the results from a study using dilutions of the stock solution of IFN-β-1b and of fractions from the preparative reversed phase chromatographic experiment described in Example 7 that contained either nearly pure monoPEG conjugate, as shown in FIGS. 17-19 (Fraction 51), or nearly pure Mock PEGylated IFN-β-1b (Fraction 53 of the column shown in FIG. 17). The samples were diluted, in triplicate, to 1 mcg/mL in medium supplemented with fetal calf serum and sterilized by filtration through a 0.2-micrometer filter. From each of the initial dilutions, a 32 ng/mL dilution and subsequent serial dilutions were made. From the data in FIG. 22, the concentration of each preparation required for inhibition of 50% of the inhibitable cell growth ("$IC_{50}$") was calculated. The results showed that the mono-PEGylated IFN-β-1b ($IC_{50}$=c. 40 pg/mL) was approximately 6 times as potent as the unmodified IFN-β-1b ($IC_{50}$=c. 250 pg/mL). The mean increases in antiproliferative potencies of conjugates with PEGs of various sizes, tested in a series of experiments similar to that shown in FIG. 22, had a range of about 2.5-fold (for 10 kDa PEG) to about 5-fold (for 30 kDa PEG).

Surprisingly, the Mock PEGylated preparation shown in FIG. 22 had an $IC_{50}$ of about 80 pg/mL, which was intermediate between those of the stock solution of IFN-β-1b and the monoPEGylated preparation. While not intending to be bound by theory or any particular mechanistic explanation, it is plausible that the enhanced antiproliferative potency of the Mock PEGylated preparation reflects the removal during reversed phase chromatography of some inhibitory material that is present in the stock IFN-β-1b solution. This interpretation is consistent with the results of size-exclusion chromatography on a column of SUPEROSE® 6 gel filtration chromatography media in a buffer containing SDS (as described in Example 4), which revealed an absorbance peak at both 214 nm and 280 nm that eluted between the elution positions of IFN-β-1b and the "salt peak." Bioassay experiments similar to those shown in FIG. 22 were performed on Fraction 49 from the RP column, which contained a mixture of $PEG_2$- and PEG$_1$-IFN-β-1b (see FIGS. 18 and 19). As in the case of the Mock PEGylated sample, the multiply PEGylated sample had antiproliferative potency that was greater than that of the stock solution of IFN-β-1b, but less than that of the monoP-EGylated conjugate. In other experiments, the increase in potency observed with monoPEGylated IFN-β-1b ranged from six-fold to ten-fold. Similar increases in potency were observed with the carbazate adducts described in Example 9, employing PEGs of 10, 20 and 30 kDa.

The antiproliferative potencies on Daudi cells obtained with the conjugates of this invention can be compared with the reported specific activities of three pharmaceutical forms of interferon-β measured in an antiviral assay. According to the respective package inserts, the activities are $32 \times 10^6$ IU/mg for Berlex's BETASERON® (IFN-β-1b), $200 \times 10^6$ IU/mg for AVONEX® (Biogen's formulation of IFN-β-1a) and $270 \times 10^6$ IU/mg for REBIF® (Serono's formulation of IFN-β-1a). Accordingly, the increase of at least six-fold in the potency of monoPEGylated BETASERON in the antiproliferative assay illustrated in FIG. 22 indicates that N-terminal PEGylation of BETASERON by the methods of this invention has increased its potency to the range expected for the commercially available glycosylated preparations, AVONEX and REBIF.

Previously, the solubility of nonglycosylated interferon-β (expressed in *Escherichia coli*), has been enhanced by the use of acidic solutions (Hanisch, W. H. et al., U.S. Pat. No. 4,462,940) or by the addition of SDS (Thomson, J. W., U.S. Pat. No. 4,816,440). Without intending to be bound by theory, one mechanism by which PEGylation may increase the antiproliferative efficacy of IFN-β-1b measured in vitro is by decreasing its tendency to self-associate in the culture medium. Accordingly, the observation that the sample enriched in PEG$_2$-IFN-β-1b was less effective than PEG$_1$-IFN-β-1b indicates that the positive effects of decreased aggregation may be overcome by the negative effect of excessive PEGylation on the ability of this cytokine to bind to its receptors and/or to initiate the signal transduction responsible for its antiproliferative activity.

Example 11

Bioassays of Selectively Oxidized Interferon-β-1b

Assays of the antiproliferative activity on Daudi cells of TN-β-1b oxidized to various extents were performed as described in Example 10. The tested samples included the stock solution of IFN-β-1b and samples that had been treated for several days at 4° C. with 0.1, 0.3 or 3 mM periodate. The samples were diluted as described in Example 10 and mixed with an equal volume of Daudi cell suspension, 4 hours after inoculation of the cells. The cells were grown for 2 days at 37° C. with 5% $CO_2$ and then counted with a Coulter counter. The antiproliferative activity of IFN-β-1b was unaffected or increased by treatment with 0.075-0.5 mM $NaIO_4$ under the conditions tested. Similar results were obtained in 3-day antiproliferative assays, as described in Example 10. Antiproliferative potency was further enhanced by conjugation of the selectively oxidized IFN-β-1b with PEG-carbazate, as described in Example 9. Similar results to those obtained with PEG-carbazate are obtained with products of conjugation of selectively oxidized IFN-β-1b to PEG-hydrazide. In contrast, the antiproliferative effect on Daudi cells was suppressed or completely abolished by treatment of IFN-β-1b with higher concentrations of periodate, e.g. 1-3 mM. These high concentrations of $NaIO_4$ induced dimerization of the protein, which was detected by size-exclusion HPLC on a SUPEROSE® 12 gel filtration chromatography media column, as described in Example 5, and oxidation of methionine, as detected by reversed phase chromatography, as described in Example 6 (results not shown).

Bioactivities of the conjugates of this invention can be measured by art-known antiproliferative and antiviral assays based on various cell lines or primary cultures, wherein the cells bear cell-surface receptors for IFN-beta. Alternatively, one can monitor responses to IFN-beta that include the induction of neopterin (Pepinsky, R. B., et al., supra), β$_2$-microglobulin (Pepinsky, R. B., et al., supra), or 2'-5'-oligoadenylate synthetase (Bruchelt, G., et al., (1992) *Eur. J. Clin Chem Clin Biochem* 30:521-528) or reporter proteins operatively linked to the promoters of proteins that are inducible by IFN-beta. Additional methods for assaying the bioactivity of polymer conjugates of IFN-beta include signal transduction assays and gene activation assays (e.g., Pungor, E., et al., (1998) *J Interferon Cytokine Res* 18:1025-1030).

This invention is described with reference to certain embodiments and certain examples thereof. The methods of this invention are similarly applicable to certain receptor-binding peptides and proteins other than cytokines or their antagonists and to other conjugation reagents. Therefore, the scope of this invention is not limited to the embodiments described, but is limited only by the scope of the claims. Workers of ordinary skill in the art can readily appreciate that other embodiments can be practiced without departing from the scope of this invention. All such variations are considered to be part of this invention.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising a detergent and a non-glycosylated interferon-beta conjugate prepared by selectively coupling one or more synthetic water-soluble polymers to the amino-terminal amino acid of a non-glycosylated interferon-beta,
   wherein said one or more synthetic water-soluble polymers is selected from the group consisting of one or more polyethylene glycols and one or more polyethylene oxides,
   wherein said amino-terminal amino acid is located remotely from the receptor-binding domain(s) of said interferon-beta, and
   wherein said conjugate has increased in vitro biological potency as compared to said non-glycosylated interferon-beta that has not been coupled with one or more synthetic water-soluble polymers when assayed under the same conditions.

2. The composition of claim 1, which is pharmaceutically acceptable.

3. A composition comprising a detergent and a conjugate that comprises a non-glycosylated interferon-beta selectively and covalently coupled at its amino-terminal amino acid to one or more synthetic water-soluble polymers,
   wherein said one or more synthetic water-soluble polymers is selected from the group consisting of one or more polyethylene glycols and one or more polyethylene oxides,
   wherein said amino-terminal amino acid is located remotely from the receptor-binding domain(s) of said interferon-beta, and
   wherein the in vitro biological potency of said interferon-beta is increased compared to the same interferon-beta that has not been so coupled when assayed under the same conditions.

4. A composition comprising a detergent and a conjugate that comprises a non-glycosylated interferon-beta selectively and covalently coupled at its amino-terminal amino acid to one or more synthetic water-soluble polymers,
   wherein said one or more synthetic water-soluble polymers is selected from the group consisting of one or more polyethylene glycols and one or more polyethylene oxides,
   wherein said amino-terminal amino acid is located remotely from the receptor-binding domain(s) of said interferon-beta, and
   wherein the in vitro biological potency of said conjugate of interferon-beta is increased compared to the same interferon-beta to which the same number of the same synthetic water-soluble polymers has been coupled randomly to solvent-accessible lysine residues when assayed under the same conditions.

5. The composition of claim 3 or claim 4, wherein said interferon-beta has the amino acid sequence of interferon-β-1b specified in SEQ ID NO:1.

6. The composition of claim 5, wherein the in vitro biological potency of said interferon-β-1b is increased to approximately the in vitro potency of interferon-β-1a, which interferon-β-1a has the amino acid sequence specified in SEQ ID NO:2 and is glycosylated on asparagine residue 80.

7. The composition of claim 3 or claim 4, wherein said polymer is selectively and covalently coupled to the alpha amino group of the amino-terminal amino acid of said interferon-beta.

8. The composition of claim 7, wherein said selective and covalent coupling of said polymer to said alpha amino group is via a secondary amine linkage.

9. The composition of claim 3 or claim 4, wherein said polymer is, or said polymers are, coupled to a chemically reactive side chain group of said amino-terminal amino acid.

10. The composition of claim 9, wherein said reactive side chain group is an aldehyde group that is introduced by selective oxidative cleavage of an amino-terminal serine or threonine residue of an interferon-beta.

11. The composition of claim 3 or claim 4, wherein said one or more water-soluble polymers is a polyalkylene glycol.

12. The composition of claim 11, wherein said one or more polyalkylene glycol(s) is selected from the group consisting of a poly(ethylene glycol), a mono-methoxypoly(ethylene glycol) and a monohydroxypoly(ethylene glycol).

13. The composition of claim 12, wherein said one or more polyalkylene glycol(s) is a monomethoxypoly(ethylene glycol).

14. The composition of claim 12, wherein said one or more polyalkylene glycol(s) is a monohydroxypoly(ethylene glycol).

15. The composition of claim 11, wherein said one or more polyalkylene glycol(s) has a molecular weight of between about 1 kDa and about 100 kDa, inclusive.

16. The composition of claim 15, wherein said one or more polyalkylene glycol(s) has a molecular weight of between about 8 kDa and about 14 kDa, inclusive.

17. The composition of claim 15, wherein said one or more polyalkylene glycol(s) has a molecular weight of between about 10 kDa and about 30 kDa, inclusive.

18. The composition of claim 17, wherein said one or more polyalkylene glycol(s) has a molecular weight of between about 18 kDa and about 22 kDa, inclusive.

19. The composition of claim 18, wherein said one or more polyalkylene glycol(s) has a molecular weight of about 20 kDa.

20. The composition of claim 15, wherein said one or more polyalkylene glycol(s) has a molecular weight of about 30 kDa.

21. The composition of claim 3 or claim 4, wherein the coupling of said one or more polymers to said interferon-beta at said amino-terminal amino acid pseudoglycosylates or pseudohyperglycosylates said interferon-beta.

22. The composition of claim 3 or claim 4, which is pharmaceutically acceptable.

23. The composition of claim 1, wherein the in vitro biological potency of said conjugate is measured in a cell-culture assay that responds to interferon-beta.

24. The composition of claim 23, wherein said assay is selected from the group consisting of an antiproliferative assay, an antiviral assay, a signal transduction assay and a gene activation assay.

25. The composition of claim 24, wherein said assay is an antiproliferative assay.

26. The composition of claim 3, wherein the in vitro biological potency of said conjugate is measured in a cell-culture assay that responds to interferon-beta.

27. The composition of claim 26, wherein said assay is selected from the group consisting of an antiproliferative assay, an antiviral assay, a signal transduction assay and a gene activation assay.

28. The composition of claim 27, wherein said assay is an antiproliferative assay.

29. The composition of claim 4, wherein the in vitro biological potency of said conjugate is measured in a cell-culture assay that responds to interferon-beta.

30. The composition of claim 29, wherein said assay is selected from the group consisting of an antiproliferative assay, an antiviral assay, a signal transduction assay and a gene activation assay.

31. The composition of claim 30, wherein said assay is an antiproliferative assay.

32. The composition of claim 1, wherein said detergent is sodium dodecyl sulfate (SDS).

33. The composition of claim 3, wherein said detergent is sodium dodecyl sulfate (SDS).

34. The composition of claim 4, wherein said detergent is sodium dodecyl sulfate (SDS).

35. A kit comprising the composition of claim 1.

36. A kit comprising the composition of claim 3 or claim 4.

37. A kit comprising the pharmaceutically acceptable composition of claim 2.

38. A kit comprising the pharmaceutically acceptable composition of claim 22.

\* \* \* \* \*

SEQUENCE LISTING

```
<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
```

```
            20                  25                  30
Asp Arg Met Asn Phe Asp Ile Pro Glu Glu Ile Lys Gln Leu Gln
            35                  40                  45
Phe Gln Lys Glu Asp Ala Ala Leu Thr Ile Tyr Glu Met Leu Gln
        50                  55                  60
Asn Ile Phe Ala Ile Phe Arg Gln Asp Ser Ser Ser Thr Gly Trp Asn Glu
65                  70                  75                  80
Thr Ile Val Glu Asn Leu Leu Ala Asn Val Tyr His Gln Ile Asn His
                85                  90                  95
Leu Lys Thr Val Leu Glu Glu Lys Leu Glu Lys Glu Asp Phe Thr Arg
            100                 105                 110
Gly Lys Leu Met Ser Ser Leu His Leu Lys Arg Tyr Tyr Gly Arg Ile
            115                 120                 125
Leu His Tyr Leu Lys Ala Lys Glu Tyr Ser His Cys Ala Trp Thr Ile
            130                 135                 140
Val Arg Val Glu Ile Leu Arg Asn Phe Tyr Phe Ile Asn Arg Leu Thr
145                 150                 155                 160
Gly Tyr Leu Arg Asn
            165

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln
1               5                   10                  15
Cys Gln Lys Leu Leu Trp Gln Leu Asn Gly Arg Leu Glu Tyr Cys Leu
            20                  25                  30
Lys Asp Arg Met Asn Phe Asp Ile Pro Glu Glu Ile Lys Gln Leu Gln
            35                  40                  45
Gln Phe Gln Lys Glu Asp Ala Ala Leu Thr Ile Tyr Glu Met Leu Gln
        50                  55                  60
Asn Ile Phe Ala Ile Phe Arg Gln Asp Ser Ser Ser Thr Gly Trp Asn
65                  70                  75                  80
Glu Thr Ile Val Glu Asn Leu Leu Ala Asn Val Tyr His Gln Ile Asn
                85                  90                  95
His Leu Lys Thr Val Leu Glu Glu Lys Leu Glu Lys Glu Asp Phe Thr
            100                 105                 110
Arg Gly Lys Leu Met Ser Ser Leu His Leu Lys Arg Tyr Tyr Gly Arg
            115                 120                 125
Ile Leu His Tyr Leu Lys Ala Lys Glu Tyr Ser His Cys Ala Trp Thr
            130                 135                 140
Ile Val Arg Val Glu Ile Leu Arg Asn Phe Tyr Phe Ile Asn Arg Leu
145                 150                 155                 160
Thr Gly Tyr Leu Arg Asn
            165
```